US011571183B2

(12) United States Patent
Lee et al.

(10) Patent No.: US 11,571,183 B2
(45) Date of Patent: Feb. 7, 2023

(54) ELECTRONIC DEVICE AND OPERATION METHOD THEREOF

(71) Applicant: Samsung Electronics Co., Ltd., Gyeonggi-do (KR)

(72) Inventors: Miyoung Lee, Seoul (KR); Jong-Chae Moon, Seoul (KR); Minkyoung Yoon, Seoul (KR); Hyunjin Kim, Seoul (KR)

(73) Assignee: Samsung Electronics Co., Ltd

( * ) Notice: Subject to any disclaimer, the term of this patent is extended or adjusted under 35 U.S.C. 154(b) by 1185 days.

(21) Appl. No.: 16/075,835

(22) PCT Filed: Feb. 6, 2017

(86) PCT No.: PCT/KR2017/001248
§ 371 (c)(1),
(2) Date: Aug. 6, 2018

(87) PCT Pub. No.: WO2017/135769
PCT Pub. Date: Aug. 10, 2017

(65) Prior Publication Data
US 2019/0038260 A1 Feb. 7, 2019

(30) Foreign Application Priority Data
Feb. 5, 2016 (KR) .......................... 10-2016-0015284

(51) Int. Cl.
*A61B 8/08* (2006.01)
*A61B 8/00* (2006.01)
(Continued)

(52) U.S. Cl.
CPC .............. *A61B 8/5207* (2013.01); *A61B 5/00* (2013.01); *A61B 8/00* (2013.01); *A61B 8/4411* (2013.01);
(Continued)

(58) Field of Classification Search
CPC ........... A61B 8/5207; A61B 5/00; A61B 8/00; A61B 8/4411; A61B 8/4427;
(Continued)

(56) References Cited

U.S. PATENT DOCUMENTS 6,063,030 A * 5/2000 Vara ........................ G16H 40/63
600/440
6,261,234 B1 * 7/2001 Lin ......................... A61B 8/445
600/463
(Continued)

FOREIGN PATENT DOCUMENTS

EP   3 005 946    4/2016
JP   08150126    6/1996
(Continued)

OTHER PUBLICATIONS

European Search Report dated Mar. 4, 2019 issued in counterpart application No. 17747814.6-1124, 13 pages.
(Continued)

*Primary Examiner* — Sanjay Cattungal
(74) *Attorney, Agent, or Firm* — The Farrell Law Firm, P.C.

(57) ABSTRACT

Various embodiments of the present invention disclose A method and an apparatus for an ultrasound diagnosis based on an electronic device. According to various embodiments of the present invention, the electronic device includes: a display; a camera; a first communication circuit for probe connection; a second communication circuit for communication with at least one external device; and a processor electrically connected with the display, the camera, the first communication circuit, and the second communication circuit, wherein the processor can be configured to detect an ultrasonic diagnosis mode, execute the ultrasonic diagnosis mode and establish communication with the external device in response to the detection of the ultrasonic diagnosis mode,
(Continued)

acquire data in the ultrasonic diagnosis mode, display the data on the display and transmit the data streaming to the external device using the second communication circuit, and provide an control guide for the probe in response to reception of control information from the external device. Various embodiments are possible.

13 Claims, 44 Drawing Sheets

(51) Int. Cl.
    *A61B 5/00*     (2006.01)
    *G16Z 99/00*     (2019.01)
    *G16H 40/67*     (2018.01)
    *G16H 30/20*     (2018.01)
    *G16H 30/40*     (2018.01)

(52) U.S. Cl.
    CPC .......... *A61B 8/4427* (2013.01); *A61B 8/4472* (2013.01); *A61B 8/465* (2013.01); *A61B 8/468* (2013.01); *A61B 8/5223* (2013.01); *A61B 8/5253* (2013.01); *A61B 8/54* (2013.01); *A61B 8/565* (2013.01); *A61B 8/582* (2013.01); *G16H 30/20* (2018.01); *G16H 30/40* (2018.01); *G16H 40/67* (2018.01); *G16Z 99/00* (2019.02); *A61B 8/463* (2013.01); *A61B 8/467* (2013.01)

(58) Field of Classification Search
    CPC ....... A61B 8/4472; A61B 8/465; A61B 8/468; A61B 8/5223; A61B 8/5253; A61B 8/54; A61B 8/565; A61B 8/582; A61B 8/463; A61B 8/467; G16H 30/20; G16H 30/40; G16H 40/67; G16Z 99/00
    See application file for complete search history.

(56) References Cited

U.S. PATENT DOCUMENTS

| | | | |
|---|---|---|---|
| 6,468,212 B1* | 10/2002 | Scott ...................... | A61B 8/463 600/440 |
| 7,549,961 B1 | 6/2009 | Hwang | |
| 9,072,471 B2* | 7/2015 | Kato ........................ | A61B 8/462 |
| 9,314,225 B2* | 4/2016 | Steen ...................... | G01S 7/5208 |
| 2003/0195418 A1* | 10/2003 | Barnes ................. | G01S 7/52079 600/437 |
| 2005/0085730 A1* | 4/2005 | Flesch ..................... | A61B 8/12 600/459 |
| 2006/0020204 A1* | 1/2006 | Serra ..................... | G01S 7/5208 600/437 |
| 2010/0217128 A1* | 8/2010 | Betts ..................... | A61B 8/4254 345/184 |
| 2011/0301461 A1 | 12/2011 | Anite | |
| 2012/0133601 A1* | 5/2012 | Marshall ................ | G16H 40/63 345/173 |
| 2013/0142010 A1* | 6/2013 | Ajiki ....................... | A61B 8/466 367/7 |
| 2013/0184587 A1 | 7/2013 | Eom et al. | |
| 2013/0226001 A1* | 8/2013 | Steen ..................... | G01S 7/5208 600/447 |
| 2013/0239052 A1* | 9/2013 | Moody ................... | G06F 3/017 715/810 |
| 2013/0324850 A1* | 12/2013 | Petruzzelli ............. | A61B 8/465 600/407 |
| 2014/0121489 A1 | 5/2014 | Kommu Chs | |
| 2014/0200449 A1* | 7/2014 | Yoo .......................... | A61B 8/54 600/437 |
| 2014/0243669 A1* | 8/2014 | Halmann ............. | A61B 8/4427 600/443 |
| 2014/0276057 A1* | 9/2014 | Lee ......................... | A61B 8/463 600/440 |
| 2014/0282018 A1* | 9/2014 | Amble ................... | G16H 40/63 715/733 |
| 2015/0035959 A1 | 2/2015 | Amble et al. | |
| 2015/0164328 A1* | 6/2015 | Yoshitomi ............ | A61B 5/1128 600/443 |
| 2015/0181629 A1 | 6/2015 | Jun | |
| 2015/0257730 A1* | 9/2015 | Masumoto ............. | G06T 19/00 600/440 |
| 2015/0310581 A1* | 10/2015 | Radulescu ............. | A61B 8/085 348/77 |
| 2016/0228091 A1* | 8/2016 | Chiang ................. | A61B 8/462 |
| 2018/0279996 A1* | 10/2018 | Cox ....................... | A61B 8/466 |
| 2018/0296185 A1* | 10/2018 | Cox ....................... | A61B 8/0841 |

FOREIGN PATENT DOCUMENTS

| | | |
|---|---|---|
| JP | 2006115986 | 5/2006 |
| KR | 1020070032145 | 3/2007 |
| KR | 1020090116849 | 11/2009 |
| KR | 1020100061056 | 6/2010 |
| KR | 1020120090470 | 8/2012 |
| KR | 1020130084467 | 7/2013 |
| KR | 1020140130400 | 11/2014 |
| KR | 1020150084565 | 7/2015 |
| WO | WO 2009/047698 | 4/2009 |

OTHER PUBLICATIONS

European Search Report dated Dec. 14, 2018 issued in counterpart application No. 17747814.6-1124, 13 pages.
Indian Examination Report dated Oct. 28, 2020 issued in counterpart application No. 201837030631, 7 pages.
PCT/ISA/210 Search Report issued on PCT/KR2017/001248 (pp. 3).
PCT/ISA/237 Written Opinion issued on PCT/KR2017/001248 (pp. 7).

* cited by examiner

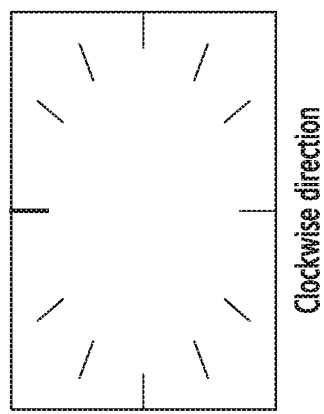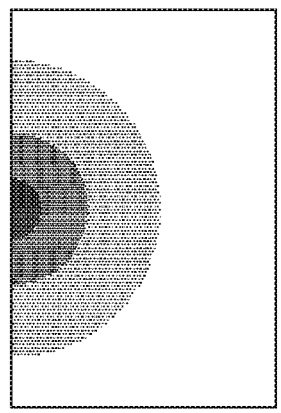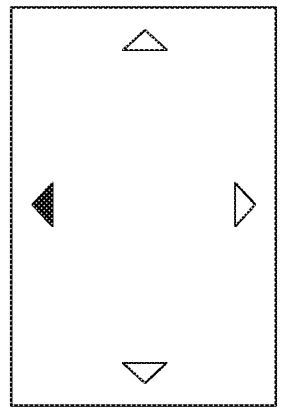
FIG.19A

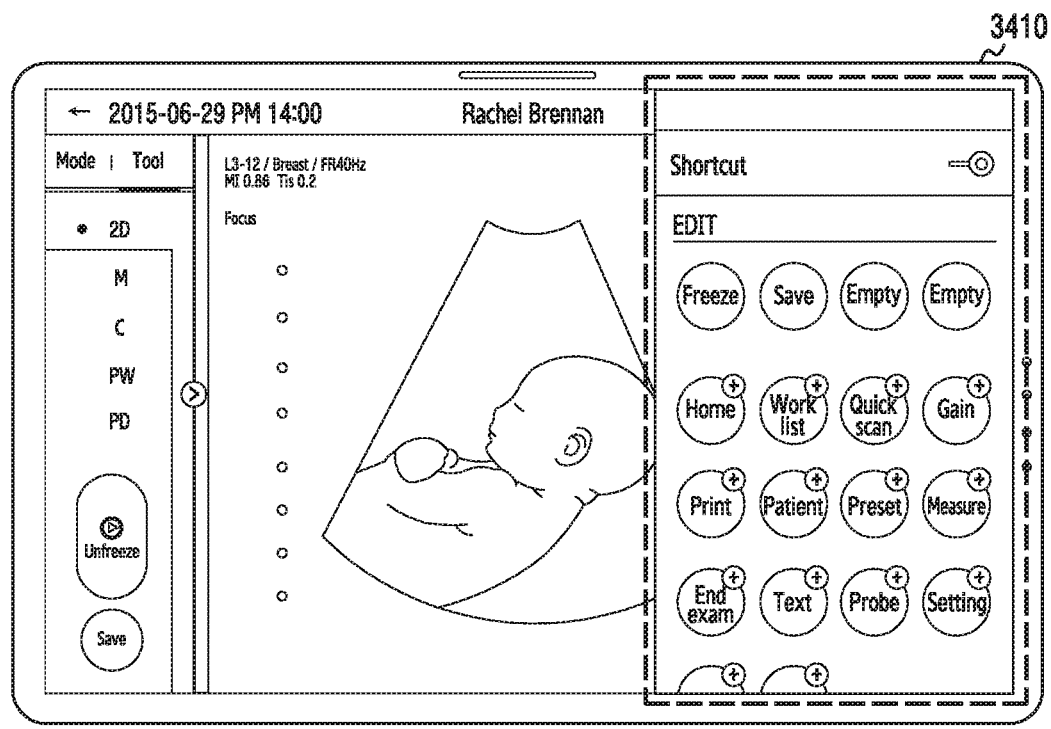
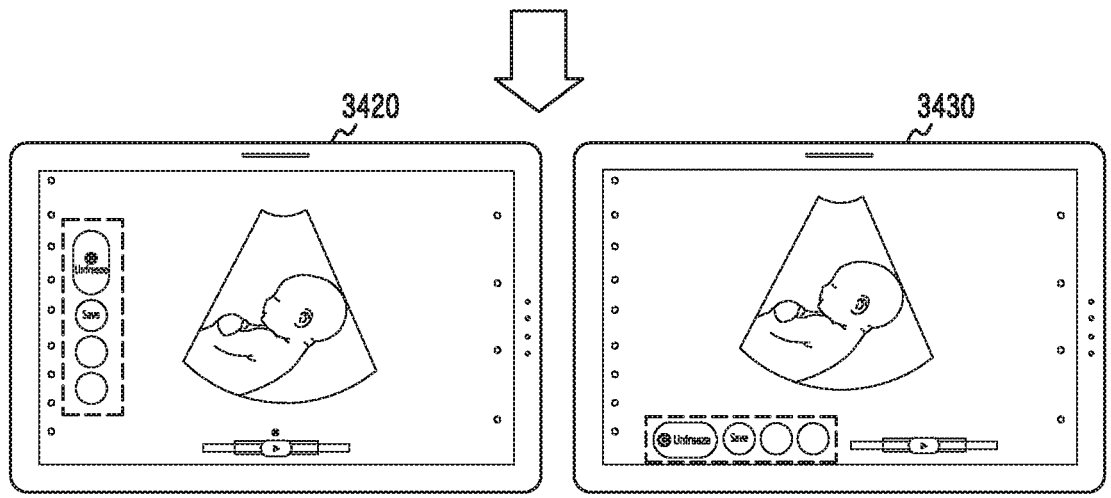
FIG.34

ELECTRONIC DEVICE AND OPERATION METHOD THEREOF

PRIORITY

This application is a National Phase Entry of PCT International Application No. PCT/KR2017/001248, which was filed on Feb. 6, 2017, and claims priority to Korean Patent Application No. 10-2016-0015284, which was filed on Feb. 5, 2016, the contents of each of which are incorporated herein by reference.

TECHNICAL FIELD

The present disclosure relates to a method and an apparatus for providing a telemedicine and a remote treatment using a mobile ultrasound.

BACKGROUND ART

An ultrasound image diagnosis device may radiate an ultrasound signal generated from a transducer of a probe from a body surface of a target to a desired part within the body and acquire an image of the corresponding part inside the target based on information of the ultrasound signal (for example, an ultrasound echo signal) reflected from the target. For example, the ultrasound image diagnosis device may be used for the purpose of observing the inside of the target, detecting foreign materials, and assessing injuries. The ultrasonic image diagnosis device has advantages in that it is more stable than a diagnosis device using an X-ray, can display an image in real time, and it generates no radiation exposure, so that it has been widely used together with other image diagnosis devices.

In general, the ultrasound image diagnosis device includes a control panel through which a user controls the ultrasound image diagnosis device. The control panel includes a touch screen for displaying a menu for optimizing an ultrasound image displayed on a display device and providing a function of selecting the displayed menu, a track ball for moving a cursor displayed on a screen of a display unit and providing a function of searching for an image from a cine image, and a keyboard for inputting text and providing a short-cut function according to a measurement mode, and is mounted to an ultrasound diagnosis system to be movable in upward, downward, leftward, and rightward directions according to a location of a patient.

DETAILED DESCRIPTION OF THE INVENTION

Technical Problem

However, an ultrasound image diagnosis device is generally fixed to and used in a particular space (for example, within an examining room) due to restriction on the size and mobility thereof. Accordingly, for an ultrasound diagnosis of a patient, the patient should move to the corresponding examining room, which inconveniences the patient. Also, there is a problem in that the ultrasound diagnosis cannot be performed in an emergency situation such as a disaster or in emergency relief, or on a patient in a distant place. Although recently telemedicine, visiting care, and medical treatment within elder care home have been gradually increased, a smooth ultrasound diagnosis is difficult due to the limited use of the ultrasound image diagnosis device.

Various embodiments disclose a method and an apparatus for performing a function of the ultrasound image diagnosis device using the electronic device and providing telemedicine according to the function.

Various embodiments disclose a method and an apparatus for sharing, in real time, a status of a patient in a distant palace and an ultrasound diagnosis condition with a doctor in a distant place through a communication function or a camera function of the electronic device based on the connection between the electronic device and probe.

Various embodiments disclose a method and an apparatus for providing telemedicine by switching an ultrasound image screen acquired by the electronic device to a telemedicine screen.

Various embodiments disclose a method and an apparatus for increasing accuracy of an ultrasound diagnosis in a distant place by outputting an indicator related to telemedicine on the basis of the electronic device and the probe connected to the electronic device.

Technical Solution

In accordance with an aspect of the present disclosure, an electronic device is provided. The electronic device includes: a display; a camera; a first communication circuit for a connection to a probe; a second communication circuit for communication with at least one external device; and a processor electrically connected to the display, the camera, the first communication circuit, and the second communication circuit, wherein the processor is configured to detect an ultrasound diagnosis mode, execute the ultrasound diagnosis mode and establish communication with the external device in response to detection of the ultrasound diagnosis mode, acquire data in the ultrasound diagnosis mode, display the data through the display and transmit the data in a streaming type to the external device through the second communication circuit, and provide a control guide of the probe in response to reception of control information from the external device.

In accordance with another aspect of the present disclosure, an electronic device is provided. The electronic device includes: a display; a communication circuit for communication with an external device; and a processor electrically connected to the display and the communication circuit, wherein the processor is configured to establish communication with the external device, receive data in a streaming type from the external device, perform at least one of displaying the data and mirroring the data to an external screen, receive control information related to control of a probe connected to the external device based at least partially on the data, and transmit the control information to the external device.

In accordance with another aspect of the present disclosure, a method of operating an electronic device is provided. The method includes: detecting an ultrasound diagnosis mode; executing the ultrasound diagnosis mode and establishing communication with a configured external device in response to detection of the ultrasound diagnosis mode; acquiring data in the ultrasound diagnosis mode; displaying the data through a display and transmitting the data in a streaming type to the external device through a communication circuit; and providing a control guide of a probe in response to reception of control information from the external device.

In accordance with another aspect of the present disclosure, a method of operating an electronic device is provided. The method includes: establishing communication with an external device; receiving data in a streaming type from the external device; performing at least one of displaying the data and mirroring the data to an external screen; receiving control information related to control of a probe connected to the external device based at least partially on the data; and transmitting the control information to the external device.

In order to solve the technical problem, various embodiments of the present disclosure may include a computer-readable recording medium having a program recorded therein to perform the method by a processor.

Advantageous Effects

A method and an apparatus for performing an ultrasound diagnosis based on an electronic device according to various embodiments can perform a function of an ultrasound image diagnosis device through an electronic device and provide telemedicine according the function. According to various embodiments, it is possible to share a status of a patient in a distant place and an ultrasound diagnosis condition with a doctor in real time through a communication function or a camera function of the electronic device based on the connection between the electronic device and a probe, thereby making an accurate ultrasound diagnosis possible. According to various embodiments, in an emergency situation such as disaster or in emergency relief, and with a patient in a distant place, an accurate ultrasound diagnosis can be promoted through telemedicine with a medical specialist in a hospital. For example, an accurate status of the patient can be shared by transmitting, in real time, an ultrasound image and an affected part-photographing image to the medical specialist standing by in the hospital, and emergency treatment can be immediately performed when the patient is transported to the hospital.

According to various embodiments, patient diagnosis information can be easily shared using a wireless network within the electronic device and a camera function. According to various embodiments, communication in a distant place can be rapidly connected to a predetermined user or device within the hospital. According to various embodiments, an ultrasound image, a video call screen, and a probe guide indicator screen can be simultaneously provided through the electronic device or free screen switching can be provided.

BRIEF DESCRIPTION OF THE DRAWINGS

FIGS. 19A, 19B, and 19C are diagrams illustrating the operation of providing indicators for probe control guides according to various embodiments of the present disclosure;

FIG. 34 illustrates a menu configuration example in the electronic device according to various embodiments of the present disclosure;

MODE FOR CARRYING OUT THE INVENTION

Figure 1:
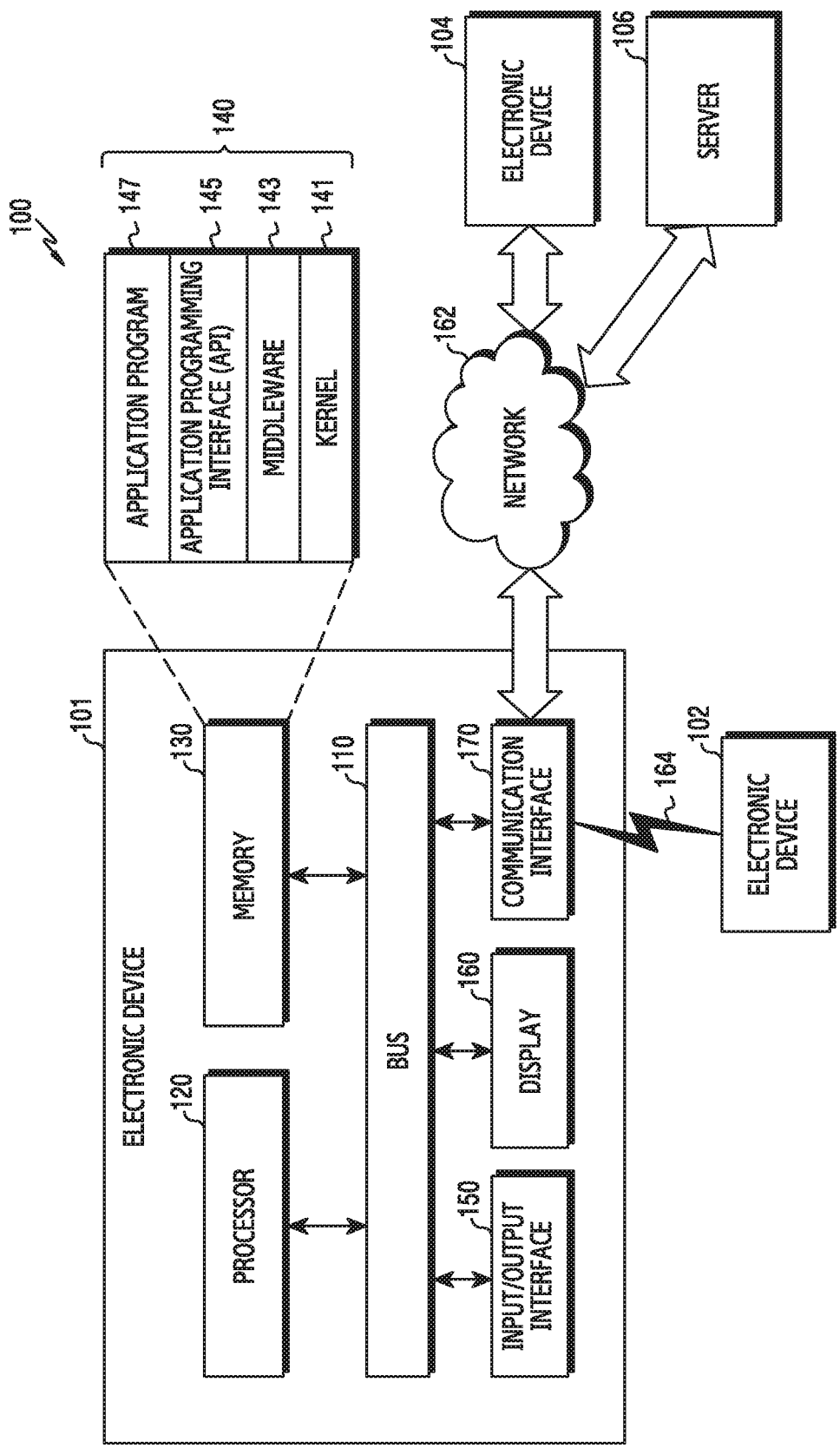
FIG. 1 illustrates a network environment including an electronic device according to various embodiments of the present disclosure.

Hereinafter, various embodiments of the present disclosure will be described with reference to the accompanying drawings. It should be appreciated that various embodiments of the present disclosure and the terms used therein are not intended to limit the technological features set forth herein to particular embodiments and include various modifications, equivalents, and/or alternatives for a corresponding embodiment. With regard to the description of the drawings, similar reference numerals may be used to refer to similar or related elements.

In the disclosure disclosed herein, the expressions "have," "may have," "include" and "comprise," or "may include" and "may comprise" used herein indicate existence of corresponding features (for example, elements such as numeric values, functions, operations, or components) and do not preclude the presence of additional features.

In the disclosure disclosed herein, the expressions "A or B," "at least one of A or/and B," or "one or more of A or/and B," and the like used herein may include any and all combinations of one or more of the associated listed items. For example, the term "A or B," "at least one of A and B," or "at least one of A or B" may refer to all of the case (1) where at least one A is included, the case (2) where at least one B is included, or the case (3) where both of at least one A and at least one B are included.

The terms, such as "first," "second," and the like used herein, may refer to various elements of various embodiments of the present invention, but do not limit the elements. For example, such terms do not limit the order and/or priority of the elements. Furthermore, such terms may be used to distinguish one element from another element. For example, "a first user device" and "a second user device" indicate different user devices regardless of the order or priority. For example, without departing from the scope of the present invention, a first element may be referred to as a second element, and similarly, a second element may be referred to as a first element.

It will be understood that when an element (for example, a first element) is referred to as being "(operatively or communicatively) coupled with/to" or "connected to" another element (for example, a second element), it can be directly coupled with/to or connected to another element or coupled with/to or connected to another element via an intervening element (for example, a third element). In contrast, when an element (for example, a first element) is referred to as being "directly coupled with/to" or "directly connected to" another element (for example, a second element), it should be understood that there is no intervening element (for example, a third element).

The expression "configured to" as used in various embodiments of the present disclosure may be interchangeably used with, for example, "suitable for", "having the capacity to", "designed to", "adapted to", "made to", or "capable of" in terms of hardware or software, according to circumstances. Alternatively, in some situations, the expression "device configured to" may mean that the device, together with other devices or components, "is able to". For example, the phrase "processor adapted (or configured) to perform A, B, and C" may mean a dedicated processor (e.g., embedded processor) only for performing the corresponding operations or a generic-purpose processor (e.g., Central Processing Unit (CPU) or Application Processor (AP)) that can perform the corresponding operations by executing one or more software programs stored in a memory device.

Terms used in the present invention are used to describe specified embodiments of the present invention and are not intended to limit the scope of other embodiments. The terms of a singular form may include plural forms unless otherwise specified. Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal way, unless expressly so defined herein in various embodiments of the present invention. In some cases, even if terms are terms which are defined in the specification, they may not be interpreted to exclude embodiments of the present invention An electronic device according to various embodiment of the present disclosure may include at least one of, for example, a smart phone, a tablet personal computer (PC), a mobile phone, a video phone, an electronic book reader (e-book reader), a desktop PC, a laptop PC, a netbook computer, a workstation, a server, a personal digital assistant (PDA), a portable multimedia player (PMP), a MPEG-1 audio layer-3 (MP3) player, a mobile medical device, a camera, or a wearable device, but is not limited thereto. The wearable device may include at least one of an accessory type (e.g., a watch, a ring, a bracelet, an anklet, a necklace, a glasses, a contact lens, or a head-mounted device (HMD)), a fabric or clothing integrated type (e.g., an electronic clothing), a body-mounted type (e.g., a skin pad or tattoo), and an implantable circuit, but is not limited thereto.

According to some embodiments, the electronic device may be a home appliance. The home appliance may include at least one of, for example, a television, a digital video disk (DVD) player, an audio player, a refrigerator, an air conditioner, a vacuum cleaner, an oven, a microwave oven, a washing machine, an air cleaner, a set-top box, a home automation control panel, a security control panel, a media box (e.g., Samsung HomeSync™, Apple TV™, or Google TV™), a game console (e.g., Xbox™ and PlayStation™), an electronic dictionary, an electronic key, a camcorder, or an electronic photo frame, but is not limited thereto.

According to other embodiment, the electronic device may include at least one of various medical devices (e.g., various portable medical measuring devices (a blood glucose monitoring device, a heart rate monitoring device, a blood pressure measuring device, a body temperature measuring device, etc.), a magnetic resonance angiography (MRA), a magnetic resonance imaging (MRI), a computed tomography (CT) machine, or an ultrasonic machine)), a navigation device, a global navigation satellite system (GNSS), an event data recorder (EDR), a flight data recorder (FDR), a vehicle infotainment devices, an electronic device for a ship (e.g., a navigation device for a ship, and a gyro-compass), avionics, security devices, an automotive head unit, a robot for home or industry, a drone, an automatic teller machine (ATM), a point of sales (POS) terminal, or an internet of things (IoT) device (e.g., a light bulb, various sensors, a sprinkler device, a fire alarm, a thermostat, a streetlamp, a toaster, a sporting good, a hot water tank, a heater, a boiler, etc.), but is not limited thereto.

According to an embodiment, the electronic device may include at least one of a part of furniture, a building/structure or a vehicle, an electronic board, an electronic signature receiving device, a projector, and various kinds of measuring instruments (e.g., a water meter, an electric meter, a gas meter, and a radio wave meter), but is not limited thereto. The electronic device according to an embodiment may be a flexible device. The electronic device may be a combination of one or more of the aforementioned various devices. The electronic device is not limited to the aforementioned devices and may include a new electronic device according to technological advance.

Hereinafter, various embodiments of the present disclosure will be described with reference to the accompanying drawings. As used herein, the term "user" may indicate a person who uses an electronic device or a device (e.g., an artificial intelligence electronic device) that uses an electronic device.

FIG. 1 illustrates a network environment including an electronic device according to various embodiments.

Referring to FIG. 1, an electronic device 101 in a network environment 100 is disclosed according to various exemplary embodiments. The electronic device 101 may include a bus 110, a processor 120, a memory 130, an input/output interface 150, a display 160, and a communication interface 170. In a certain exemplary embodiment, the electronic device 101 may omit at least one of the aforementioned constitutional elements or may additionally include other constitutional elements.

The bus 110 may include a circuit for connecting the aforementioned constitutional elements 110 to 170 to each other and for delivering communication (e.g., a control message and/or data) between the aforementioned constitutional elements.

The processor 120 may include one or more of a Central Processing Unit (CPU), an Application Processor (AP), and a Communication Processor (CP). The processor 120 may control, for example, at least one of other constitutional elements of the electronic device 101 and/or may execute an arithmetic operation or data processing for communication. The processing (or controlling) operation of the processor 120 according to various embodiments is described in detail with reference to the following drawings.

The memory 130 may include a volatile and/or non-volatile memory. The memory 130 may store, for example, a command or data related to at least one different constitutional element of the electronic device 101. According to various exemplary embodiments, the memory 130 may store a software and/or a program 140. The program 140 may include, for example, a kernel 141, a middleware 143, an Application Programming Interface (API) 145, and/or an application program (or an "application") 147, or the like. At least one part of the kernel 141, middleware 143, or API 145 may be referred to as an Operating System (OS). The memory 130 may include a computer-readable recording medium having a program recorded therein to perform the method according to various embodiment by the processor 120.

The kernel 141 may control or manage, for example, system resources (e.g., the bus 110, the processor 120, the memory 130, etc.) used to execute an operation or function implemented in other programs (e.g., the middleware 143, the API 145, or the application program 147). Further, the kernel 141 may provide an interface capable of controlling or managing the system resources by accessing individual constitutional elements of the electronic device 101 in the middleware 143, the API 145, or the application program 147.

The middleware 143 may perform, for example, a mediation role so that the API 145 or the application program 147 can communicate with the kernel 141 to exchange data.

Further, the middleware 143 may handle one or more task requests received from the application program 147 according to a priority. For example, the middleware 143 may assign a priority of using the system resources (e.g., the bus 110, the processor 120, or the memory 130) of the electronic device 101 to at least one of the application programs 147. For instance, the middleware 143 may process the one or more task requests according to the priority assigned to the at least one of the application programs, and thus may perform scheduling or load balancing on the one or more task requests.

The API 145 may include at least one interface or function (e.g., instruction), for example, for file control, window control, video processing, or character control, as an interface capable of controlling a function provided by the application 147 in the kernel 141 or the middleware 143.

For example, the input/output interface 150 may play a role of an interface for delivering an instruction or data input from a user or a different external device(s) to the different constitutional elements of the electronic device 101. Further, the input/output interface 150 may output an instruction or data received from the different constitutional element(s) of the electronic device 101 to the different external device.

The display 160 may include various types of displays, for example, a Liquid Crystal Display (LCD) display, a Light Emitting Diode (LED) display, an Organic Light-Emitting Diode (OLED) display, a MicroElectroMechanical Systems (MEMS) display, or an electronic paper display. The display 160 may display, for example, a variety of contents (e.g., text, image, video, icon, symbol, etc.) to the user. The display 160 may include a touch screen. For example, the display 160 may receive a touch, gesture, proximity, or hovering input by using a stylus pen or a part of a user's body.

The communication interface 170 may establish, for example, communication between the electronic device 101 and the external device (e.g., a 1st external electronic device 102, a 2nd external electronic device 104, or a server 106). For example, the communication interface 170 may communicate with the external device (e.g., the 2nd external electronic device 104 or the server 106) by being connected to a network 162 through wireless communication or wired communication.

For example, as a cellular communication protocol, the wireless communication may use at least one of Long-Term Evolution (LTE), LTE Advance (LTE-A), Code Division Multiple Access (CDMA), Wideband CDMA (WCDMA), Universal Mobile Telecommunications System (UMTS), Wireless Broadband (WiBro), Global System for Mobile Communications (GSM), and the like. Further, the wireless communication may include, for example, a near-distance communication 164. The near-distance communication 164 may include, for example, at least one of Wireless Fidelity (WiFi), Bluetooth, Near Field Communication (NFC), Global Navigation Satellite System (GNSS), and the like. According to a usage region or a bandwidth or the like, the GNSS may include, for example, at least one of Global Positioning System (GPS), Global Navigation Satellite System (Glonass), Beidou Navigation Satellite System (hereinafter, "Beidou"), Galileo, the European global satellite-based navigation system, and the like. Hereinafter, the "GPS" and the "GNSS" may be used interchangeably in the present document. The wired communication may include, for example, at least one of Universal Serial Bus (USB), High Definition Multimedia Interface (HDMI), Recommended Standard-232 (RS-232), power-line communication, Plain Old Telephone Service (POTS), and the like.

The network 162 may include, for example, at least one of a telecommunications network, a computer network (e.g., LAN or WAN), the internet, and a telephone network.

Each of the 1st and 2nd external electronic devices 102 and 104 may be the same type or different type of the electronic device 101. According to one exemplary embodiment, the server 106 may include a group of one or more servers. According to various exemplary embodiments, all or some of operations executed by the electronic device 101 may be executed in a different one or a plurality of electronic devices (e.g., the electronic device 102 or 104 or the server 106). According to one exemplary embodiment, if the electronic device 101 needs to perform a certain function or service either automatically or at a request, the electronic device 101 may request at least some parts of functions related thereto alternatively or additionally to a different electronic device (e.g., the electronic device 102 or 104 or the server 106) instead of executing the function or the service autonomously. The different electronic device (e.g., the electronic device 102 or 104 or the server 106) may execute the requested function or additional function, and may deliver a result thereof to the electronic device 101. The electronic device 101 may provide the requested function or service either directly or by additionally processing the received result. For this, for example, a cloud computing, distributed computing, or client-server computing technique may be used.

Figure 2:
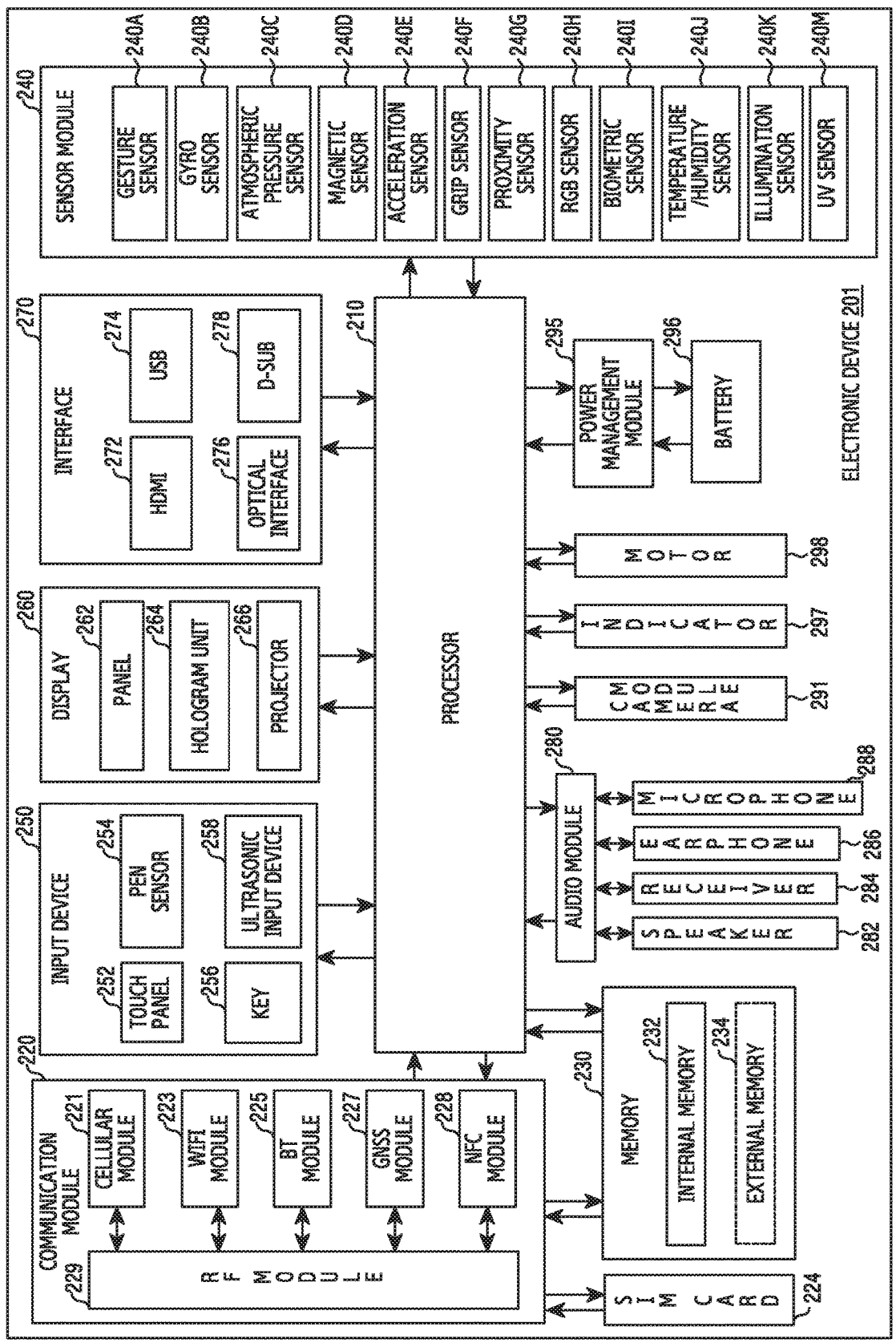
FIG. 2 is a block diagram of an electronic device according to various embodiments of the present disclosure.

FIG. 2 is a block diagram of an electronic device according to various exemplary embodiments.

An electronic device 201 may include, for example, all or some parts of the electronic device 101 of FIG. 1. The electronic device 201 may include one or more processors (e.g., Application Processors (APs)) 210, a communication module 220, a subscriber identity module 224, a memory 230, a sensor module 240, an input unit 250, a display 260, an interface 270, an audio module 280, a camera unit 291, a power management module 295, a battery 296, an indicator 297, and a motor 298.

The processor 210 may control a plurality of hardware or software constitutional elements connected to the processor 210 by driving, for example, an operating system or an application program, and may process a variety of data including multimedia data and may perform an arithmetic operation. The processor 210 may be implemented, for example, with a System on Chip (SoC). According to one exemplary embodiment, the processor 210 may further include a Graphic Processing Unit (GPU) and/or an Image Signal Processor (ISP). The processor 210 may include at least one part (e.g., a cellular module 221) of the aforementioned constitutional elements of FIG. 2. The processor 210 may process an instruction or data, which is received from at least one of different constitutional elements (e.g., a non-volatile memory), by loading it to a volatile memory and may store a variety of data in the non-volatile memory.

The communication module 220 may have a structure the same as or similar to the communication interface 170 of FIG. 1. The communication module 220 may include, for example, the cellular module 221, a Wi-Fi module 223, a BlueTooth (BT) module 225, a GNSS module 227 (e.g., a GPS module, a Glonass module, a Beidou module, or a Galileo module), a Near Field Communication (NFC) module 228, and a Radio Frequency (RF) module 229.

The cellular module 221 may provide a voice call, a video call, a text service, an internet service, or the like, for example, through a communication network. According to one exemplary embodiment, the cellular module 221 may identify and authenticate the electronic device 201 in the communication network by using the subscriber identity module (e.g., a Subscriber Identity Module (SIM) card) 224. According to one exemplary embodiment, the cellular module 221 may perform at least some functions that can be provided by the processor 210. According to one exemplary embodiment, the cellular module 221 may include a Communication Processor (CP).

Each of the WiFi module 223, the BT module 225, the GNSS module 227, or the NFC module 228 may include, for example, a processor for processing data transmitted/received via a corresponding module. According to a certain exemplary embodiment, at least some (e.g., two or more) of the cellular module 221, the WiFi module 223, the BT module 225, the GPS module 227, and the NFC module 228 may be included in one Integrated Chip (IC) or IC package.

The RF module 229 may transmit/receive, for example, a communication signal (e.g., a Radio Frequency (RF) signal). The RF module 229 may include, for example, a transceiver, a Power Amp Module (PAM), a frequency filter, a Low Noise Amplifier (LNA), an antenna, or the like. According to another exemplary embodiment, at least one of the cellular module 221, the WiFi module 223, the BT module 225, the GPS module 227, and the NFC module 228 may transmit/receive an RF signal via a separate RF module.

The subscriber identity module 224 may include, for example, a card including the subscriber identity module and/or an embedded SIM, and may include unique identification information (e.g., an Integrated Circuit Card IDentifier (ICCID)) or subscriber information (e.g., an International Mobile Subscriber Identity (IMSI)).

The memory 230 (e.g., the memory 130) may include, for example, an internal memory 232 or an external memory 234. The internal memory 232 may include, for example, at least one of a volatile memory (e.g., a Dynamic RAM (DRAM), a Static RAM (SRAM), a Synchronous Dynamic RAM (SDRAM), etc.) and a non-volatile memory (e.g., a One Time Programmable ROM (OTPROM), a Programmable ROM (PROM), an Erasable and Programmable ROM (EPROM), an Electrically Erasable and Programmable ROM (EEPROM), a mask ROM, a flash ROM, a flash memory (e.g., a NAND flash memory, a NOR flash memory, etc.), a hard drive, or a Solid State Drive (SSD)).

The external memory 234 may further include a flash drive, for example, Compact Flash (CF), Secure Digital (SD), Micro Secure Digital (Micro-SD), Mini Secure digital (Mini-SD), extreme Digital (xD), memory stick, or the like. The external memory 234 may be operatively and/or physically connected to the electronic device 201 via various interfaces.

The sensor module 240 may measure, for example, physical quantity or detect an operational status of the electronic device 201, and may convert the measured or detected information into an electric signal. The sensor module 240 may include, for example, at least one of a gesture sensor 240A, a gyro sensor 240B, a pressure sensor 240C, a magnetic sensor 240D, an acceleration sensor 240E, a grip sensor 240F, a proximity sensor 240G, a color sensor 240H (e.g., a Red, Green, Blue (RGB) sensor), a bio sensor 240I, a temperature/humidity sensor 240J, an illumination sensor 240K, an Ultra Violet (UV) sensor 240M, an ultrasonic sensor 240N, and an optical sensor 240P. According to one exemplary embodiment, the optical sensor 240P may detect light which is introduced basically according to exemplary embodiments of the present invention or reflected by an external object (e.g., a user's finger. etc.), and which is converted into a specific wavelength band by means of a light converting member. Additionally or alternatively, the sensor module 240 may include, for example, an E-nose sensor, an ElectroMyoGraphy (EMG) sensor, an ElectroEncephaloGram (EEG) sensor, an ElectroCardioGram (ECG) sensor, an Infrared (IR) sensor, an iris sensor, and/or a fingerprint sensor. The sensor module 240 may further include a control circuit for controlling at least one or more sensors included therein. In a certain exemplary embodiment, the electronic device 201 may further include a processor configured to control the sensor module 204 either separately or as one part of the processor 210, and may control the sensor module 240 while the processor 210 is in a sleep state.

The input device 250 may include, for example, a touch panel 252, a (digital) pen sensor 254, a key 256, or an ultrasonic input device 258. The touch panel 252 may recognize a touch input, for example, by using at least one of an electrostatic type, a pressure-sensitive type, and an ultrasonic type. In addition, the touch panel 252 may further include a control circuit. The touch penal 252 may further include a tactile layer and thus may provide the user with a tactile reaction.

The (digital) pen sensor 254 may be, for example, one part of a touch panel, or may include an additional sheet for recognition. The key 256 may be, for example, a physical button, an optical key, a keypad, or a touch key. The ultrasonic input device 258 may detect an ultrasonic wave generated from an input means through a microphone (e.g., a microphone 288) to confirm data corresponding to the detected ultrasonic wave.

The display 260 (e.g., the display 160) may include a panel 262, a hologram unit 264, or a projector 266. The panel 262 may include a structure the same as or similar to the display 160 of FIG. 1. The panel 262 may be implemented, for example, in a flexible, transparent, or wearable manner. The panel 262 may be constructed as one module with the touch panel 252. According to one exemplary embodiment, the panel 262 may include a pressure sensor (or a force sensor) capable of measuring strength of pressure for a user's touch. The pressure sensor may be implemented in an integral form with respect to the touch panel 252, or may be implemented as one or more sensors separated from the touch panel 252.

The hologram unit 264 may use an interference of light and show a stereoscopic image in the air. The projector 266 may display an image by projecting a light beam onto a screen. The screen may be located, for example, inside or outside the electronic device 201. According to one exemplary embodiment, the display 260 may further include a control circuit for controlling the panel 262, the hologram unit 264, or the projector 266.

The interface 270 may include, for example, a High-Definition Multimedia Interface (HDMI) 272, a Universal Serial Bus (USB) 274, an optical communication interface 276, or a D-subminiature (D-sub) 278. The interface 270 may be included, for example, in the communication interface 170 of FIG. 1. Additionally or alternatively, the interface 270 may include, for example, a Mobile High-definition Link (MHL) interface, a Secure Digital (SD)/Multi-Media Card (MMC) interface, or an Infrared Data Association (IrDA) standard interface.

The audio module 280 may bilaterally convert, for example, a sound and electric signal. At least some constitutional elements of the audio module 280 may be included in, for example, the input/output interface 150 of FIG. 1. The audio module 280 may convert sound information which is input or output, for example, through a speaker 282, a receiver 284, an earphone 286, the microphone 288, or the like.

The camera module 291 is, for example, a device for image and video capturing, and according to one exemplary embodiment, may include one or more image sensors (e.g., a front sensor or a rear sensor), a lens, an Image Signal Processor (ISP), or a flash (e.g., LED or xenon lamp).

The power management module 295 may manage, for example, power of the electronic device 201. According to one exemplary embodiment, the power management module 295 may include a Power Management Integrated Circuit (PMIC), a charger Integrated Circuit (IC), or a battery fuel gauge. The PMIC may have a wired and/or wireless charging type. The wireless charging type may include, for example, a magnetic resonance type, a magnetic induction type, an electromagnetic type, or the like, and may further include an additional circuit for wireless charging, for example, a coil loop, a resonant circuit, a rectifier, or the like. The battery gauge may measure, for example, residual quantity of the battery 296 and voltage, current, and temperature during charging. The battery 296 may include, for example, a rechargeable battery and/or a solar battery.

The indicator 297 may display a specific state, for example, a booting state, a message state, a charging state, or the like, of the electronic device 201 or one part thereof (e.g., the processor 210). The motor 298 may convert an electric signal into a mechanical vibration, and may generate a vibration or haptic effect. Although not shown, the electronic device 201 may include a processing device (e.g., a GPU) for supporting a mobile TV. The processing device for supporting the mobile TV may process media data conforming to a protocol of, for example, Digital Multimedia Broadcasting (DMB), Digital Video Broadcasting (DVB), Media-Flo™, or the like.

Each of constitutional elements described in the present document may consist of one or more components, and names thereof may vary depending on a type of an electronic device. The electronic device according to various exemplary embodiments may include at least one of the constitutional elements described in the present document. Some of the constitutional elements may be omitted, or additional other constitutional elements may be further included. Further, some of the constitutional elements of the electronic device according to various exemplary embodiments may be combined and constructed as one entity, so as to equally perform functions of corresponding constitutional elements before combination.

Figure 3:
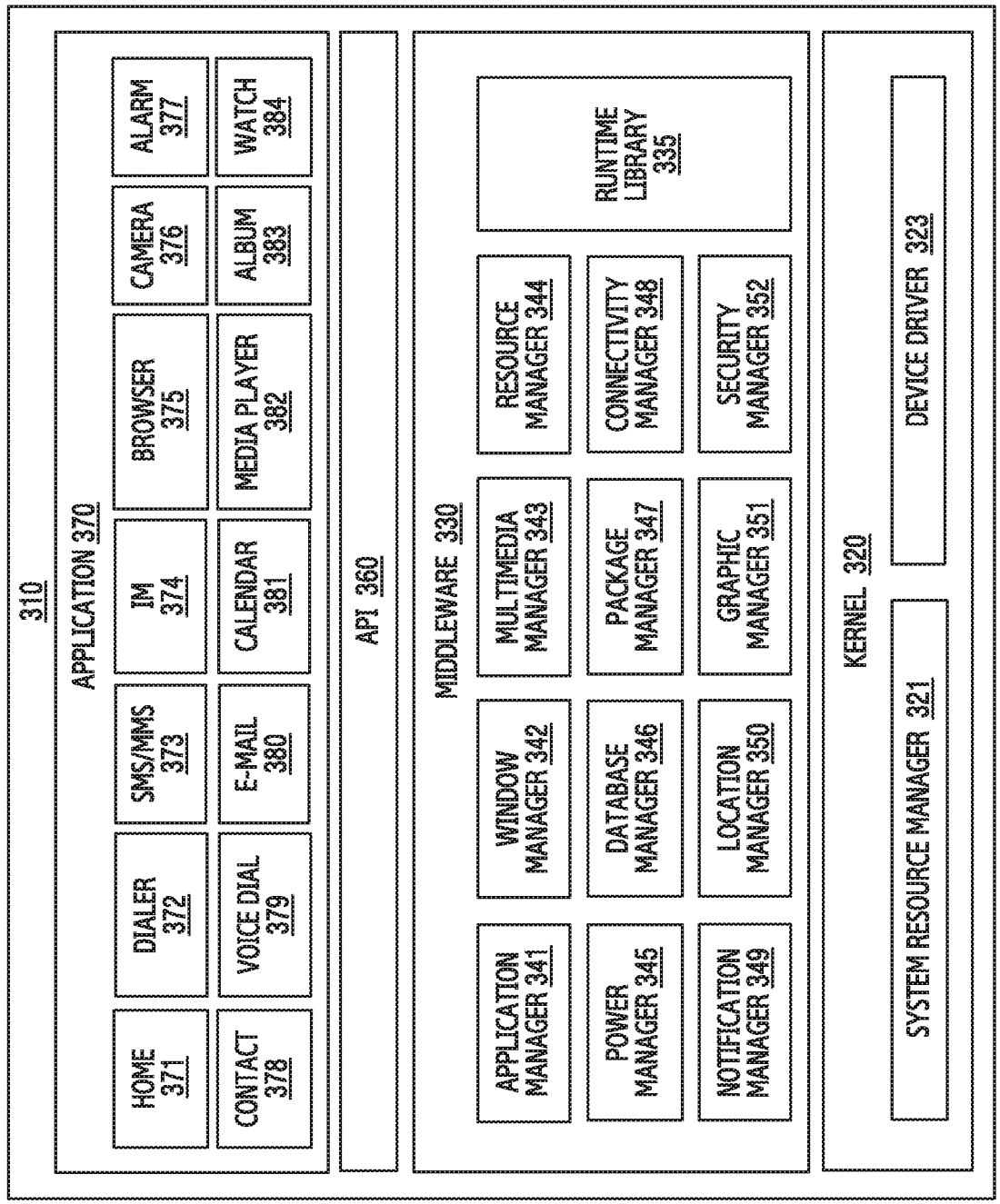
FIG. 3 is a block diagram of a program module according to various embodiments of the present disclosure.

FIG. 3 is a block diagram of a program module according to various embodiments of the present disclosure.

According to an embodiment, a program module 310 (e.g., the program 140) can include an OS for controlling a resource relating to an electronic device (e.g., the electronic device 101) and/or various applications (e.g., the application program 147) running on the OS.

The program module 310 includes a kernel 320, a middleware, an API 360, and an application 370. At least part of the program module 310 can be preloaded on an electronic device or can be downloaded from an external electronic device (e.g., the electronic devices 102, 104, or the server 106).

The kernel 320 includes, for example, at least one of a system resource manager 321 and a device driver 323. The system resource manager 321 can control, allocate, or retrieve a system resource. According to an embodiment, the system resource manager 321 can include a process management unit, a memory management unit, or a file system management unit. The device driver 323 can include, for example, a display driver, a camera driver, a Bluetooth driver, a sharing memory driver, a USB driver, a keypad driver, a WiFi driver, an audio driver, or an inter-process communication (IPC) driver.

The middleware 330, for example, can provide a function commonly required by the application 370, or can provide various functions to the application 370 through the API 360 in order to allow the application 370 to efficiently use a limited system resource inside the electronic device. The middleware 330 includes at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 can include, for example, a library module used by a complier to add a new function through a programming language while the application 370 is running. The runtime library 335 can manage input/output, manage memory, or arithmetic function processing.

The application manager 341, for example, can manage the life cycle of the applications 370. The window manager 342 can manage a GUI resource used in a screen. The multimedia manager 343 can recognize a format for playing various media files and encode or decode a media file by using the codec in a corresponding format. The resource manager 344 can manage a source code of the application 370 or a memory space.

The power manager 345 can manage the capacity or power of the battery and provide power information for an operation of the electronic device. The power manager 345 can operate together with a basic input/output system (BIOS). The database manager 346 can create, search, or modify a database used in the application 370. The package manager 347 can manage installation or updating of an application distributed in a package file format.

The connectivity manger 348 can manage, for example, a wireless connection. The notification manager 349 can provide an event, such as incoming messages, appointments, and proximity alerts, to the user. The location manager 350 can manage location information of an electronic device. The graphic manager 351 can manage a graphic effect to be provided to the user or a user interface relating thereto. The security manager 352 can provide, for example, system security or user authentication. The middleware 330 can include a telephony manager for managing a voice or video call function of the electronic device.

The middleware 330 can include a middleware module for combining various functions of the above-described components. The middleware 330 can provide a module specialized for each type of OS. The middleware 330 can dynamically delete part of the existing components or add new components.

The API 360 (e.g., the API 145), as a set of API programming functions, can be provided as another configuration according to the OS. For example, one API set can be provided for each platform, or two or more API sets can be provided for each platform.

The application 370 includes at least one of a home 371, a dialer 372, an SMS/multimedia messaging system (MMS) 373, an instant message (IM) 374, a browser 375, a camera 376, an alarm 377, a contact 378, a voice dial 379, an e-mail 380, a calendar 381, a media player 382, an album 383, a clock 384, health care (e.g., measure an exercise amount or blood sugar level), or environmental information (e.g., air pressure, humidity, or temperature information) provision application.

According to an embodiment, the application 370 can include an information exchange application for supporting information exchange between the electronic device and an external electronic device. The information exchange application can include, for example, a notification relay application for relaying specific information to the external device or a device management application for managing the external electronic device.

For example, the notification relay application can relay notification information from another application of the electronic device to an external electronic device, or receive and forward notification information from an external electronic device to the user.

The device management application, for example, can install, delete, or update a function (e.g., turn-on/turn off of the external electronic device itself (or some components) or display brightness (or resolution) adjustment) of an external electronic device communicating with the electronic device, or an application operating in the external electronic device.

According to an embodiment, the application 370 can include a specified application (e.g., a health care application of a mobile medical device, an acoustical measurement application, or an audio playback application) according to a property of the external electronic device. According to an embodiment, the application 370 can include an application received from an external electronic device (e.g., the server 106 or the electronic device 102, 104). According to an embodiment, the application 370 can include a preloaded application or a third party application downloadable from the server.

According to an embodiment, at least part of the program module 310 can be implemented with software, firmware, hardware (e.g., the processor 210), or a combination of at least two of them. At least part of the program module 310 can be implemented (e.g., executed) by the processor (e.g., the processor 210). At least part of the program module 310 can include a module, a program, a routine, a set of instructions, or a process for executing one or more functions.

The term "module", as used herein, can imply a unit including hardware, software, and firmware, or any suitable combination. The term "module" can be interchangeably used with terms such as "unit", "logic", "logical block", "component", "circuit", and the like. A module can be a minimum unit of an integral component or can be a part thereof. A module can be a minimum unit for performing one or more functions or may be a part thereof. A module can be mechanically or electrically implemented. For example, a module can include at least one of an application-specific integrated circuit (ASIC) chip, a field programmable gate arrays (FPGAs), and a programmable-logic device, which are known or will be developed, and which perform certain operations.

At least some parts of a device (e.g., modules or functions thereof) or a method (e.g., operations), based on embodiments of the present disclosure, can be implemented with an instruction stored in a non-transitory computer-readable storage medium as a program module. When the instruction is executed by a processor (e.g., the processor 120), the processor can perform a function corresponding to the instruction. The non-transitory computer-readable storage medium can be, for example, the memory 130.

The non-transitory computer readable recording medium can include, for example, a hard disk, a floppy disc, a magnetic medium (e.g., a magnetic tape), an optical storage medium (e.g., a compact disc-ROM (CD-ROM) or a DVD, a magnetic-optic medium (e.g., a floptical disc)), and an internal memory. The instruction can include code created by a compiler or code executable by an interpreter. The hardware device described above may be configured to operate as one or more software modules to perform the operations of the various embodiments, and vice versa.

According to various embodiments, at least a portion of the program module 310 can further include at least one or more components among the aforementioned components, or can omit some of them, or can further include additional other components. Operations performed by a module, program module, or other components of the various embodiments of the present disclosure can be executed in a sequential, parallel, repetitive, or heuristic manner. In addition, some of the operations can be executed in a different order or may be omitted, or other operations may be added. Embodiments disclosed in the present invention are suggested for easy explanation and understanding of the technical features disclosed herein and are not intended to limit the scope of various embodiments of the present invention. Therefore, the scope of various embodiments of the present invention should be interpreted as including all changes based on the technical idea of various embodiments of the present invention or various other embodiments.

Embodiments (for example, including a camera function) of the present disclosure relate to a method and an apparatus for performing an ultrasound diagnosis based on an electronic device. According to various embodiments, a telemedicine and a remote treatment can be provided using a mobile ultrasound. According to various embodiments, it is possible to share a status of a user with and diagnose a status of a user by a medical specialist in a hospital, by transmitting a status of a patient in a distant place and an ultrasound diagnosis condition in real time through a communication function or a camera function of the electronic device.

The electronic device according to various embodiments of the present disclosure can include any device that supports a communication function and/or a camera function and uses one or more or a variety of processors, such as an application processor (AP), an communication processor (CP), an graphic processing unit (GPU), or an central processing unit (CPU). For example, the electronic device according to various embodiments can include any information communication device, multimedia device, wearable device, internet of things (IoT) device, or listening device that supports a communication function and/or a camera function, or an application device therefor.

Hereinafter, an operation method and a device according to various embodiments of the present disclosure will be described with reference to the accompanying drawings. However, it should be noted that the various embodiments of the present disclosure are not limited by the following description, and thus it can be applied to various embodiments based on the following embodiments. Hereinafter, various embodiments of the present disclosure will be described based on a hardware approach. However, various embodiments of the present disclosure include a technology that uses both hardware and software, and thus, the various embodiments of the present disclosure may not exclude the perspective of software.

Figure 4:
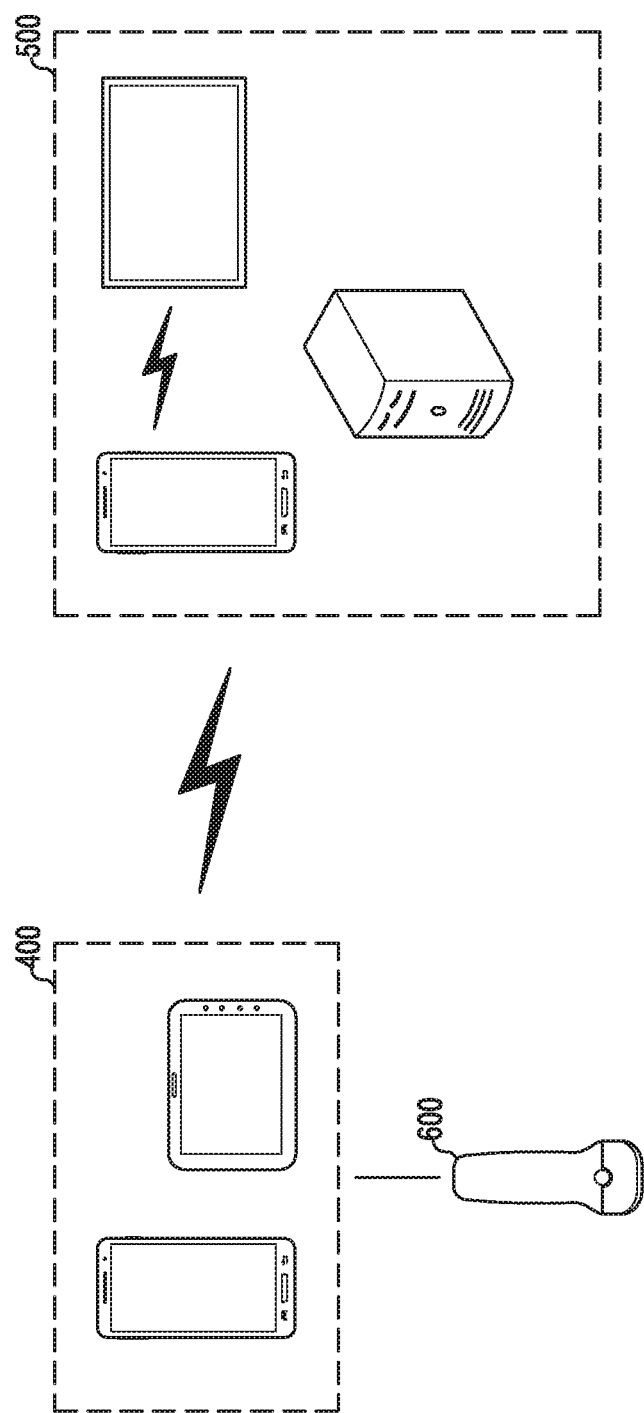
FIG. 4 is a block diagram schematically illustrating the configuration of an electronic device according to an embodiment of the present disclosure.

FIG. 4 illustrates a system according to various embodiments of the present disclosure.

Referring to FIG. 4, a system according to various embodiments of the present disclosure may include a first electronic device 400, a probe 600, and a second electronic device 500.

According to various embodiments, the first electronic device 400 may be connected (for example, paired) with the probe 600 through first communication (for example, wired communication or wireless communication) and connected with the second electronic device 500 through second communication (for example, wireless communication). According to various embodiments, the first communication may include a wired communication scheme such as cable communication or a short-range wireless communication scheme such as BT, BLE, or Near-Field Magnetic Induction (NFMI). According to various embodiments, the first communication is not limited thereto and may include various wireless communication, for example, Wi-Fi, NFC, ZigBee, UWB, or IrDA. According to various embodiments, the second communication may include a mobile communication scheme such as cellular communication or a wireless communication scheme such as Wi-Fi.

According to various embodiments, the first electronic device 400 may acquire first data (for example, ultrasound scan data) by the connected probe 600 and display the acquired first data (for example, ultrasound scan image). According to various embodiments, the first electronic device 400 may acquire second data (for example, affected part image data) photographed by an internal camera and display the acquired second data (for example, a preview image). According to various embodiments, the first electronic device 400 may display the first data and the second data together on split screens or independently display the first data and the second data on an entire screen. According to various embodiments, the first electronic device 400 may transmit at least one piece of the first data acquired from the probe 600 and the second data acquired from the camera to the second electronic device 500 in a distant place.

According to various embodiments, the first electronic device 400 may include, for example, a smart phone and a tablet Personal Computer (PC). According to various embodiments, the first electronic device 400 may display various User Interfaces (UIs) or Graphical User Interfaces (GUIs) related to telemedicine using the probe 600. The operation and relevant screen examples of the first electronic device 400 according to various embodiments will be described in detail with reference to the drawings below. According to various embodiments, the probe 600 may include, for example, an ultrasound probe. According to various embodiments, the probe 600 may be connected to the first electronic device 400, and may generate ultrasound scan data and provide the generated ultrasound scan data to the first electronic device 400. The probe 600 may radiate an ultrasound signal from a body surface of a target to a desired part within the body and acquire a tomogram of soft tissues or an image of a blood flow based on information of the reflected ultrasound signal (for example, an ultrasound echo signal). Examples of the operation using the probe 600 according to various embodiments will be described in detail with reference to the drawings below.

According to various embodiments, the second electronic device 500 may include an external device located in a distance place, for example, another electronic device, an external screen (for example, a monitor, a TV, or a large screen), and a server (for example, a computer). According to various embodiments, the second electronic device 500 may be connected to the first electronic device 400 through wireless communication and may receive data (for example, ultrasound scan data) from the first electronic device 400 in real time. According to various embodiments, the second electronic device 500 may display various UIs or GUIs related to a telemedicine based at least partially on the received data.

According to various embodiments, the second electronic device 500 may generate various pieces of remote control information related to the telemedicine based at least partially on the received data and transmit the generated control information to the first electronic device 400. According to various embodiments, the second electronic device 500 may be connected to another device in a distant place and share (for example, screen mirroring) data received from the first electronic device 400. According to an embodiment, it may be assumed that the second electronic device 500 corresponds to a smart phone and a monitor, and the smart phone and the monitor exist in the same space (for example, within a radius of short-range communication). While the smart phone receives data from the first electronic device 400 and displays the received data through the smart phone, the smart phone may share and display the data through the connected monitor based on screen mirroring. The operation and relevant screen examples of the second electronic device 500 according to various embodiments will be described in detail with reference to the drawings below.

Figure 5:
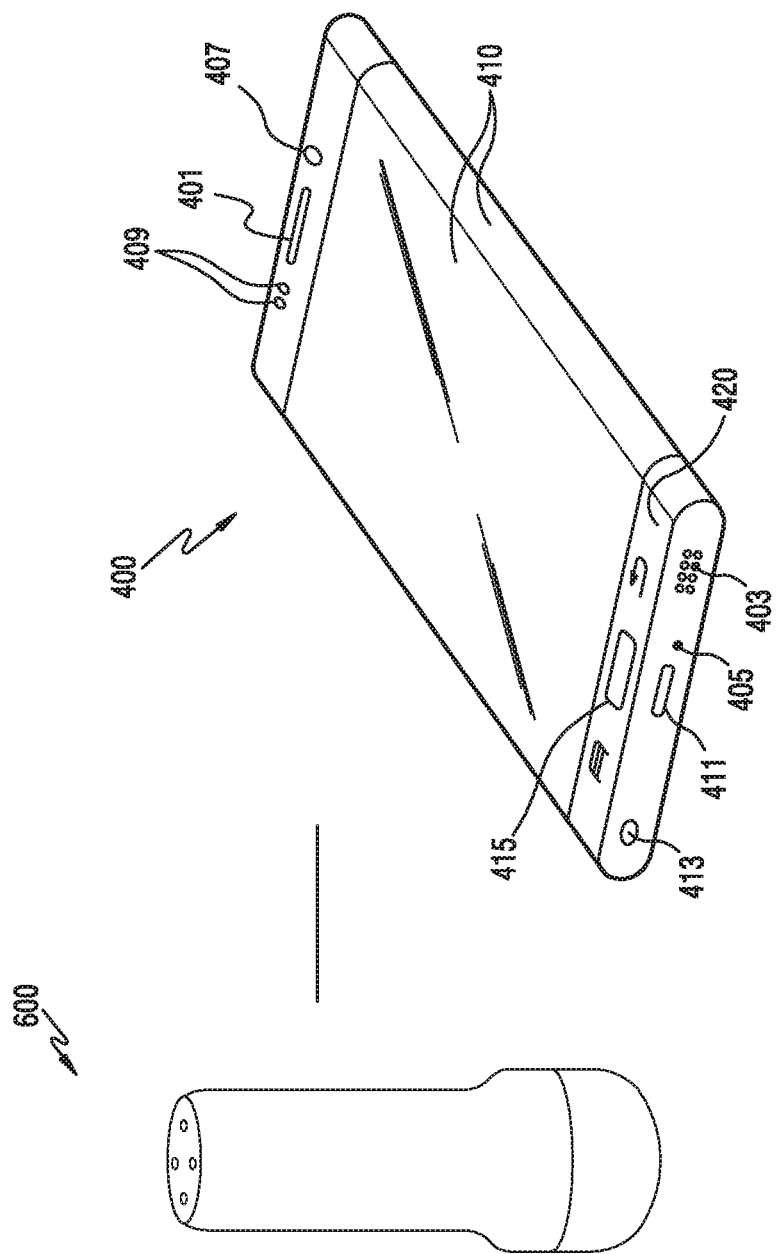
FIG. 5 illustrates an electronic device and a probe according to various embodiments of the present disclosure.

FIG. 5 illustrates an electronic device and a probe according to various embodiments of the present disclosure.

Referring to FIG. 5, FIG. 5 illustrates the first electronic device 400 as an example and the connection between the first electronic device 400 and the probe based on wireless communication as an example.

According to various embodiments, the electronic device 400 may include a display 410, a housing (or a body) 420 to which the display 410 is coupled while the display 410 is seated therein, and an additional device formed on the housing 420 to perform the function of the electronic device 400. According to various embodiments, the additional device may include a first speaker 401, a second speaker 403, a microphone 405, sensors (for example, a front camera module 407 and an illumination sensor 409), communication interfaces (for example, a charging or data input/output port 411 and an audio input/output port 413), and a button 415. According to various embodiments, when the electronic device 400 and the probe 600 are connected through a wired communication scheme, the electronic device 400 and the probe 600 may be connected based on at least some ports (for example, the data input/output port 411) of the communication interfaces.

According to various embodiments, the display 410 may include a flat display or a bended display (or a curved display) which can be folded or bent through a paper-thin or flexible substrate without damage. The bended display may be coupled to the housing 420 to remain in a bent form. According to various embodiments, the electronic device 400 may be implemented as a display device, which can be quite freely folded and unfolded such as a flexible display, including the bended display. According to various embodiments, in a Liquid Crystal Display (LCD), a Light Emitting Diode (LED) display, an Organic LED (OLED) display, or an Active Matrix OLED (AMOLED) display, the display 410 may replace a glass substrate surrounding liquid crystal with a plastic film to assign flexibility to be folded and unfolded.

According to various embodiments, the electronic device 400 may be connected to the probe 600. According to various embodiments, the electronic device 400 may be connected to the probe 600 based on wireless communication (for example, Bluetooth or Bluetooth Low Energy (BLE)).

According to various embodiments, the electronic device 400 may be connected to the probe 600, and may generate relevant data (for example, ultrasound scan data or affected part image data) for remote treatment and transmit the generated data to the second electronic device 500 in a distant place. According to various embodiments, when detecting the connection with the probe 600, the electronic device 400 may recognize an emergent diagnosis start and enter an emergency mode. In response to the entrance into the emergency mode, the electronic device 400 may omit a preset step and immediately execute an emergency preset. This will be described in detail with reference to the drawings below.

According to various embodiments, the electronic device 400 may process an operation related to starting a diagnosis (for example, acquire ultrasound data by controlling the probe 600) using the probe 600 and displaying and transmitting the diagnosis result (for example, ultrasound data) to the second electronic device 500 in a distant place.

According to various embodiments, the electronic device 400 may receive remote control information (for example, an ultrasound diagnosis guide, an emergency treatment guide, and a probe 600 control guide) from the second electronic device 500 and perform various operations (for example, displaying a guide, outputting an indicator, or controlling the probe 600 for outputting the indicator) related to the remote control information. According to various embodiments, various examples related to the electronic device 400 supporting the remote treatment linking with the probe 600 will be described in detail with reference to the drawings below.

According to various embodiments, the probe 600 may be connected to the electronic device 600 through wireless communication. The probe 600 may radiate, for example, an ultrasound signal generated from a transducer to a target (examinee), receive information of an echo signal reflected from the target, and acquire an image of a part inside the target. For example, the probe 600 may be used for a medical purpose such as observing the inside of the target, detecting a foreign material, and assessing an injury. The probe 600 may transmit the acquired image to the connected electronic device 400.

According to various embodiments, the probe 600 may output an indicator related to a probe control guide or a diagnosis guide based on the control of the electronic device 400. According to an embodiment, the probe 600 may operate to output lighting through an included output unit (for example, an LED or an infrared ray as a light emission device). According to various embodiments, various examples related to the electronic device 400 supporting the remote treatment linking with the probe 600 will be described in detail with reference to the drawings below.

Figure 6:
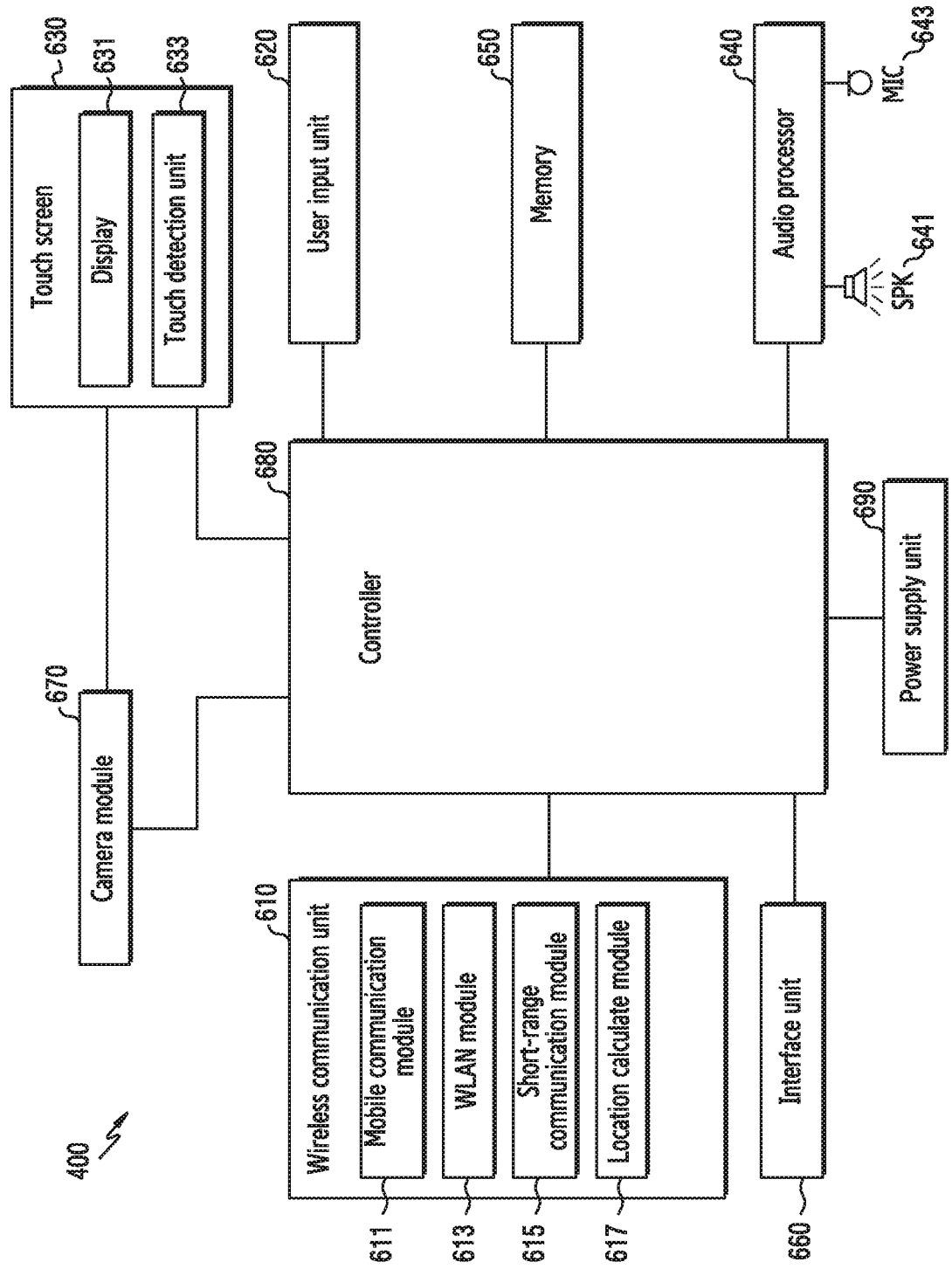
FIG. 6 schematically illustrates the configuration of an electronic device according to various embodiments of the present disclosure.

FIG. 6 schematically illustrates the configuration of an electronic device according to various embodiments of the present disclosure.

Referring to FIG. 6, the electronic device 400 according to various embodiments of the present disclosure may include, for example, a wireless communication unit 610, a user input unit 620, a touch screen 830, an audio processor 640, a memory 650, an interface unit 660, a camera module 670, a controller 680 (for example, the processor 120), and a power supply unit 690. According to various embodiments of the present disclosure, the electronic device 400 may include more or fewer elements than the elements of FIG. 6, since the elements of FIG. 6 are not essential.

The wireless communication unit 610 may have, for example, the configuration which the same as or similar to that of the communication module 220 of FIG. 2. The wireless communication unit 610 may include one or more modules for enabling wireless communication between the electronic device 400 and other external devices (for example, the probe 600, another electronic device 500, and the server 106). For example, the wireless communication unit 610 may include a mobile communication module 611, a Wireless Local Area Network (WLAN) module 613, a short range communication module 615, and a location calculation module 617. According to various embodiments, the wireless communication unit 610 may include modules (for example, a short-range communication module and a long-distance communication module) for communicating with neighboring external devices.

The mobile communication module 611 may have, for example, the configuration which is the same as or similar to the cellular module 221 of FIG. 2. The mobile communication module 611 may transmit/receive a wireless signal to/from at least one of a base station, an external electronic device (for example, another electronic device 104), and various servers (for example, an application server, a management server, an integration server, a provider server, a content server, an Internet server, a cloud server, and the like) over a mobile communication network. The wireless signal may include a voice signal, a data signal, or various forms of control signal. The mobile communication module 611 may transmit various pieces of data required for the operation of the electronic device 400 to the external electronic device (for example, the server 106 or another electronic device 104) in response to a request from the user.

The WLAN module 613 may have, for example, the configuration which is the same as or similar to that of the Wi-Fi module 223 of FIG. 2. The WLAN module 613 may indicate a module for establishing wireless Internet access and a WLAN link with another external device (for example, the probe 600, another electronic device 102, or the server 106). The WLAN module 613 may be installed inside or outside the electronic device 400. Wireless Internet technology may include Wi-Fi, Wireless broadband (Wibro), World interoperability for Microwave access (WiMax), High Speed Downlink Packet Access (HSDPA), millimeter Wave (mmWave), or the like. The WLAN module 613 may transmit or receive various pieces of data of the electronic device 400 to or from the outside by linking with another external device (for example, the probe 600 or another electronic device 104) connected to the electronic device 400 through a network (for example, a wireless Internet network (for example, the network 162)). The WLAN module 613 may always maintain an on-state, or may be turned on based on settings of the electronic device 400 or user input.

The short-range communication module 615 may be a module for performing short-range communication. Bluetooth, Bluetooth Low Energy (BLE), Radio Frequency Identification (RFID), Infrared Data Association (IrDA), Ultra Wideband (UWB), ZigBee, Near Field Communication (NFC), or the like may be used as a short-range communication technology. The short-range communication module 615 may transmit or receive various pieces of data of the electronic device 400 to or from the external device by linking with another external device (for example, the probe 600) connected to the electronic device 400 through a network (for example, a short-range communication network). The short-range communication module 615 may always maintain an on-state, or may be turned on based on settings of the electronic device 400 or user input.

The location calculation module 617 may have, for example, the configuration which is the same as or similar to that of the GNSS module 227 of FIG. 2. The location calculation module 617 is a module for obtaining a location of the electronic device 400, and may include a Global Location System (GPS) module as a representative example. The location calculation module 617 may measure the location of the electronic device 400 based on the principle of triangulation.

The user input unit 620 may generate input data for controlling the operation of the electronic device 400 in response to user input. The user input unit 620 may include at least one input device for detecting various user inputs. For example, the user input unit 620 may include a keypad, a dome switch, a physical button, a touch pad (resistive type/capacitive type), a jog & shuttle, and a sensor (for example, the sensor module 240).

Some parts of the user input unit 620 may be implemented in a button form on an outer region of the electronic device 400, or some or all parts of the user input unit 620 may also be implemented as a touch panel. The user input unit 620 may receive user input for initiating the operation (for example, a function of connecting to or recognizing the probe 600, an ultrasound diagnosis function, and a data transmission/reception function) of the electronic device 400 according to various embodiments of the present disclosure and generate an input signal according to user input. The touch screen 630 may indicate an input/output device, which can simultaneously perform an input function and a display function, and may include a display 631 (for example, the display 160 or 260) and a touch detection unit 633. The touch screen 630 may provide an input/output interface between the electronic device 400 and the user, transfer a user's touch input to the electronic device 400, and serve as a medium that shows an output from the electronic device 400 to the user. The touch screen 630 may show a visual output to the user. The visual output may be shown in a form of text, graphics, video, and a combination thereof.

The display 631 may display (output) various pieces of information processed by the electronic device 400. For example, the display 631 may display a User Interface (UI) or a Graphical UI (GUI) related to an operation of the electronic device 400 for connecting to the probe 600, an operation of the electronic device 400 for displaying data (for example, ultrasound scan data or affected part image data) of the probe 600, an operation of the electronic device 400 for displaying a guide related to telemedicine/remote treatment based at least partially on data, and an operation of the electronic device 400 for performing communication (for example, image communication or data communication) with another connected electronic device. Various types of displays (for example, the display 160) may be used for the display 631. According to various embodiments, a bended display may be used for the display 631.

The touch detection unit 633 may be seated on the display 631 and detect user input in contact with or in proximity to the surface of the touch screen 630. The user input may include touch input or proximity input made based on at least one of a single touch, a multi-touch, hovering, and an air gesture. According to various embodiments, the touch detection unit 633 may receive user input for initiating an operation related to the use of the electronic device 400 and generate an input signal according to the user input.

The audio processor 640 may have, for example, the configuration, which is the same as or similar to the audio module 280 of FIG. 2. The audio processor 640 may transmit, to a speaker (SPK) 841, an audio signal input from the controller 680, and may perform a function of transferring an audio signal such as a voice input from a microphone (MIC) 843 to the controller 680. The audio processor 640 may convert voice/sound data into an audible sound and output the audible sound through the speaker 641 under the control of the controller 680, and may convert an audio signal, such as a voice, received from the microphone 643 into a digital signal and transfer the digital signal to the controller 680.

The speaker 641 may output audio data received from the wireless communication unit 610 or stored in the memory 650. The speaker 641 may output sound signals related to various operations (functions) performed by the electronic device 400.

The microphone 643 may receive an external sound signal and process the sound signal into electric voice data. Various noise reduction algorithms may be implemented in the microphone 643 to remove noise generated in the process of receiving an external sound signal. The microphone 643 may serve to input audio streaming such as a voice command (for example, a voice command for initiating a function of executing an emergency mode or connecting to another electronic device).

The memory 650 (for example, the memory 130 or 230) may store one or more programs executed by the controller 680 and also perform a function of temporarily storing input/output data. The input/output data may include, for example, videos, images, photos, or audio files and also include ultrasound images of the probe 600. The memory 650 may serve to store acquired data, and may store data acquired in real time in a temporary storage device and data, which is decided to be stored, in a storage device which can store the data for a long time.

According to various embodiments, the memory 650 may store one or more programs, data, or instructions related to the controller 680 (for example, the processor) for detecting an ultrasound diagnosis mode, executing the ultrasound diagnosis mode in response to the detection of the ultrasound diagnosis mode, establishing communication with an external device (for example, the second electronic device 500 or an external screen), acquiring data in the ultrasound diagnosis mode, displaying the data through a display, transmitting the data streaming through a communication circuit, and providing a control guide of the probe 600 in response to reception of control information from the external device.

According to various embodiments, the memory 650 may store one or more programs, data, or instructions related to the controller 680 (for example, the processor) for establishing communication with the external device (for example, the first electronic device 400), receiving data streaming from the external device, performing at least one of displaying the data and mirroring the data to an external screen, receiving control information related to the control of the probe 600 connected to the external device based at least partially on the data, and transmitting the control information to the external device.

The memory 650 may include one or more application modules (or software modules).

The interface unit 660 may have, for example, the configuration which is the same as or similar to the interface 270 of FIG. 2. The interface unit 660 may receive data or power from another electronic device and transmit the received data or power to each element within the electronic device 400. The interface unit 660 may transmit data within the electronic device 400 to another electronic device. For example, the interface unit 660 may include a wired/wireless headset port, an external charger port, a wired/wireless data port, a memory card port, an audio input/output port, a video input/output port, an earphone port, and the like. According to various embodiments, when the electronic device 400 and the probe 600 are connected through a wired communication scheme, they may be connected to each other based at least partially on the interface unit 600.

The camera module 670 (for example, the camera module 291) indicates the configuration of supporting a photographing function of the electronic device 400. The camera module 670 may photograph a certain subject under the control of the controller 680 and transfer the photographed data (for example, image) to the display 631 and the controller 680.

The controller 680 (for example the processor or a control circuit) may control the overall operation of the electronic device 400. According to various embodiments, the controller 680 may have, for example, the configuration which is the same as or similar to the processor 210 of FIG. 2.

According to various embodiments, when the electronic device 400 operates as the first electronic device, the controller 680 may process the operation of detecting the ultrasound diagnosis mode, the operation of executing the ultrasound diagnosis mode and establishing communication with an external device (for example, the second electronic device 500 or an external screen) in response to the detection of the ultrasound diagnosis mode, the operation of acquiring data in the ultrasound diagnosis mode, the operation of displaying the data through a display and transmitting the data streaming through a communication circuit, and the operation of providing a control guide of the probe 600 in response to reception of control information from the external device.

According to various embodiments, when the electronic device 400 operates as the second electronic device, the controller 680 may process the operation of establishing communication with an external device (for example, the first electronic device 400), the operation of receiving data streaming from the external device, the operation of performing at least one of displaying the data and mirroring the data to an external screen, the operation of receiving control information related to the control of the probe 600 connected to the external device based at least partially on the data, and the operation of transmitting the control information to the external device.

The controller 680 may include one or more processors for controlling the operation of the electronic device 400. According to various embodiments, the controller 680 may control the operation of hardware modules such as the audio processor 640, the interface unit 660, the display 631, and the camera module 670. The control operation of the controller 680 according to various embodiments of the present disclosure will be described in detail with reference to the drawings below. According to various embodiments of the present disclosure, the controller 680 may be implemented as one or more processors for controlling the operation of the electronic device 400 according to various embodiments of the present disclosure by executing one or more programs stored in the memory 650.

The power supply unit 690 may receive external power and internal power and supply power required for operating the elements under the control of the controller 680. According to various embodiments of the present disclosure, the power supply unit 690 may supply or block (on/off) power to the wireless communication unit 610, the display 631, and the camera module 670 by the control of the controller 680.

According to various embodiments, although the configuration of the second electronic device 500 is not illustrated, the second electronic device 500 may have the configuration, which is the same as or similar to that of the electronic device 400 of FIG. 6, and the first electronic device 400 and the second electronic device 500 may be implemented as the same device (for example, smart phone: smart phone, or tablet PC: tablet PC) or different devices (for example, smart phone: tablet PC, tablet PC: smart phone, or smart phone: external screen (TV or monitor).

As described above, the electronic device 400 according to various embodiments of the present disclosure may include the display (for example, the display 631), the touch screen 630, the camera (for example, the camera module 670), a first communication circuit (for example, the wireless communication unit 610 and the interface unit 660) for connecting to the probe 600, a second communication circuit (for example, the wireless communication unit 810) for communication with at least one external device (for example, the second electronic device 500 and an external screen), and the processor (for example, the controller 680) electrically connected to the display, the camera, the first communication circuit, and the second communication circuit, and the processor may be configured to detect an ultrasound diagnosis mode, execute the ultrasound diagnosis mode and establish communication with the external device in response to the detection of the ultrasound diagnosis mode, acquire data in the ultrasound diagnosis mode, display the data through the display and transmit data streaming to the external device through the second communication circuit, and provide a control guide of the probe in response to reception of control information (for example, guide information) from the external device.

According to various embodiments, the processor may be configured to acquire first data (for example, an ultrasound image or ultrasound scan data) photographed through the probe 600, acquire second data (for example, a probe control image or affected part image data) photographed through the camera, display at least one of the first data and the second data through a preset scheme, and transmit the first data and the second data to the external device.

According to various embodiments, the processor may be configured to automatically connect a voice call or a video call with the external device.

According to various embodiments, the processor may be configured to transmit the data acquired in the ultrasound diagnosis mode to at least one of the external device and an external screen, which is different from the external device, and perform a configured call connection with the external device.

According to various embodiments, the processor may be configured to receive the control information transmitted based at least partially on the data from the external device, and process an output of an indicator corresponding to the control information based at least partially on the data or the probe.

According to various embodiments, the processor may be configured to detect a detection signal by the probe 600, determine execution of an emergency diagnosis mode in response to the detection signal, and provide an emergency preset.

According to various embodiments, the processor may be configured to omit a preset configuration step and provide simple menus in the emergency diagnosis mode.

As described above, the electronic device 500 according to various embodiments of the present disclosure may include: a display (for example, the display 631 or the touch screen 630); a communication circuit (for example, the wireless communication unit 610) for communication with an external device (for example, the first electronic device 400); and a processor (for example, the controller 680) electrically connected to the display and the communication circuit, wherein the processor is configured to establish communication with the external device, receive data streaming from the external device, perform at least one of displaying the data and mirroring the data to an external screen (for example, a TV or a monitor), receive control information (for example, guide information) related to control of the probe 600 connected to the external device based at least partially on the data, and transmit the control information to the external device.

According to various embodiments, the data may include at least one of first data (for example, an ultrasound image or ultrasound scan data) photographed through the probe 600 connected to the external device and second data (for example, a probe control image or affected part image data) photographed through a camera (for example, the camera module 670) of the external device, and the processor may be configured to perform a call connection with the external device along with reception of the data.

According to various embodiments, the processor may be configured to perform a call connection with the external device along with reception of the data.

According to various embodiments, the processor may be configured to receive user input for a guide of the probe 600 based at least partially on the data, generate the control information on the basis of the user input, and transmit the control information to the external device.

According to various embodiments, the processor may be configured to execute a communication mode, and perform image processing (for example, image processing for transmission to the connected external device or screen switching, that is, screen sharing) related to sharing of the data based on the communication mode.

Figure 7:
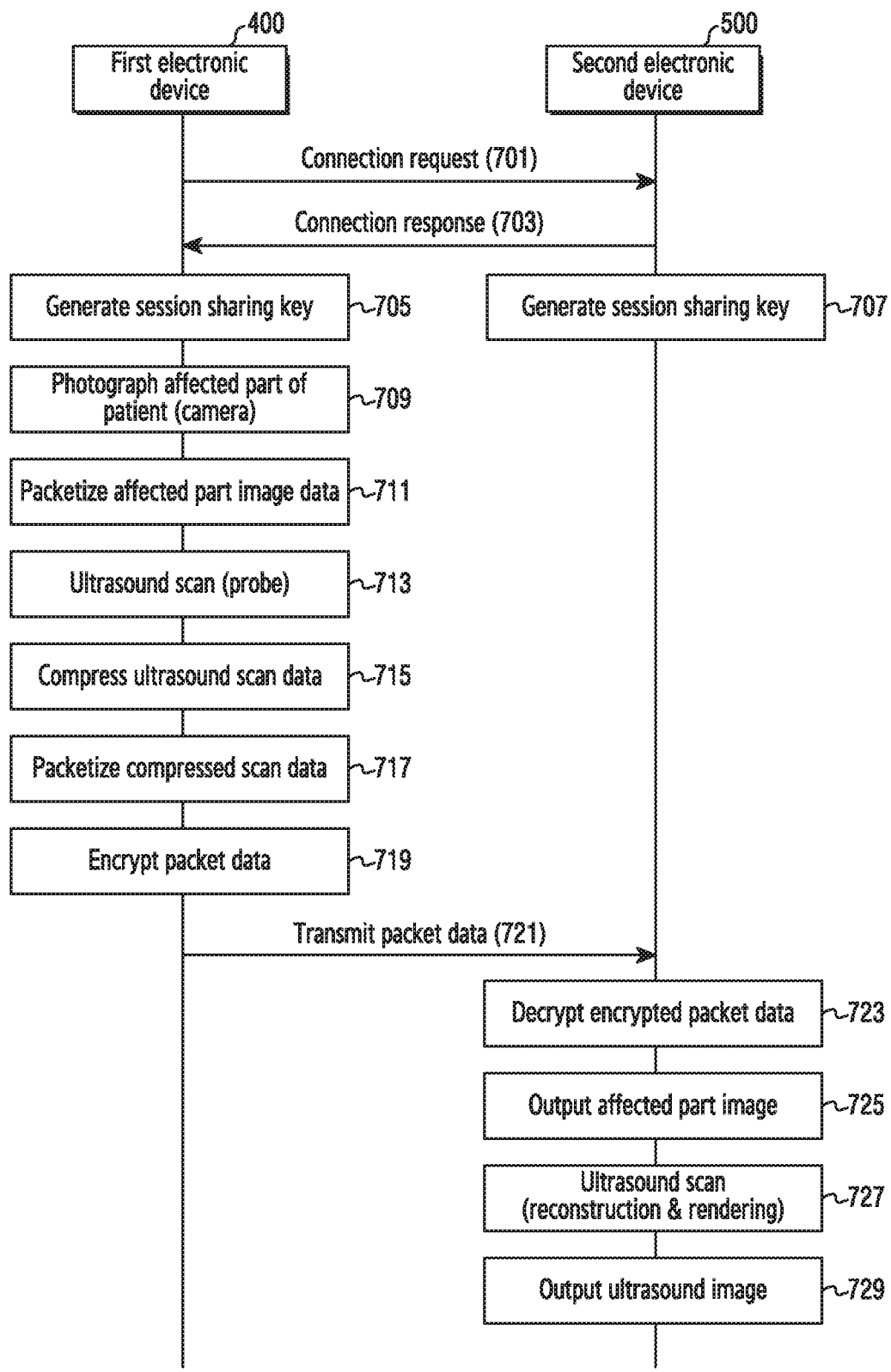
FIG. 7 illustrates the operation of providing data between electronic devices according to various embodiments of the present disclosure.

FIG. 7 illustrates the operation of providing data between electronic devices according to various embodiments of the present disclosure.

FIG. 7 may show an example of the operation, in which, for example, the first electronic device 400 and the second electronic device 500 transmit a status of a patient in a distant place (for example, a user of the first electronic device 400) and an ultrasound diagnosis condition. In FIG. 7, the first electronic device 400 may be a device connected to the probe 600 and the second electronic device 500 may be a PC, a TV, or a device enabling separate calculation and communication in a distant place.

Referring to FIG. 7, in operation 701, the first electronic device 400 may transmit a connection request to the second electronic device 500. According to various embodiments, the first electronic device 400 may transmit the connection request to the first electronic device 400 automatically or manually. An automatic connection request method will be described below. According to an embodiment, the first electronic device 400 may acquire emergency contact information in response to detection of the connection to the probe 600 or detection of entrance into the telemedicine mode and transmit the connection request on the basis of the acquired emergency contact information. According to various embodiments, the emergency contact information may be contact information (for example, connection information of the second electronic device 500 designated by the user) pre-registered in the first electronic device 400 or connection information of the nearest hospital acquired on the basis of the location of the first electronic device 400 or may include connection information of the second electronic device 500 acquired on the basis of at least the part of health information of the user pre-registered in the first electronic device 400.

In operation 703, the second electronic device 500 may transmit a connection response to the first electronic device 400 in response to the connection request of the first electronic device 400.

In operations 705 and 707, each of the first electronic device 400 and the second electronic device 500 may generate a session sharing key. According to an embodiment, when the connection is established on the basis of negotiation according to the connection request and the connection response, the first hearing device 400 and the second hearing device 500 may generate, store, and manage the session sharing key. According to various embodiments, the session may include, for example, a process in the unit of one piece of data to be remotely mirrored. According to various embodiments, in order to handle a plurality of sessions, the sessions may be divided and controlled through a sharing key, which is an identifier (ID).

In operation 709, the first electronic device 400 may photograph an affected part of the patient. According to an embodiment, in response to detection of the connection to the probe 600 or detection of entrance into the telemedicine mode, the first electronic device 400 may perform control to turn on the camera when the camera is in an off state and photograph an outside image through the camera. According to various embodiments, the first electronic device 400 may display an image (for example, a preview image) photographed through the camera on the basis of a preset user interface.

In operation 711, the first electronic device 400 may generate affected part image data based at least partially on the image acquired from the camera (for example, the camera module 670). According to an embodiment, the first electronic device 400 may packetize the affected part image data based at least partially on the preview image. According to an embodiment, the first electronic device 400 may generate first packet data to be transmitted to the second electronic device 500 through the packetizing of the affected part data.

In operation 713, the first electronic device 400 may acquire ultrasound scan data from the probe 600. According to an embodiment, the first electronic device 400 may receive data scanned by the probe 600.

The first electronic device 400 may compress the ultrasound scan data in operation 715, and packetize the compressed ultrasound scan data in operation 717. According to an embodiment, the first electronic device 400 may generate second packet data to be transmitted to the second electronic device 500 through packetizing of the ultrasound scan data. According to various embodiments, the ultrasound scan data may include binary data converted by the transducer of the probe 600 and may reduce the transmission size of the ultrasound scan data through the compression.

In operation 719, the first electronic device 400 may encrypt the packet data. According to an embodiment, the first electronic device 400 may encrypt the first packet data and the second packet data. According to various embodiments, the first electronic device 400 may encrypt the first packet data and the second packet data to one packet or individually encrypt the first packet data and the second packet data to independent packets.

In operation 721, the first electronic device 400 may transmit the packet data to the second electronic device 500. According to an embodiment, the first electronic device 400 may separately and independently transmit the first packet data and the second packet data or may insert them into one packet and then transmit the one packet.

In operation 723, the second electronic device 500 may decrypt the encrypted packet data. According to an embodiment, when separately and independently receiving the first packet data the second packet data, the electronic device 500 may separately decrypt the first packet data and the second packet data. According to an embodiment, when receiving the first packet data and the second packet data through one packet, the second electronic device 500 may decrypt the received packet data. According to various embodiments, the second electronic device 500 may acquire affected part image data corresponding to the first packet data and compressed ultrasound scan data corresponding to the second packet data through the decryption of the packet data.

In operation 725, the second electronic device 500 may output (display) the affected part image based at least partially on the decrypted affected part image data.

In operation 727, the second electronic device 500 may reconstruct and render the decrypted and compressed ultrasound image data.

In operation 729, the second electronic device 500 may output (display) the ultrasound image based at least partially on the reconstructed ultrasound image data.

According to various embodiments, the second electronic device 500 may split the screen to display the affected part image and the ultrasound image, simultaneously display the affected part image and the ultrasound image in a Picture In Picture (PIP) or Picture By Picture (PBP) type, or independently display each of the affected part image and the ultrasound image on an entire screen.

According to various embodiments, the ultrasound scan data may be implemented as the ultrasound image through the reconstruction and the rendering by the second electronic device 500. However, the present disclosure is not limited thereto, and the first electronic device 400 may construct the ultrasound image and then transmit the result thereof to the second electronic device 500 according to the performance and the use of the electronic device.

Figure 8:
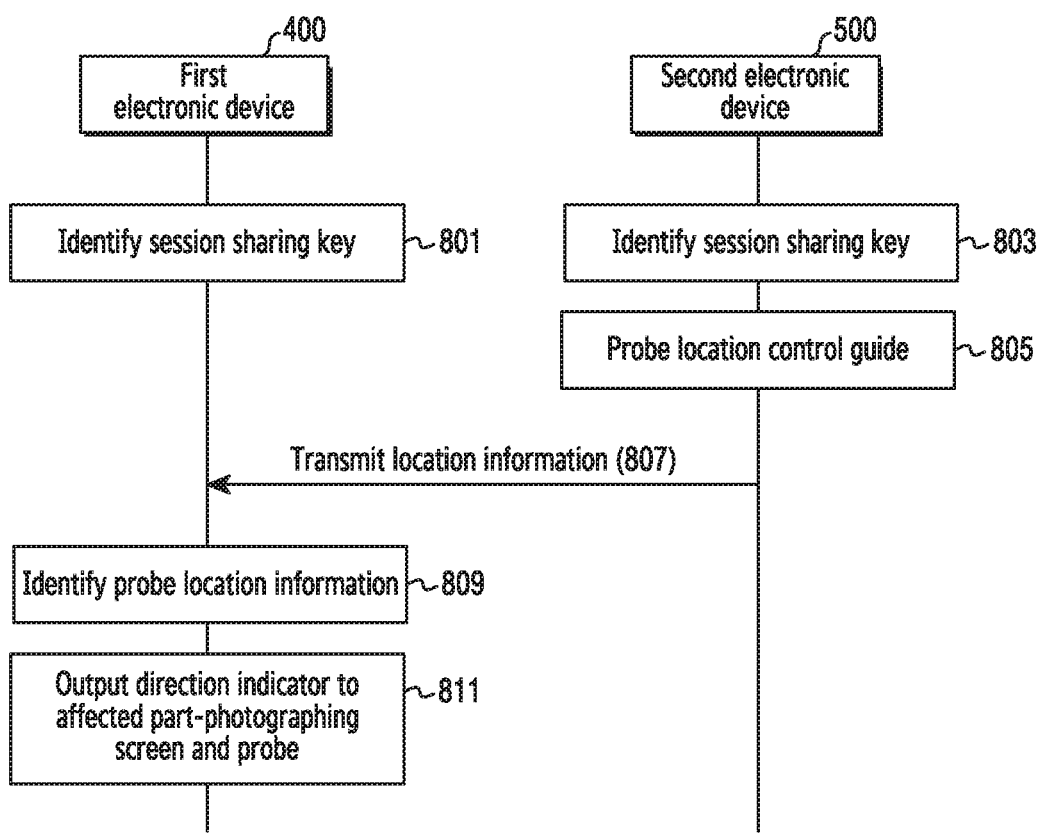
FIG. 8 illustrates the operation of providing data between electronic devices according to various embodiments of the present disclosure.

FIG. 8 illustrates the operation of providing data between electronic devices according to various embodiments of the present disclosure.

FIG. 8 may show an example of the operation in which a user (for example, a user of the second electronic device 500, that is, a doctor) of the second electronic device 500

(for example, a device possessed by the doctor in a hospital) provides an ultrasound diagnosis guide to the first electronic device 400. Referring to FIG. 8, in operations 801 and 803, each of the first electronic device 400 and the second electronic device 500 may identify a session sharing key. According to various embodiments, the session sharing key may be a sharing key generated and stored when the first electronic device 400 and the second electronic device 500 are initially and remotely connected to each other, and may be used for dividing and controlling a plurality of sessions.

In operation 805, the second electronic device 500 may generate a location control guide of the probe 600. According to an embodiment, the second electronic device 500 may generate location information (or control information) for guiding a location at which the probe 600 connected to the first electronic device 400 in a distant place is controlled according to input by the user (for example, doctor).

In operation 807, the second electronic device 500 may transmit location information to the first electronic device 400.

In operation 809, the first electronic device 400 may identify the location information of the probe 600. According to an embodiment, the first electronic device 400 may determine the location for guiding the control location of the probe 600 based on the location information received from the second electronic device 500.

In operation 811, the first electronic device 400 may operate to output a direction indicator for moving the location of the probe 600 based on at least one of an affected part photographing screen and the probe 600. According to an embodiment, the first electronic device 400 may guide the location movement of the probe 600 by displaying the indicator at a location corresponding to direction information on the affected part photographing screen. According to an embodiment, the first electronic device 400 may determine one of a plurality of output units (for example, light emission devices) of the probe 600 according to the direction information and transmit a lighting output by the determined output unit to the probe 600 through a command, so as to guide the location movement of the probe 600 by the lighting of the probe 600.

According to various embodiments, the operation and relevant screen examples for guiding the location movement of the probe 600 will be described in detail with reference to the drawings below.

Figure 9:
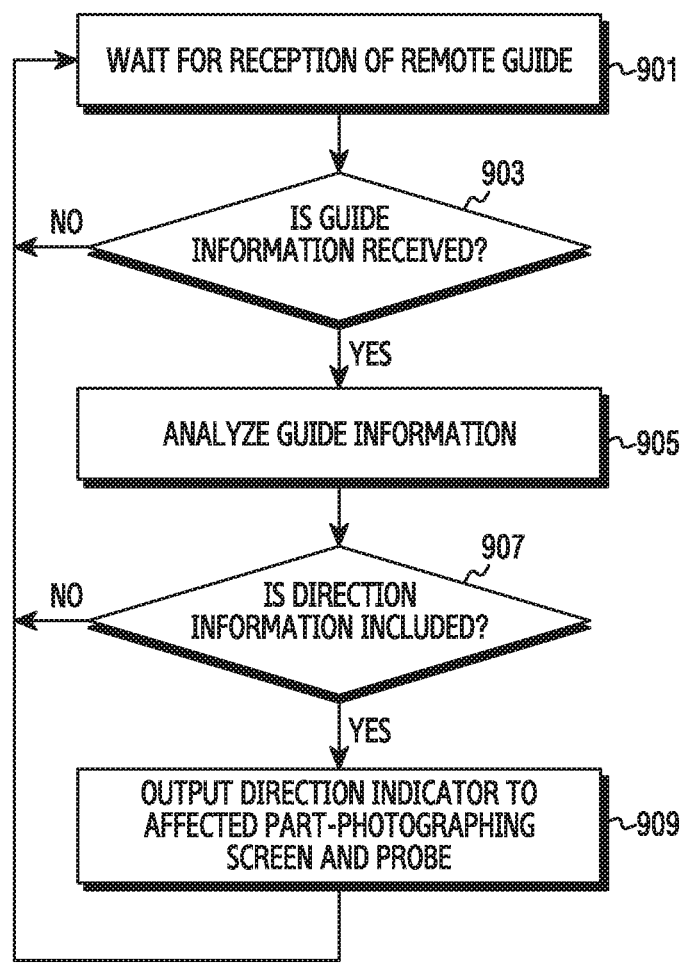
FIG. 9 illustrates the operation in which an electronic device provides a control guide of a probe according to various embodiments of the present disclosure.

FIG. 9 illustrates the operation in which an electronic device provides a control guide of a probe according to various embodiments of the present disclosure.

FIG. 9 may show a detailed example of the operation in which the first electronic device 400 identifies the probe location information in operation 809 of FIG. 8.

Referring to FIG. 9, the first electronic device 400 may wait for reception of the guide from the second electronic device 500 in operation 901, and determine whether guide information is received in operation 903. For example, the first electronic device 400 may wait for reception of guide information including location information (direction information) and/or control information for guiding the control of the probe 600 from the second electronic device 500 connected through wireless communication. According to an embodiment, the first electronic device 400 may continuously transmit ultrasound scan data acquired from the probe 600 and affected image data acquired from the camera to the second electronic device 500 in real time (for example, streaming).

When the first electronic device 400 does not receive the guide from the second electronic device 500 in operation 903 (No of operation 903), the first electronic device 400 may proceed to operation 901 and process operations after operation 901.

When the first electronic device 400 receives the guide from the second electronic device 500 (Yes of operation 903), the first electronic device 400 may analyze guide information in operation 905. According to an embodiment, the guide information may include at least one of location (direction) information related to the location movement of the probe 600 and text or image information related to the control of the probe 600 or action on the patient (for example, the user of the first electronic device 400).

In operation 907, the first electronic device 400 may determine whether the guide information includes direction information. According to an embodiment, the first electronic device 400 may determine whether the received guide information includes direction (location) information for guiding a location movement direction of the probe 600 based on analysis of the guide information.

When the direction information is not included in operation 907 (No of operation 907), the first electronic device 400 may proceed to operation 901 and process operations after operation 901. According to an embodiment, the first electronic device 400 may perform relevant operations corresponding to the received guide. For example, the first electronic device 400 may perform the operation of displaying text or an image according to the received guide.

When the direction information is included in operation 907 (Yes of operation 907), the first electronic device 400 may operate to output a direction indicator for location movement of the probe 600 based on at least one of an affected part photographing screen and the probe 600 in operation 909. According to an embodiment, the first electronic device 400 may guide the location movement of the probe 600 by displaying the indicator at a location corresponding to direction information on the affected part photographing screen. According to an embodiment, the first electronic device 400 may determine one of a plurality of output units (for example, light emission devices) of the probe 600 according to the direction information and transmit a lighting output by the determined output unit to the probe 600 through a command, so as to guide the location movement of the probe 600 by the writing of the probe 600. According to various embodiments, the operation and relevant screen examples for guiding the location movement of the probe 600 will be described in detail with reference to the drawings below.

Hereinafter, the operation of sharing data and providing screen mirroring between electronic devices will be described according to various embodiments.

Figure 10:
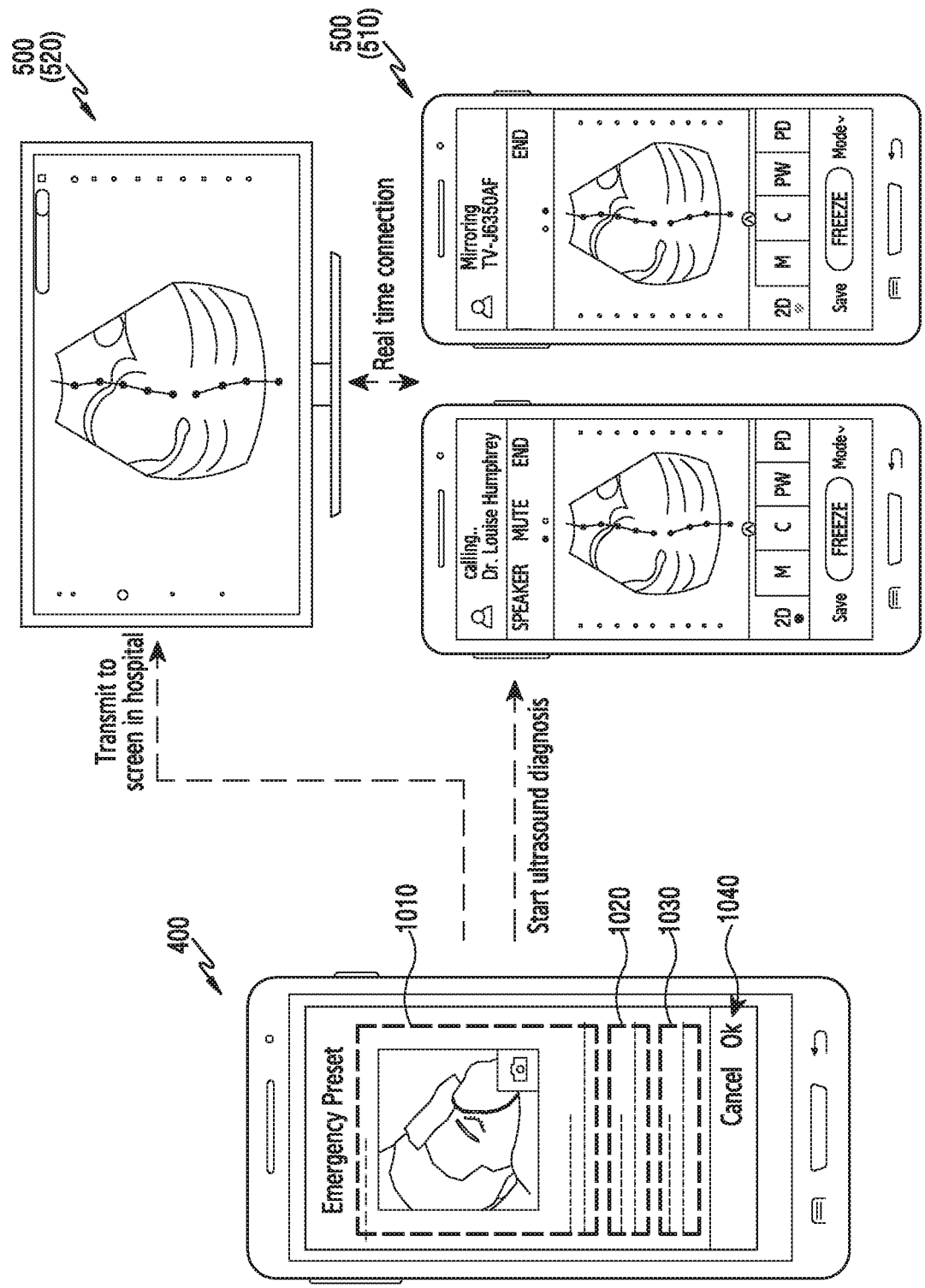
FIG. 10 illustrates an example of the operation of sharing data and providing mirroring between electronic devices according to various embodiments of the present disclosure.

FIG. 10 illustrates an example of the operation of sharing data and providing mirroring between electronic devices according to various embodiments of the present disclosure.

According to various embodiments, the mirroring operation may be an operation of sharing at least some of the ultrasound scan data photographed through the probe 600 and the affected part image data photographed through the camera in real time based on a video call (for example, voice+image) scheme between the first electronic device 400 and the second electronic device 500. According to various embodiments, the mirroring operation may include an operation in which the first electronic device 400 transmits data to the second electronic device 500 and a relevant screen of the data is displayed through the second electronic device 500 and an operation in which the second electronic device 500 displays a relevant screen of the data received from the first electronic device 400 through another external device (for example, a monitor or a TV) connected to the second electronic device 500.

Referring to FIG. 10, the first electronic device 400 may display a user interface related to emergency preset according to entrance into the emergency mode. According to various embodiments, the user interface related to the emergency preset may include a patient information area 1010, a screen mirroring area 1020, a communication area 1030, and a menu area 1040.

In the patient information area 1010, information related to the user of the first electronic device 400 may be provided. For example, the patient information area 1010 may provide an image (for example, a preview image or a still image) photographed through the camera of the first electronic device 400, time information (for example, current date and time), and location information.

The screen mirroring area 1020 may indicate an area in which whether to activate (or perform) a mirroring function is selected. The screen mirroring area 1020 may provide information related to the second electronic device 500, to perform the mirroring operation, or an external device (for example, a TV or a monitor) connected to the second electronic device 500.

The communication area 1030 may indicate an area in which, whether to activate (or perform) a communication function, for example, a voice call function or a video call function is selected. The communication area 1030 may provide information (for example, a user name or nickname based on contact information) related to the second electronic device 500 to be communication-(for example, a voice call or a video call) connected.

The menu area 1040 may indicate an area in which whether to process (perform) a telemedicine based at least partially on data acquired by the first electronic device 400. According to an embodiment, the menu area 1040 may provide an acceptant button (for example, OK) for processing the telemedicine and a rejection button (for example, cancel) for canceling the processing of the telemedicine.

According to various embodiments, when the processing of the telemedicine is requested by the user (for example, a paramedic or the user of the first electronic device 400) who controls the first electronic device 400, the first electronic device 400 may transmit data (for example, at least one piece of ultrasound scan data and affected part image data) to the second electronic device 500. According to an embodiment, when the mirroring function is selected in the screen mirroring area 1020, the first electronic device 400 may perform the mirroring operation by directly transmitting data to the set second electronic device 500 (for example, an external device 520 (for example, a TV or a monitor) within the hospital). According to an embodiment, when the communication function is selected in the communication area 1030, the first electronic device 400 may perform the communication connection with the second electronic device 500 (for example, an electronic device 510 of a doctor in the hospital) based on a selected communication (for example, a voice call or a video call) scheme.

According to various embodiments, when the second electronic device 500 (for example, the electronic device 510) receives data from the first electronic device 400 or communication is established together with the reception of the data, the second electronic device 500 may display a user interface related to telemedicine and selectively perform the mirroring operation. According to an embodiment, the second electronic device 500 may display ultrasound scan data based at least partially on the received data. According to an embodiment, the second electronic device 500 may perform screen mirroring of the received data by linking with (for example, connecting in real time to) the external device 520 (for example, a TV or a monitor).

According to various embodiments, the second electronic device (for example, the electronic device 510) may separately provide pop-ups according to communication connection state switching and screen mirroring state switching. According to an embodiment, in the case of the communication connection state, information indicating that the call is performed (for example, calling . . . ) and user information (for example, Dr. Louise Humphrey) may be provided through a GUI (for example, pop-up) independent from a data screen. In the case of the screen mirroring state, information indicating that mirroring is performed (for example, mirroring) and external device information (for example, TV-J6350AF) may be provided through a GUI independent from the data screen.

According to various embodiments, the external device 520 may display data (for example, ultrasound scan data) directly received from the first electronic device 400. According to various embodiments, the external device 520 may display data (for example, ultrasound scan data) transmitted by the second electronic device 510 connected through, for example, a Wi-Fi Direct scheme or Wi-Fi display scheme.

As illustrated in FIG. 10, according to various embodiments, with respect to the ultrasound image, which is being photographed by the probe 600, a voice call or a video call is performed simultaneously with data communication between the first electronic device 400 and at least one second electronic device 500, so that more accurate telemedicine and/or handling can be performed between the patient in a distant place and the doctor in an emergency or urgent situation. According to an embodiment, the first electronic device 400 may transmit, in real time, an image (or a screen) of at least the part of data (for example, ultrasound diagnosis data or affected part image data) acquired through the probe 600 or the camera to at least one second electronic device 510 or 520 connected in a distant place, so as to share the image (or the screen). According to an embodiment, a user (for example, a paramedic) controlling the first electronic device 400 may share a diagnosis opinion with a medical specialist in a hospital through a voice call and/or a video call and receive a guide for an emergency treatment of the patient.

Figure 11:
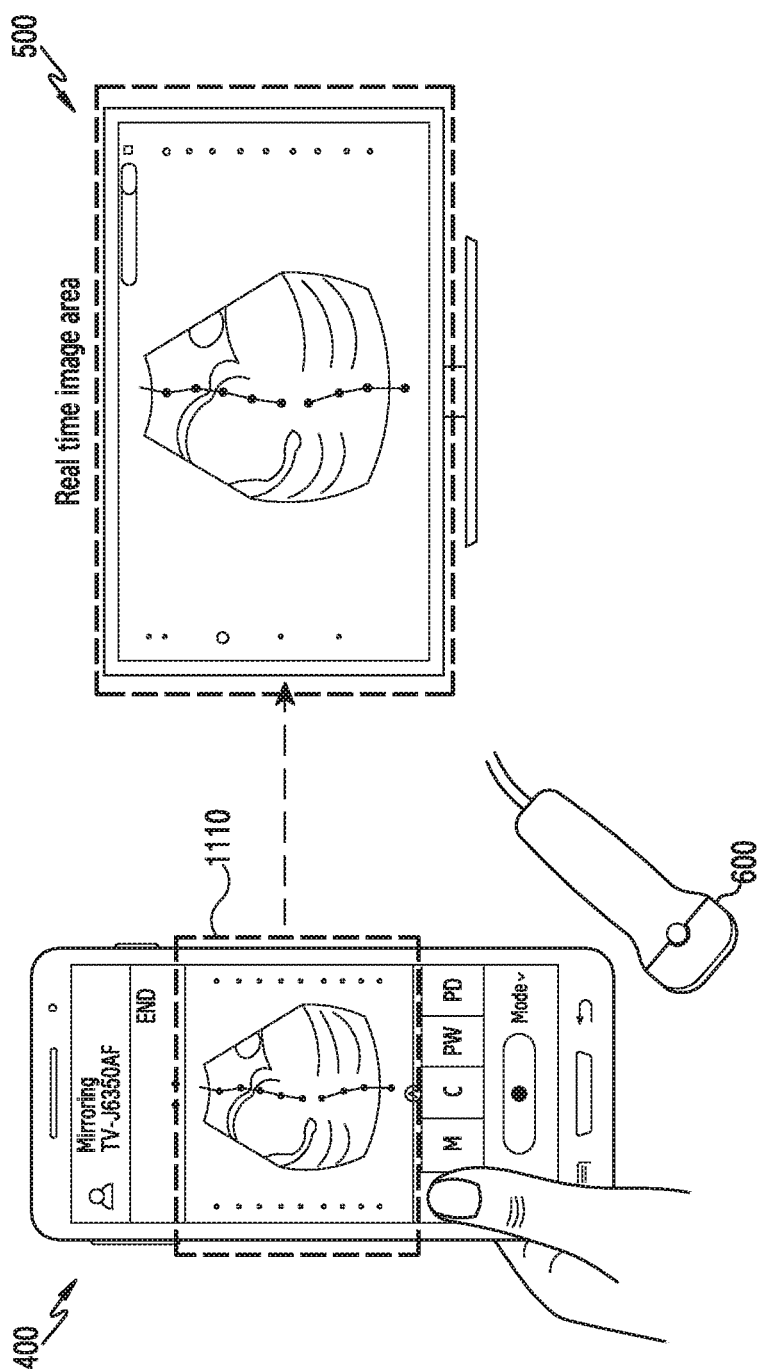
FIG. 11 illustrates an example of the operation of sharing data and providing mirroring between electronic devices according to various embodiments of the present disclosure.

FIG. 11 illustrates an example of the operation of sharing data and providing mirroring between electronic devices according to various embodiments of the present disclosure.

Referring to FIG. 11, FIG. 11 may illustrate a screen example that provides data for an ultrasound image diagnosis. According to various embodiments, the first electronic device 400 may perform screen mirroring only for the ultrasound image area 1110 (for example, a real time image area) except for menu keys unnecessary for the ultrasound image diagnosis.

According to an embodiment, the first electronic device 400 may transmit data (for example, ultrasound scan data) by directly performing screen mirroring with the second electronic device 500 (for example, the external device 520). When performing the screen mirroring with the second electronic device 500 (for example, the external device 520), the first electronic device 400 may transmit only the ultrasound image area 1110 except for the menu keys from the acquired data.

According to an embodiment, the first electronic device 400 may transmit data (for example, ultrasound scan data) to the second electronic device 500 (for example, the electronic device 510) and perform screen mirroring with the external device 520 (for example, a TV or a monitor) connected to the second electronic device 510. According to an embodiment, when performing screen mirroring to the external device 520, the second electronic device 510 may transmit only the ultrasound image area 1110 except for the menu keys for the ultrasound diagnosis.

Figure 12:
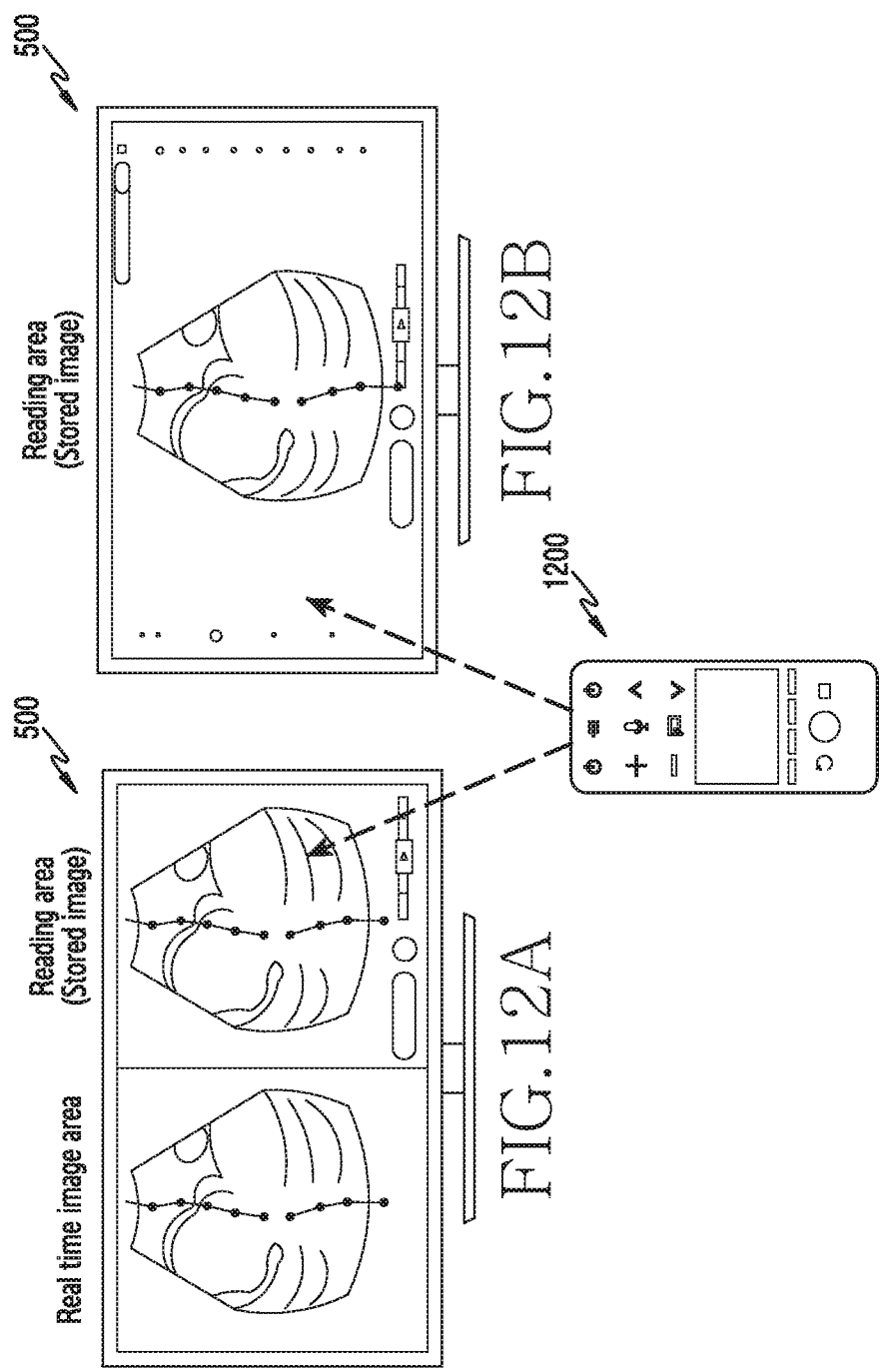
FIG. 12 illustrates an example of the operation in which electronic devices share data and provide mirroring according to various embodiments of the present disclosure.

FIG. 12 illustrates an example of the operation in which electronic devices share data and provide mirroring according to various embodiments of the present disclosure.

Referring to FIG. 12, FIG. 12 may illustrate a screen example of displaying data (for example, ultrasound scan data) provided from the first electronic device 400 in a distant place through the second electronic device 500 (for example, a TV or a monitor).

According to various embodiments, ultrasound scan data displayed through the second electronic device 500 may be controlled using a control device 1200 (for example, a remote controller).

As illustrated in screen (A) of FIG. 12, the user (for example, doctor) may read or diagnose in real time the ultrasound image displayed through second electronic device 500 as illustrated in FIG. 11 through screen split. For example, the user may control the control device 1200 in order to read or diagnose in real time the ultrasound image. The control device 1200 may transmit a control command (for example, a screen splitting command) to the second electronic device 500 in response to a user control.

The second electronic device 500 may split the screen and provide the split screens in response to detection of the screen splitting command of the control device 1200. According to an embodiment, the second electronic device 500 may divisibly provide an ultrasound image area and a reading area. According to an embodiment, the second electronic device 500 may provide an ultrasound image through the ultrasound image area and provide a stored image (for example, a still image or a captured image of the ultrasound image) through the reading area. According to an embodiment, the reading area may be provided while including a menu related to controlling and/or reading the ultrasound image. For example, menus such as Freeze/Unfreeze for stopping or playing an image, Save for storing an image, Zoom In/Out for enlarging or reducing an image, Pen for memo or drawing, and Measure for measuring a distance or size may be provided in one area of the screen (for example, a lower part of the screen).

As illustrated in screen (B) of FIG. 12, when the user (for example, doctor) read records or the stored diagnosis image again, the user may read the diagnosis image by controlling the second electronic device 500 through the control device 1200. For example, the user may perform control to select the diagnosis image or to enlarge the reading area in a state like screen (A) of FIG. 12 through the control device 1200. The control device 1200 may transmit a control command (for example, a reading area enlargement command or an image list command) to the second electronic device 500 in response to user control.

The second electronic device 500 may enlarge and provide the screen in response to detection of the control command (for example, the reading area enlargement command) of the control device 1200. According to another embodiment, the second electronic device 500 may display an image list in response to the control command (for example, the image list command) of the control device 1200 and provide an image selected from the image list through an entire screen. According to an embodiment, the reading area may be provided while including a menu related to controlling and/or reading the ultrasound image. For example, menus such as Freeze/Unfreeze for stopping or playing an image, Save for storing an image, Zoom In/Out for enlarging or reducing an image, Pen for memo or drawing, and Measure for measuring a distance or size may be provided in one area of the screen (for example, a lower part of the screen).

Figure 13:
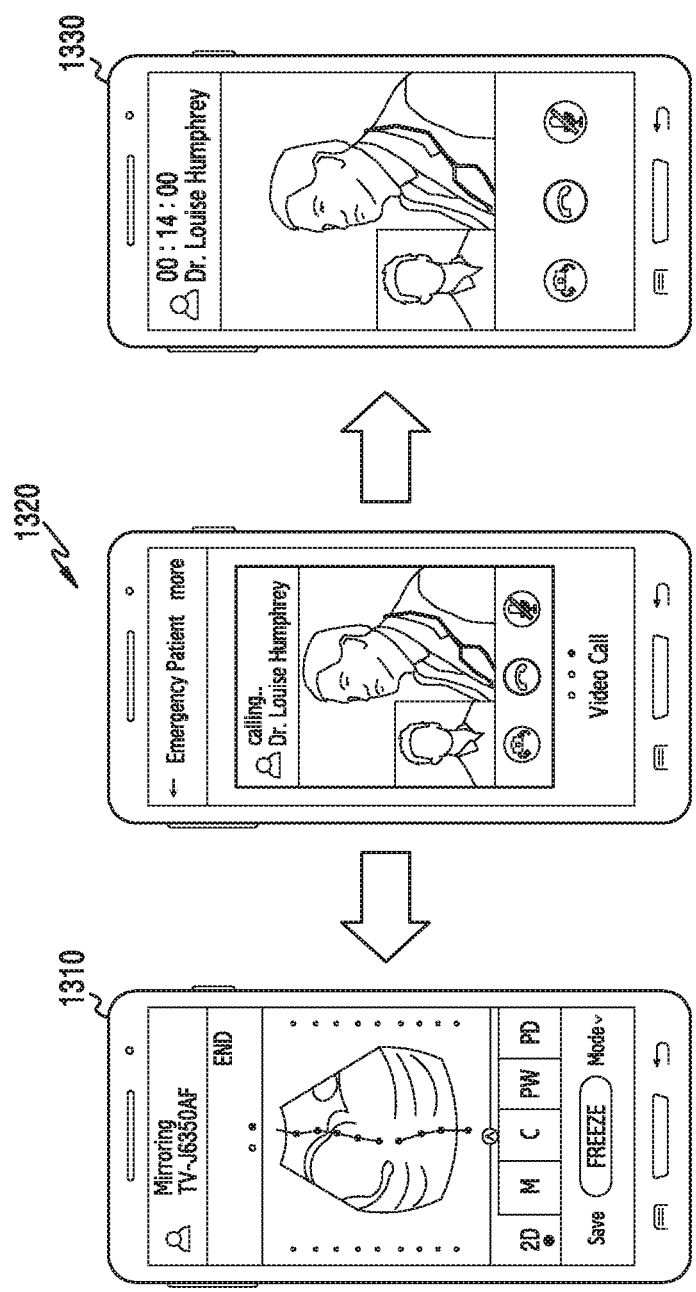
FIG. 13 illustrates an example of a user interaction-based operation of the electronic device according to various embodiments of the present disclosure.

FIG. 13 illustrates an example of a user interaction-based operation of the electronic device according to various embodiments of the present disclosure.

Referring to FIG. 13, FIG. 13 may illustrate a screen example of switching a video call during an ultrasound diagnosis on the basis of data (for example, ultrasound scan data) shared between electronic devices. For example, FIG. 13 may show an example of controlling screen switching on the basis of a one finger interaction.

According to various embodiments, when the electronic device (for example, the first electronic device 400 or the second electronic device 500) detects particular user input (for example, long press, swipe, or flick) while an ultrasound image is displayed, for example, an ultrasound diagnosis is performed, the electronic device may switch the video call in response to the user input.

According to an embodiment, as illustrated in a screen 1310, the user (for example, a paramedic or a doctor) may input long press on the ultrasound diagnosis screen to switch to a video call as shown in a screen 1330. The electronic device may switch from the ultrasound diagnosis screen 1310 to the video call screen 1330 and provide the video call screen 1330 in response to detection of the user input. According to various embodiments, the video call screen 1330 may switch to the ultrasound diagnosis screen 1310 according to the user input (for example, long press).

According to an embodiment, as illustrated in the screen 1310, the user (for example, a paramedic or a doctor) may switch the ultrasound diagnosis screen to the video call screen like the screen 1330 by inputting swipe in one direction (or regardless of direction). According to various embodiments, the user may switch the video call screen 1330 to the ultrasound diagnosis screen 1310 according to the user input (for example, swipe).

According to various embodiments, the electronic device may provide a GUI related to screen switching when the screen switching to the ultrasound diagnosis screen 1310 or the video call screen 1330 is performed. According to an embodiment, as illustrate din the screen 1320, the electronic device may provide a screen switching effect (for example, slide in/out, fade in/output, or image transition) for screen switching between the ultrasound diagnosis screen 1310 and the video call screen 1330.

Figure 14:
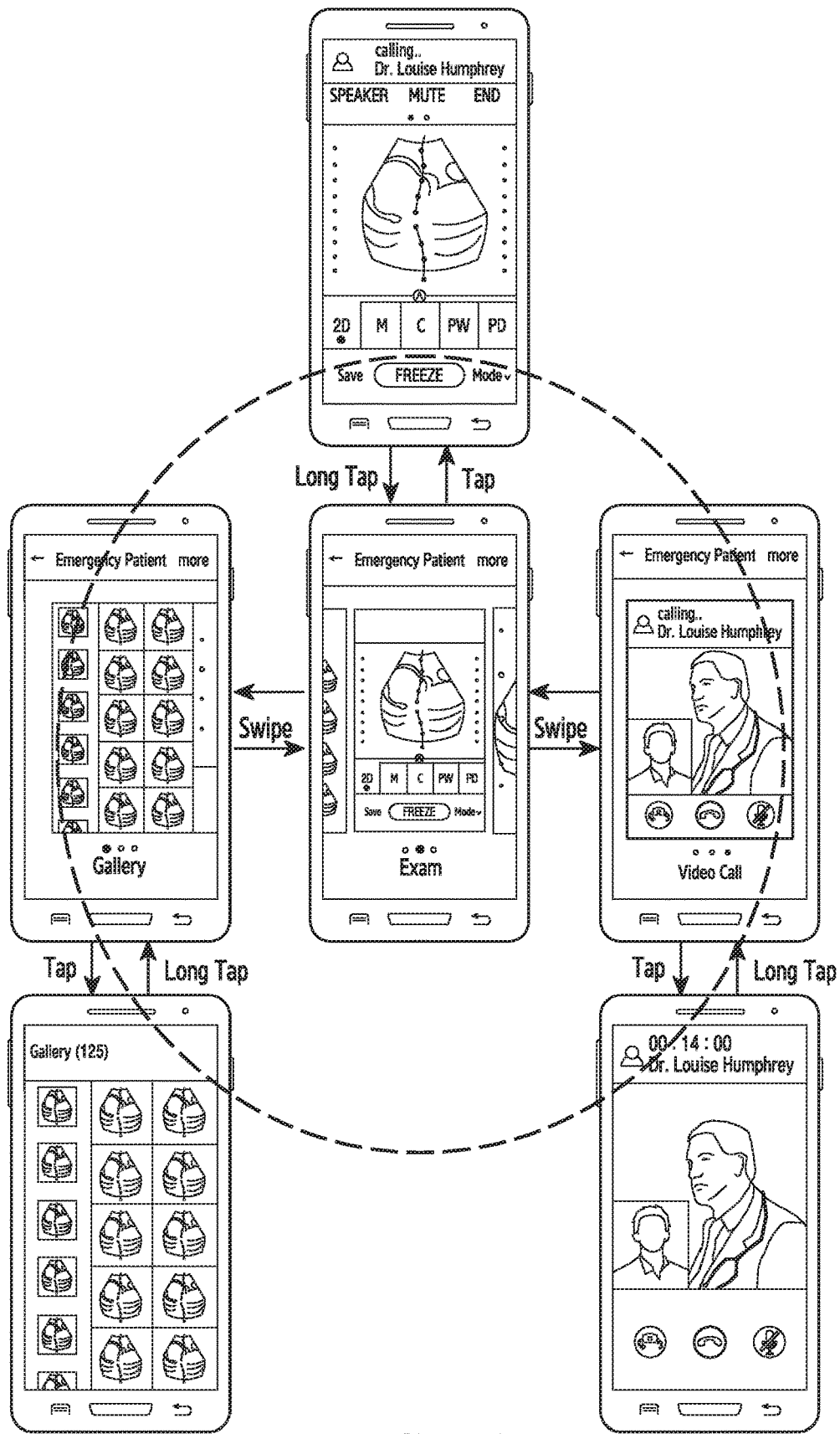
FIG. 14 illustrates an example of a user interaction-based operation of the electronic device according to various embodiments of the present disclosure.

FIG. 14 illustrates an example of a user interaction-based operation of the electronic device according to various embodiments of the present disclosure.

Referring to FIG. 14, FIG. 14 may illustrate an example of controlling screen switching on the basis of a one finger interaction during an ultrasound diagnosis based on data (for example, ultrasound scan data) shared between electronic devices (for example, the first electronic device 400 and the second electronic device 500). According to various embodiments, it is possible to distinguish various one finger-based user inputs and control screen switching on the basis of the user input.

As illustrated in FIG. 14, for example, user inputs which can be performed during the ultrasound diagnosis include long tap, tap, and swipe, and switching between pages, switching between depths, switching between categories, or switching between functions may be configured to each one finger-based user input. According to an embodiment, screen switching and a relevant GUI according to page switching, depth switching, category switching, or function switching may be provided based on a switching scheme according to the user input.

According to various embodiments, the user (the paramedic of the first electronic device 400 or the doctor of the second electronic device 500) can freely perform screen switching through the one finger-based interaction during the ultrasound diagnosis, so that user convenience can be improved.

Figure 15:
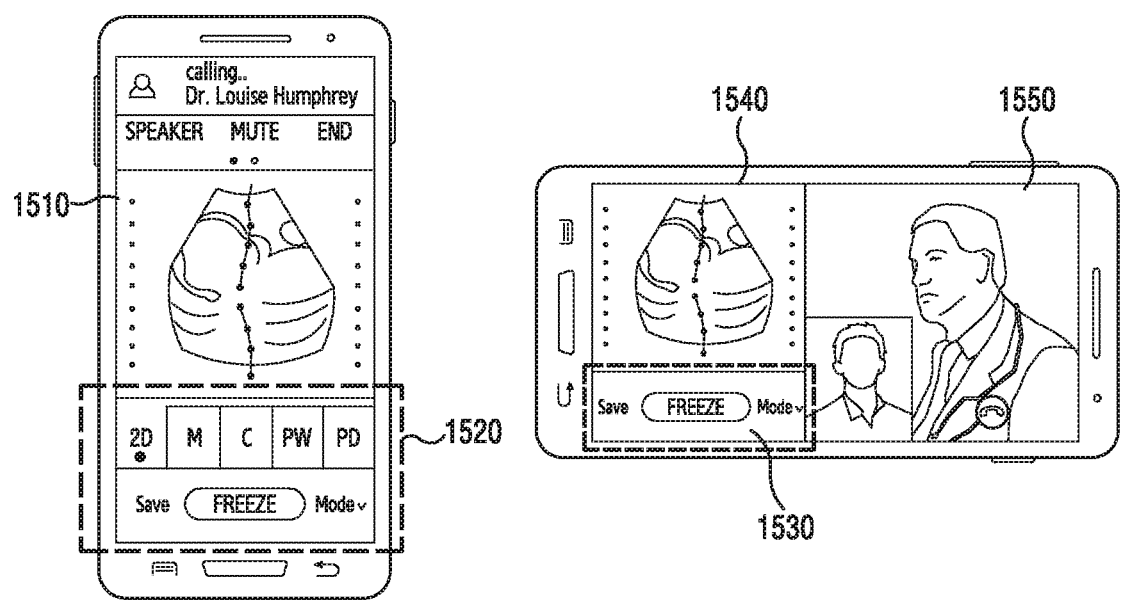
FIG. 15 illustrates an example of the operation in which the electronic device displays data according to various embodiments of the present disclosure.

FIG. 15 illustrates an example of the operation in which the electronic device displays data according to various embodiments of the present disclosure.

Referring to FIG. 15, FIG. 15 may illustrate an example of providing screens through different GUIs according to orientation (for example, landscape mode and portrait mode) switching of the electronic device during the ultrasound diagnosis by the electronic device (for example, the first electronic device 400 or the second electronic device 500).

According to various embodiments, the electronic device may include various methods of combining screens (for example, an ultrasound image screen and a video call screen) to be output to the display. For example, several screens may be hierarchically combined (for example, in an overlay type), may be combined with a lower screen after assigning transparency to a particular screen, may be combined in a Picture In Picture (PIP) type or a Picture By Picture (PBP) type, or may be combined in a screen split type. The example of FIG. 15 may correspond to the case in which screens are combined in a screen split type.

As illustrated in FIG. 15, the electronic device may display a basic ultrasound diagnosis screen during the ultrasound diagnosis in portrait mode. According to an embodiment, the electronic device may provide an ultrasound image 1510 and all menus 1520 included in the basic ultrasound diagnosis screen in portrait mode. For example, the electronic device may provide main menus such as Freeze, Save, and Q Scan, and sub menus such as a Mode button and a Measure button.

As illustrated in FIG. 15, when the electronic device determines a change to landscape mode while the basic ultrasound diagnosis screen in portrait mode is displayed, the electronic device may combine the ultrasound diagnosis screen 1540 and the video call screen 1550 in a screen split type and provide the screens. For example, the electronic device may provide the ultrasound diagnosis screen 1540 including an ultrasound image and the video call screen 1550 including a call image between users together through screen split. According to various embodiments, the ultrasound diagnosis screen 1540 and the video call screen 1550 may be combined in a PIP, a PBP, or an overlay type and then provided. According to an embodiment, when the combined screen in landscape mode is provided, only the main menu 1530 may be provided in the ultrasound diagnosis screen 1540.

The electronic device may detect a change in (or rotation of) the orientation of the electronic device. For example, a change from portrait mode to landscape mode or a change from landscape mode to portrait mode may be determined. The electronic device may provide the basic ultrasound diagnosis screen or a combined screen generated by combining at least two screens including the ultrasound diagnosis screen based on switching between electronic devices.

Figure 16:
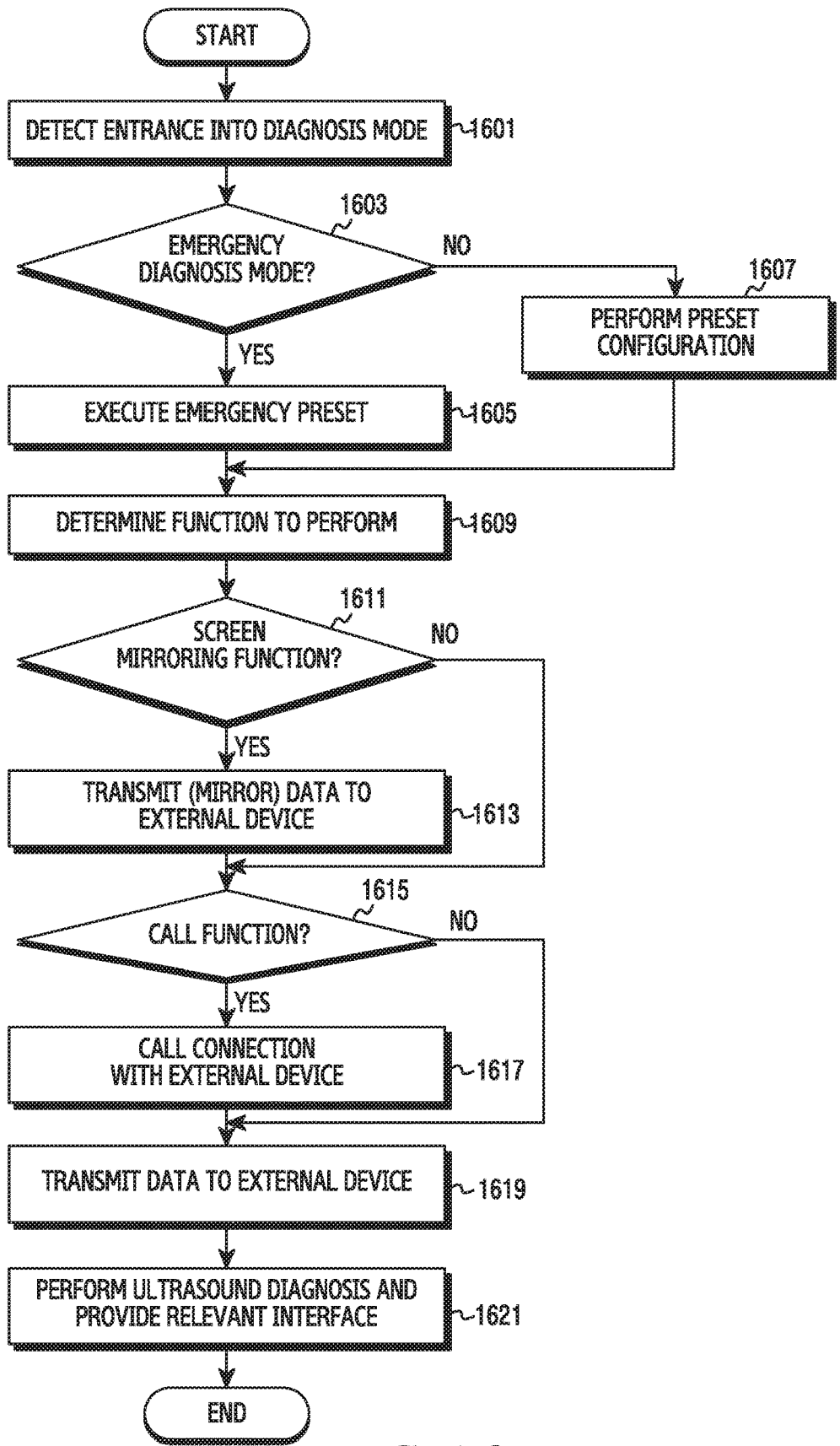
FIG. 16 is a flowchart illustrating the operation of sharing data between electronic devices according to various embodiments of the present disclosure.

FIG. 16 is a flowchart illustrating the operation of sharing data between electronic devices according to various embodiments of the present disclosure.

Referring to FIG. 16, in operation 1601, the controller 680 of the electronic device 400 may detect entrance into diagnosis mode. According to various embodiments, the operation of determining entrance into the diagnosis mode will be described in detail with reference to the drawings below.

In operation 1603, the controller 680 may determine whether the entrance into the diagnosis mode is entrance into emergency diagnosis mode or into basic diagnosis mode in response to detection of the entrance into the diagnosis mode.

When the controller 680 determines the entrance into the basic diagnosis mode in operation 1603 (No of operation 1603), the controller 680 may perform a preset configuration step in operation 1607. According to various embodiments, the preset configuration operation will be described in detail with reference to the drawings below.

When the controller 680 determines the entrance into the emergency diagnosis mode in operation 1603 (Yes of operation 1603), the controller 680 may execute the emergency preset. For example, the controller 680 may omit the preset configuration step of operation 1607 and immediately execute the emergency preset. Such an example is illustrated in FIG. 10 and the following drawings.

In operation 1609, the controller 680 may determine function to perform. According to an embodiment, the controller 680 may determine whether there are a screen mirroring function and/or a call function selected and configured by the user as illustrated in FIG. 10.

In operation 1611, the controller 680 may determine whether the screen mirroring function is selected. According to an embodiment, the controller 680 may determine whether there is user selection based on the screen mirroring area 1020 as illustrated in FIG. 10.

When the screen mirroring function is not selected in operation 1611 (No of operation 1611), the controller 680 may process operations after operation 1615.

When the screen mirroring function is selected in operation 1611 (Yes of operation 1611), the controller 680 may transmit data to an external device (for example, the second electronic device 500 or an external screen) preset for screen mirroring in operation 1613. According to an embodiment, when the screen mirroring function is selected, the controller 680 may identify information related to the external device preset for screen mirroring or extract information related to the external device on the basis of contact information of the user or history information (for example, health information) of the user. The controller 680 may transmit data to the corresponding external device on the basis of the identified or extracted information of the external device. According to various embodiments, the data may include one or more of ultrasound scan data (for example, an ultrasound image) photographed by the probe 600 and affected part image data (for example, a preview image (for example, a probe control image) as a real-time (or live) image) photographed by the camera (for example, a rear camera of the electronic device). According to various embodiments, the external device according to the selection of the screen mirroring function may include an external screen (for example, a TV or a monitor) in the hospital (for example, an examining room).

In operation 1615, the controller 680 may determine whether the call function is selected. According to an embodiment, the controller 680 may determine whether there is user selection on the basis of the communication area 1030 as illustrated in FIG. 10.

When the call function is not selected in operation 1615 (No of operation 1615), the controller 680 may process operations after operation 1619.

When the call function is selected in operation 1615 (Yes of operation 1615), the controller 680 may perform a call connection with the external device. According to an embodiment, a target external device for the call connection may include an electronic device of a doctor. According to another embodiment, the target external device for the call connection and the target external device for screen mirroring may be different devices or the same device.

In operation 1619, the controller 680 may transmit data to the call-connected external device (for example, the second electronic device 500). According to an embodiment, when the call function is selected, the controller 680 may identify information related to an external device preset for the call (for example, a voice call or a video call) connection or extract information related to the external device on the basis of contact information of the user or history information (for example, health information) of the user. The controller 680 may connect a call with the corresponding external device or transmit data to the corresponding external device on the basis of the identified or extracted information of the external device. According to various embodiments, the data may include one or more of, for example, ultrasound scan data (for example, an ultrasound image) photographed by the probe 600 and affected part image data (for example, a probe control image) photographed by the camera (for example, a rear camera of the electronic device).

In operation 1621, the controller 680 may perform the ultrasound diagnosis and provide a relevant interface. For example, as described with reference to FIGS. 10 to 15, the controller 680 may process the operation of providing various screen interface related to the performance of the diagnosis mode with another electronic device in a distant place and outputting an indicator for screen switching, function switching, or a probe control guide based at least partially on a user or user input in the distant place.

According to various embodiments, although FIG. 16 sequentially illustrates the operations for convenience of description, the operations are not limited thereto. For example, according to various embodiments, the operations may be performed sequentially before, in parallel to operations 1611 to 1619, or inversely. According to an embodiment, when determining the function to perform in operation 1609, the controller 680 may simultaneously identify whether to select the screen mirroring function and the call function and perform the data transmission and call connection operations sequentially, in parallel, or inversely based at least partially on the result thereof.

Hereinafter, according to various embodiments, the operation of providing a guide for controlling the probe 600 connected to the first electronic device 400 will be described.

Figure 17:
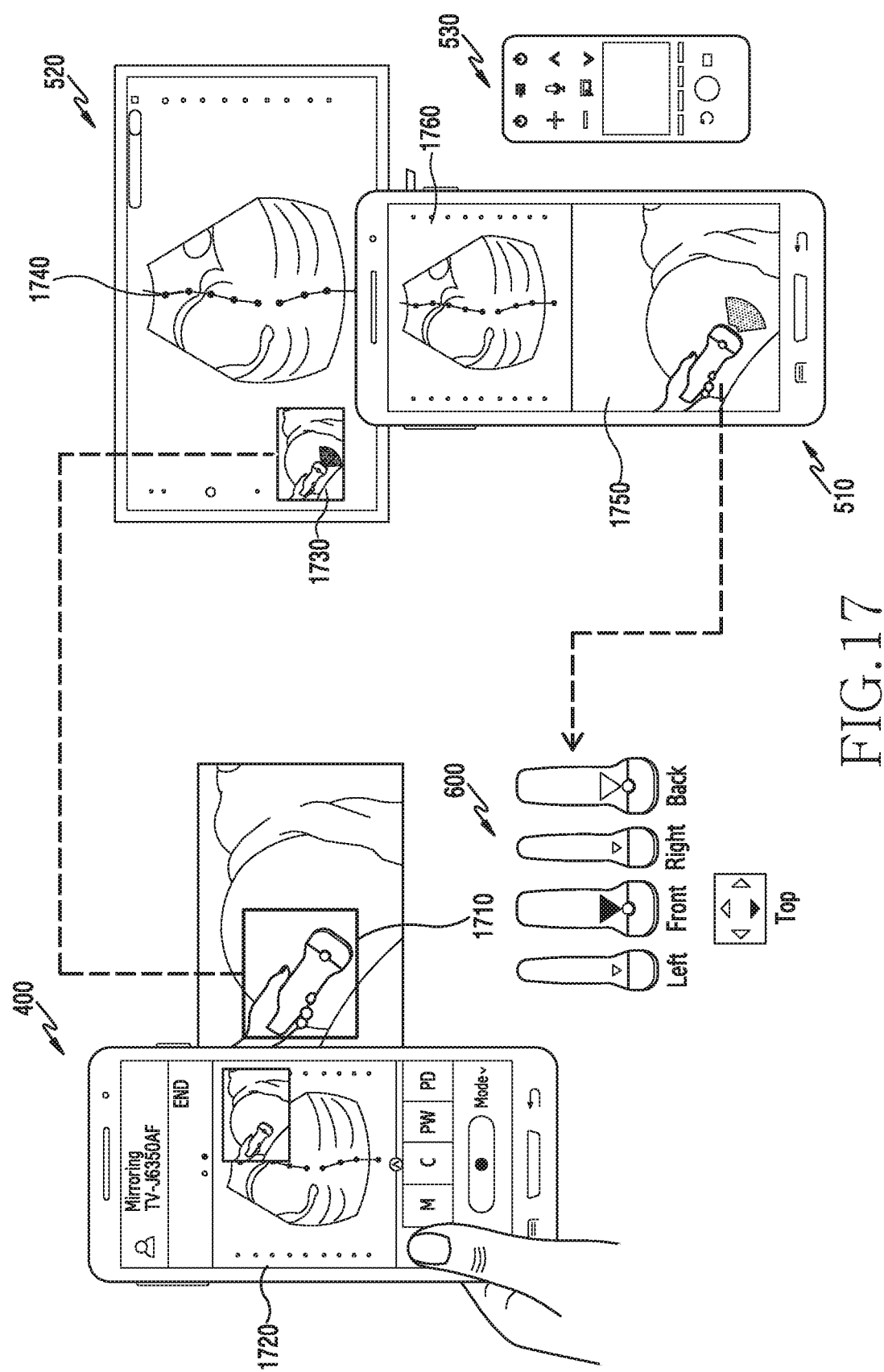
FIG. 17 is a diagram illustrating the operation of providing a probe control guide according to various embodiments of the present disclosure.

FIG. 17 is a diagram illustrating the operation of providing a probe control guide according to various embodiments of the present disclosure.

According to various embodiments, the first electronic device 400 may photograph a control state of the probe 600 through the camera (for example, the camera module 670 or the rear camera) and transmit the photographed image to the second electronic device 500 in real time. For example, the first electronic device 400 may transmit affected part image data 1710 photographed through the camera to the second electronic device 500 in a streaming type in real time.

According to various embodiments, the first user (for example, the user controlling the probe 600) may allow the camera of the first electronic device 400 to photograph a control state of the probe 600 in contact with an affected part of the patient, and the first electronic device 400 may transmit photographed affected part image data 1710 to the second electronic device 500 together with or independently from ultrasound diagnosis data 1720 acquired from the probe 600.

According to various embodiments, the second user (for example, the user of the second electronic device 500, that is, the doctor) may identify control images 1730 and 1750 of the probe 600 through the affected part image data in addition to ultrasound images 1740 and 1760 of the ultrasound diagnosis data based on the second electronic device 500 (for example, the smart phone 510 or the external screen 520 (a TV or a monitor). The second user may provide a control guide of the probe 600 in order to acquire an ultrasound image read for accurate diagnosis. For example, the second user may provide a guide related to the control of the probe 600 on the basis of a user control using the electronic device 500. According to an embodiment, the second user may photograph the accurate ultrasound image by indicating a movement direction of the probe 600 to a paramedic in a distant place by using (controlling) a direction key of the second electronic device 500 (for example, the smart phone 510 or the control device 530). The second electronic device 500 may generate guide information corresponding to the user control and transmit the generated guide information to the first electronic device 400.

According to various embodiments, the first electronic device 400 may operate to provide (output) a control guide of the probe 600, for example, an indicator in one of various schemes in response to reception of guide information from the second electronic device 500. According to an embodiment, the first electronic device 400 may analyze the guide information, determine (recognize) direction information (or location information) included in the guide information, and output the indicator for designating a movement direction (location) of the probe 600 based at least partially on the determination result.

According to an embodiment, the first electronic device 400 may output a guide for acquiring the accurate ultrasound image as a direction guide within the screen of the first electronic device 400.

According to an embodiment, the first electronic device 400 may provide a guide for acquiring the accurate ultrasound image as a direction guide using direction display lighting of the probe 600. For example, the first electronic device 400 may determine direction information (or location information) in the guide information and transmit a control command to the probe 600 to perform lighting corresponding to the determined direction information. The probe 600 may perform lighting by an included output unit (for example, an LED or an infrared ray as a light emission device) in response to a control command of the first electronic device 400. According to an embodiment, the probe 600 may be configured to include output units for outputting indicators corresponding to at least four directions on four sides (for example, Left, Front, Right, and Back), respectively, or four output units for outputting indicators corresponding to at least four directions on one side (for example, Top or Tail). The probe 600 may perform lighting by the output unit in the corresponding direction (location) in response to the control command of the first electronic device 600.

Figure 18A:
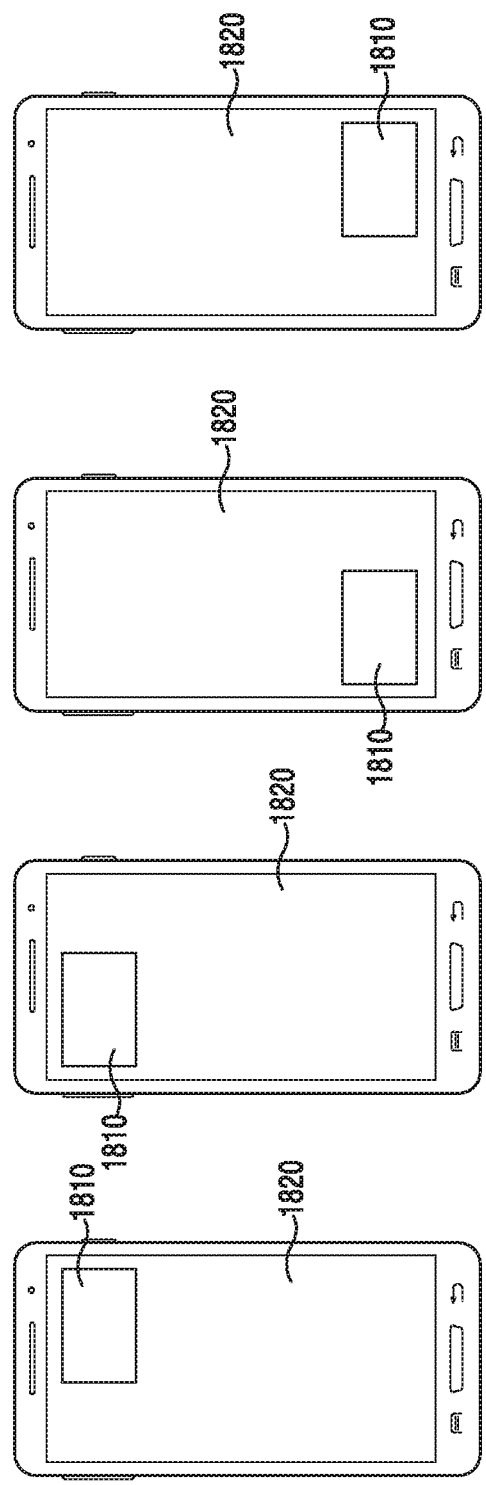
FIGS. 18A and 18B are diagrams illustrating the operation of providing a control image for a probe control guide according to various embodiments of the present disclosure.
Figure 18B:
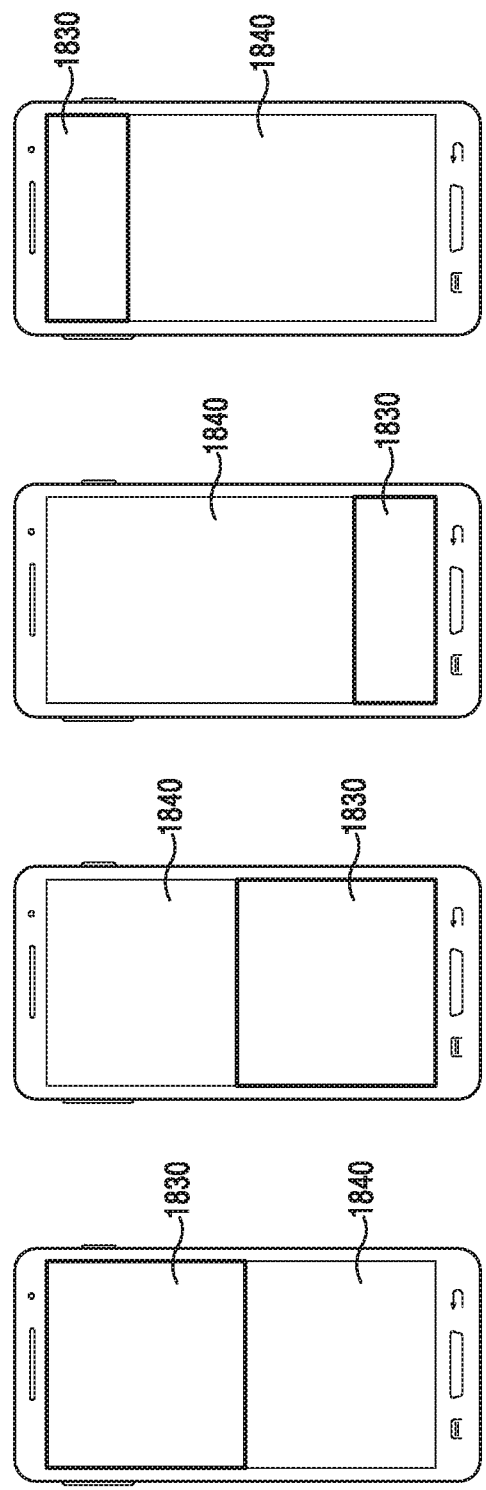

FIGS. 18A and 18B are diagrams illustrating the operation of providing a control image for a probe control guide according to various embodiments of the present disclosure.

Referring to FIGS. 18A and 18B, the first electronic device 400 may be connected to the probe 600 and may display a control image of the probe 600 obtained by photographing the control of the probe 600 in real time through the camera (for example, the camera module 670 or the rear camera) of the first electronic device 400 on the basis of various GUIs.

According to an embodiment, as illustrated in FIG. 18A, the first electronic device 400 may providing a floating GUI related to an image 1810 photographed in real time (for example, affected part image data as a preview image) acquired by the camera in a partial area of the screen.

According to various embodiments, the GUI (for example, a pop-up window of the image photographed in real time, which is acquired through the rear camera) may be provided in various forms such as rectangular, triangular, polygonal, and circular forms. According to various embodiments, the GUI may move according to user input. According to various embodiments, the GUI related to the image 1810 photographed in real time may be displayed through a window independent from an ultrasound image 1820 acquired from the probe 600, and one window may be displayed in an overlap type such that the window overlaps at least the part of another window. For example, the first electronic device 400 may display the image 1810 photographed in real time on the ultrasound image 1820 through a particular type GUI (for example, a pop-up window) in a Picture In Picture (PIP) or a Picture By Picture (PBP) form.

According to various embodiments, the GUI may be located in one area (for example, an upper right part of the screen, an upper left part of the screen, a lower left part of the screen, or a lower right part of the screen) on the ultrasound image 1820 as illustrated in FIG. 18A. The GUI may be displayed in, for example, a bubble form. The size and location of the GUI may be changed by the user.

According to an embodiment, as illustrated in FIG. 18B, the first electronic device 400 may split the screen and provide the GUI related to the image 1830 (for example, the affected part image data as the preview image) photographed in real time, which is acquired through the camera.

According to various embodiments, the GUI (for example, the image photographed in real time, which is acquired through the rear camera) may be displayed through a window independent from the ultrasound image acquired from the probe 600, and each window may be displayed to not overlap each other. For example, the first electronic device 400 may independently display the ultrasound image 1840 and the image 1830 photographed in real time on vertically or horizontally split screens.

According to various embodiments, the GUI may be located on a lower side or an upper side in the vertically split type or located on a left side or a right side in the horizontally split type as illustrated in FIG. 18B. According to various embodiments, the split screens may be implemented at the same ratio or different ratios. The size (for example, ratio) or location of the GUI may be changed by the user.

Figure 19B:
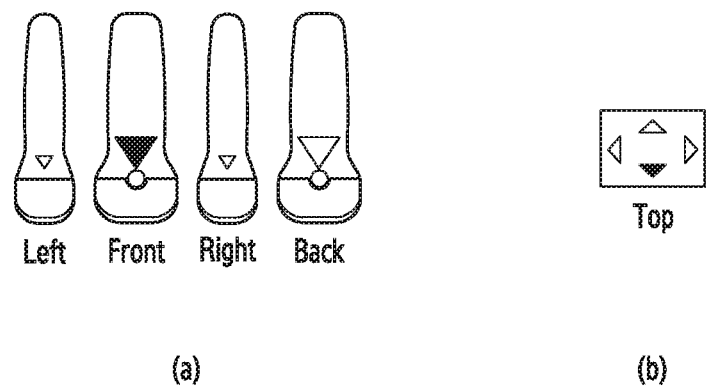
Figure 19C:
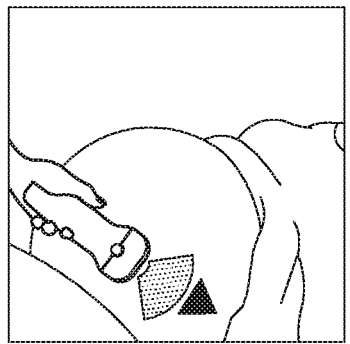

FIGS. 19A, 19B, and 19C are diagrams illustrating the operation of providing indicators for probe control guides according to various embodiments of the present disclosure.

Referring to FIGS. 19A, 19B, and 19C, the first electronic device 400 may display indicators for guiding the control of the probe 600 instructed by the second electronic device 500 based on various schemes.

According to an embodiment, as illustrated in FIG. 19A, the first electronic device 400 may provide the indicators based on at least partially on various GUIS within the screen. For example, the indicators may be provided on the basis of the screen of the first electronic device 400. According to various embodiments, the indicators for the control guides of the probe 600 may provide an indicator in a corresponding direction through a user interface such as an arrow, lighting, or a watch on a separate window or an image photographed in real time.

According to an embodiment, as illustrated in FIG. 19B, the first electronic device 400 may provide the indicators based at least partially on at least some output units (for example, an LED or an infrared ray as a light emission device) of the probe 600. For example, the indicators may be provided on the basis of light of the probe 600. According to various embodiments, the first electronic device 400 may transfers a control command for controlling the output unit of the probe 600 corresponding to a direction instructed by the second electronic device 500 to the probe 600, and the probe 600 may provide the indicators on the basis of lighting (for example, emission of the LED) of the output unit in the corresponding direction in response to the control command. According to an embodiment, as illustrated in example (A) of FIG. 19B, the indicator may be provided through lighting by the output unit in the corresponding direction among output units on sides (for example, Left, Front, Right, and Back) on a head of the probe 600. According to an embodiment, as illustrated in example (B) of FIG. 19B, the indicator may be provided through lighting by the output unit in the corresponding direction among output units on a tail of the probe 600.

According to an embodiment, as illustrated in FIG. 19C, the first electronic device 400 may provide the indicator to the outside based at least partially on at least some output units (for example, light emission device) of the probe 600. For example, the indicator may be provided on the basis of the body. According to various embodiments, the first electronic device 400 may transfer a control command for controlling the output unit of the probe 600 corresponding to the direction instructed by the second electronic device 500 to the probe 600, and the probe 600 may directly provide the indicator to a patient body on the basis of lighting (for example, infrared ray or beam output) of the output unit in the corresponding direction in response to the control command.

Figure 20A:
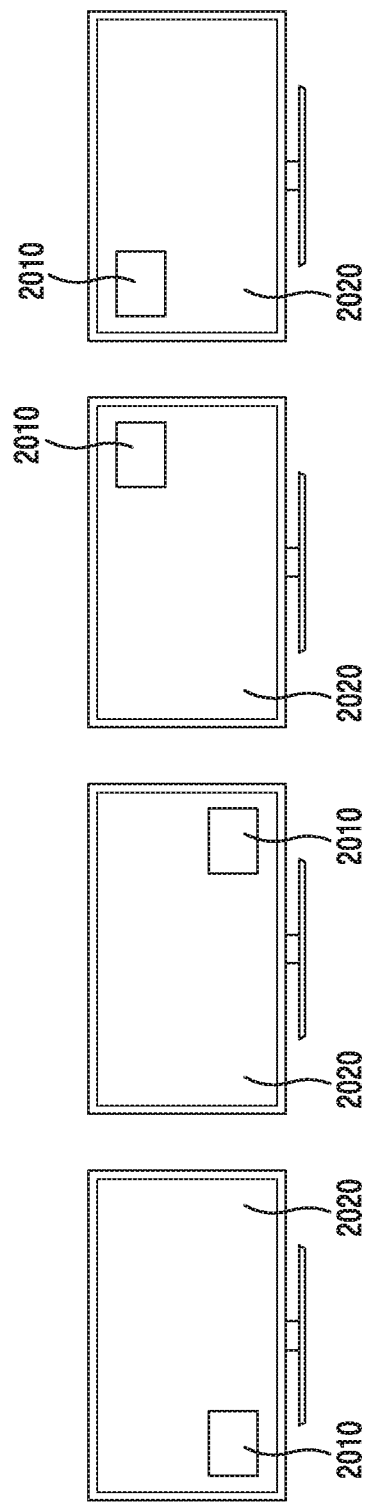
FIGS. 20A and 20B are diagrams illustrating the operation of providing a control image for a probe control guide according to various embodiments of the present disclosure.
Figure 20B:
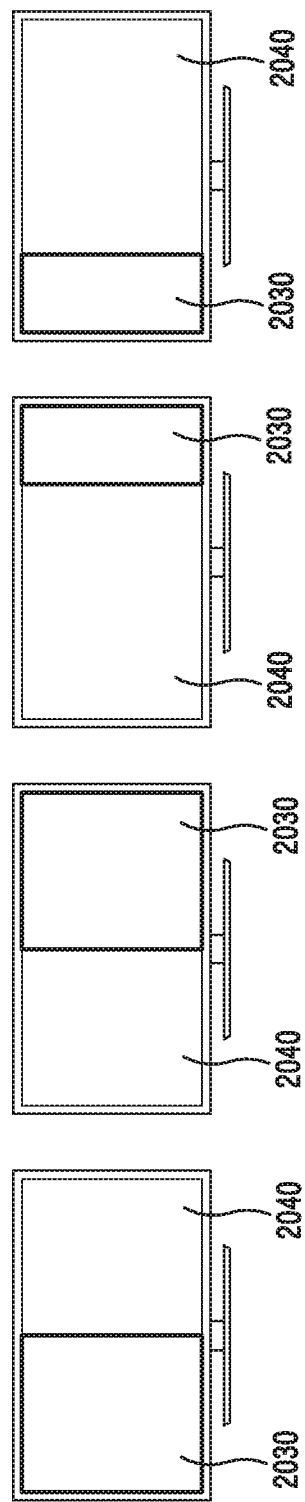

FIGS. 20A and 20B are diagrams illustrating the operation of providing a control image for a probe control guide according to various embodiments of the present disclosure.

Referring to FIGS. 20A and 20B, the second electronic device 500 may be connected to the first electronic device 400 in a distant place, and may display a control image 2010 of the probe 600 obtained by photographing in real time the control of the probe 600 through the camera (for example, the camera module 670 or the rear camera) of the first electronic device 400 on the basis of various GUIs.

According to an embodiment, as illustrated in FIG. 20A, the second electronic device 500 may provide the floating image 2010 (for example, affected part image as a preview image) photographed in real time, which is received from the first electronic device 400, in a partial area of the screen.

According to various embodiments, the GUI (for example, a pup-up window of the image 2010 photographed in real time, which is received from the first electronic device 400) may be provided in various forms such as rectangular, triangular, polygonal, and circular forms. According to various embodiments, the GUI may move according to user input. According to various embodiments, the GUI may be displayed through a window independent from an ultrasound image 2020 acquired from the first electronic device 400, and one window may be displayed in an overlap type such that the window overlaps at least the part of another window. For example, the second electronic device 400 may display the image 2010 photographed in real time on the ultrasound image 2020 through a particular type GUI (for example, a pop-up window) in a Picture In Picture (PIP) or a Picture By Picture (PBP) form.

According to various embodiments, the GUI may be located in one area (for example, an upper right part of the screen, an upper left part of the screen, a lower left part of the screen, or a lower right part of the screen) on the ultrasound image 2020 as illustrated in FIG. 20A. The GUI may be displayed in, for example, a bubble form. The size and location of the GUI may be changed by the user.

According to an embodiment, as illustrated in FIG. 20B, the second electronic device 400 may split the screen and provide an image 2030 photographed in real time (for example, affected part image data as a preview image), which is received from the first electronic device 400.

According to various embodiments, the GUI (for example, the image 2030 photographed in real time, which is received from the first electronic device 400) may be displayed through a window independent from an ultrasound image 2040 received from the first electronic device 400, and respective windows may be displayed to not overlap each other. For example, the second electronic device 400 may independently display the ultrasound image 2040 and the image 2030 photographed in real time on vertically or horizontally split screens.

According to various embodiments, the GUI may be located on a lower side or an upper side in the vertically split type or located on a left side or a right side in the horizontally split type as illustrated in FIG. 20B. According to various embodiments, the split screens may be implemented at the same ratio or different ratios. The size (for example, ratio) or location of the GUI may be changed by the user.

Figure 21:
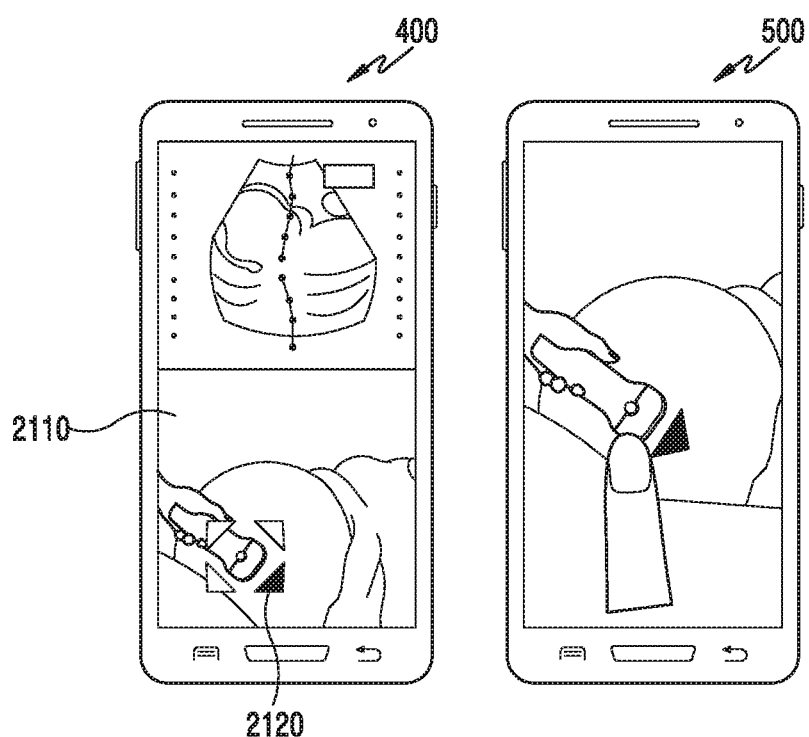
FIG. 21 is a diagram illustrating the operation of providing a probe control guide according to various embodiments of the present disclosure.

FIG. 21 is a diagram illustrating the operation of providing a probe control guide according to various embodiments of the present disclosure.

Referring to FIG. 21, the second electronic device 500 (for example, a smart phone) may provide guide information for guiding the control of the probe 600 to the first electronic device 400 based at least partially on user input.

According to various embodiments, as illustrated in FIG. 21, the second electronic device 500 may provide the ultrasound image acquired (received) from the first electronic device 400 and the photographed image together or provide an enlarged photographed image according to a user control. According to an embodiment, the second electronic device 500 may enlarge (for example, entire screen) and provide only the photographed image and the user may input a touch at a location for guiding a direction (or location movement) of the probe 600 in the photographed image (or enlarged photographed image). For example, the user may indicate a direction guide for guiding the probe 600 on the basis of touch input. The second electronic device 500 may generate guide information (for example, location information or direction information) corresponding to the touched area (for example, coordinates) on the basis of user input and transmit the generated guide information to the first electronic device 400.

According to various embodiments, the first electronic device 400 may provide an indicator 2120 by displaying the indicator 2120 at a location corresponding to the guide information of the second electronic device 500 on a photographed image 2110 in response to reception of the guide information from the second electronic device 500. According to an embodiment, the first electronic device 400 may provide the indicator 2120 by displaying the indicator 2120 in an area corresponding to touched area by the second electronic device 500 in the photographed area 2110.

Figure 22:
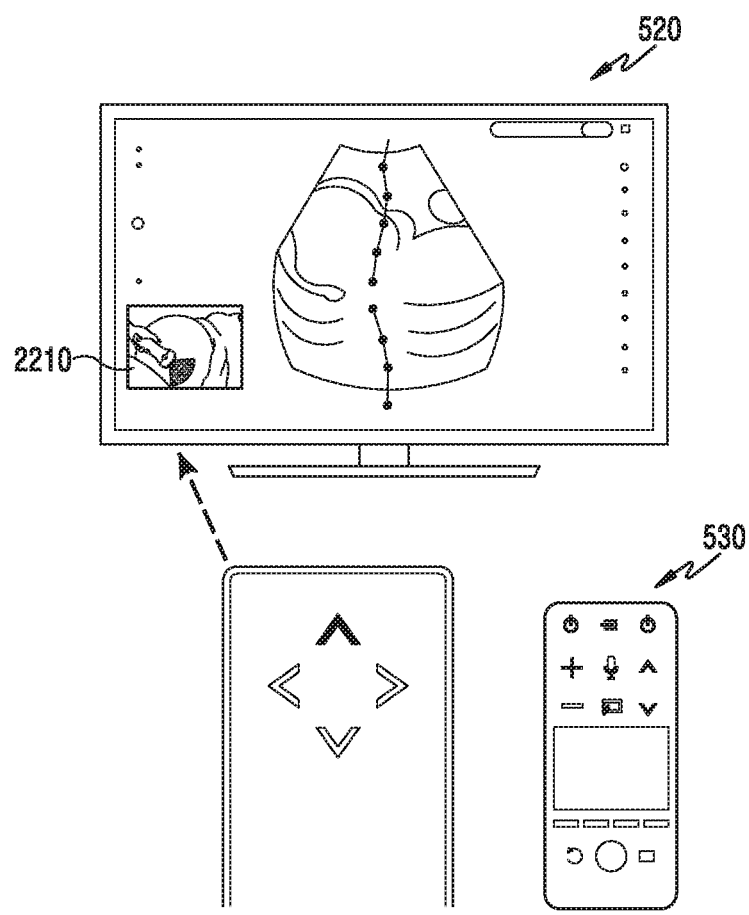
FIG. 22 is a diagram illustrating the operation of providing a probe control guide according to various embodiments of the present disclosure.

FIG. 22 is a diagram illustrating the operation of providing a probe control guide according to various embodiments of the present disclosure.

Referring to FIG. 22, the second electronic device 520 (for example, an external screen such as a TV or a monitor) may provide guide information for guiding the control of the probe 600 to the first electronic device 400 based at least partially on user input using the control device 530 (for example, the remote controller).

According to various embodiments, as illustrated in FIG. 22, the second electronic device 520 may provide the ultrasound image acquired (received) from the first electronic device 400 and the photographed image together or provide an enlarged photographed image according to a user control. According to an embodiment, the second electronic device 520 may enlarge only the photographed image and provide the enlarged photographed image. The user may control the control device 530 with respect to the location for guiding the direction (or location movement) of the probe 600 while identifying (viewing) the photographed image 2210 through the second electronic device 520. For example, the user may indicate the direction guide for guiding the probe 600 on the basis of the control of a direction key of the control device 530. The control device 530 may transmit a command corresponding to the selected direction key to the second electronic device 520, and the second electronic device 520 may provide an indicator in an area (location) corresponding to the command, in parallel to or sequentially with this, generate guide information (for example, location information or direction information) corresponding to the area (for example, coordinate) in which the indicator is provided in the first electronic device 400, and transmit the generated guide information to the first electronic device 400.

According to various embodiments, the first electronic device 400 may provide an indicator to the user by displaying the indicator at a location corresponding to guide information of the second electronic device 520 on the photographed image in response to reception of the guide information from the second electronic device 520. According to an embodiment, the first electronic device 400 may provide an indicator by displaying the indicator in an area corresponding to the area in which the indicator is displayed on the photographed image through the second electronic device 520.

Figure 23:
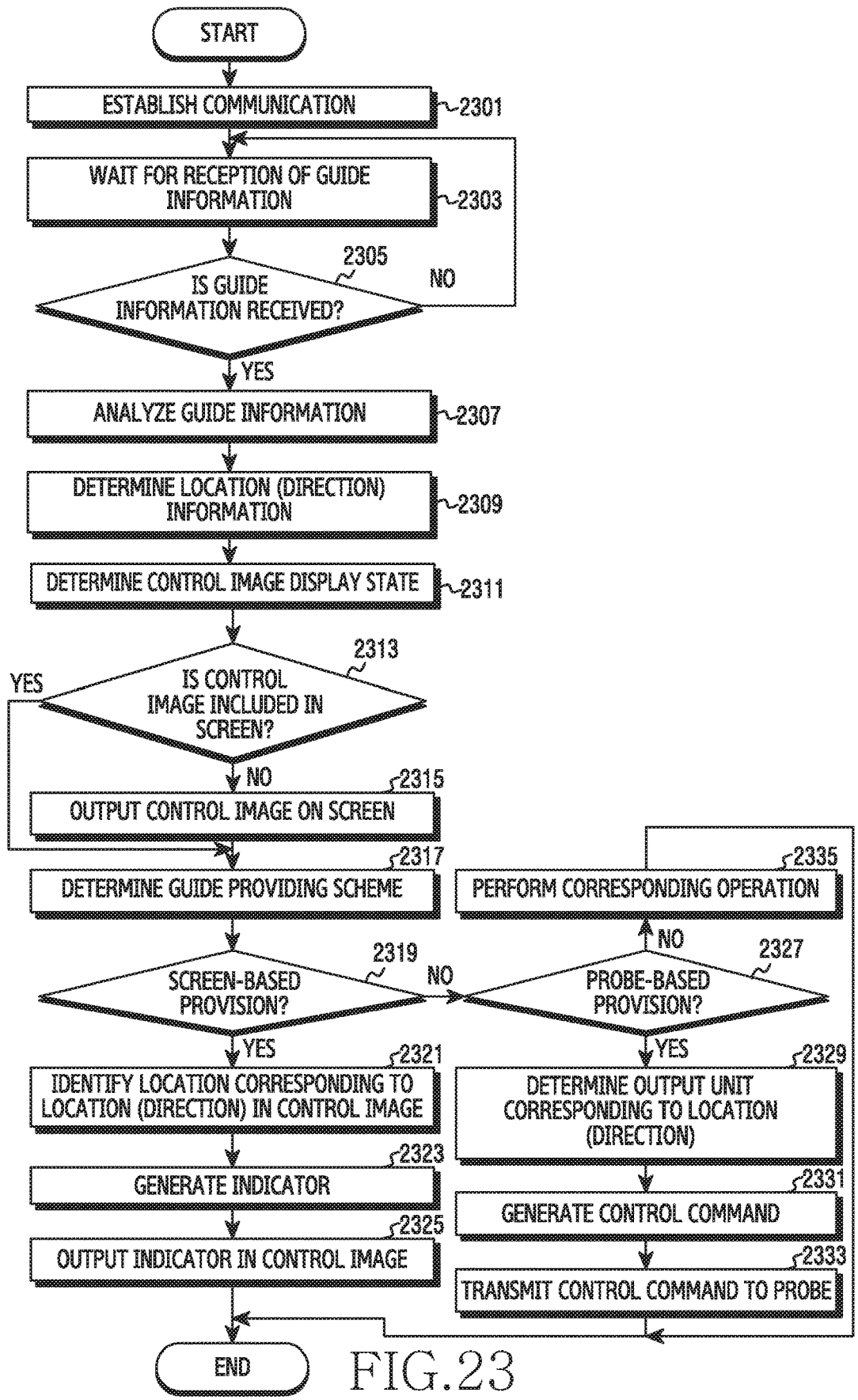
FIG. 23 is a flowchart illustrating the operation in which the electronic device guides a probe control according to various embodiments of the present disclosure.

FIG. 23 is a flowchart illustrating the operation in which the electronic device guides a probe control according to various embodiments of the present disclosure.

Referring to FIG. 23, in operation 2301, the controller 680 of the electronic device 400 may establish communication with an external device (for example, the second electronic device 500). According to an embodiment, the first electronic device 400 may connect a voice call or a video call with the configured second electronic device 500. According to various embodiments, the first electronic device 400 may transmit (for example, streaming) data related to the ultrasound image photographed by the probe 600 and the affected part control image photographed by the camera to the second electronic device 500.

When communication is connected, the controller 680 may wait for reception of guide information in operation 2303, and determine whether to receive the guide information in operation 2305. For example, the controller 680 may detect whether the guide information is received from the communication-connected counterpart electronic device (for example, the second electronic device 500).

When the reception of the guide information is not detected (No of operation 2305) in operation 2303, the controller 680 may proceed to operation 2303 and process operations after operation 2303.

When the reception of the guide information is detected (Yes of operation 2305) in operation 2303, the controller 680 may analyze the guide information in operation 2307. According to various embodiments, the guide information may include one or more pieces of location (direction) information related to location movement of the probe 600 and text or image information related to the control of the probe 600 or action on the patient.

In operation 2309, the controller 680 may determine location (direction) information included in the guide information based at least partially on the analysis of the received guide information. According to various embodiments, the location (direction) information may include information for guiding a location movement direction of the probe 600 connected to the electronic device 400.

The controller 680 may determine a control image display state in operation 2311, and determine whether the control image is included in the screen in operation 2313. For example, the controller 680 may determine whether the image currently displayed on the electronic device 400 is the ultrasound image (for example, ultrasound scan data) photographed by the probe 600, the control image of the probe 600 (for example, affected part image data) photographed by the camera (for example, the rear camera), or both the ultrasound image and the control image displayed together.

When the controller 680 identifies that the control image is included in the screen in operation 2313 (Yes of operation 2313), the controller 680 may proceed to operation 2317 and process operations after operation 2317. For example, the control image may be being displayed on the current screen or the ultrasound image and the control image may be being displayed together.

When the controller 680 identifies that the control image is not included in the screen in operation 2313 (No of operation 2313), the controller 680 may operate to output the control image on the screen in operation 2315. For example, only the ultrasound image may be being displayed on the current screen. According to an embodiment, the controller 680 may combine the ultrasound image and the control image and output the images by an overlay, PIP, or PBP form, or may output the images by switching the images from the ultrasound image to the control image.

In operation 2317, the controller 680 may determine a guide providing scheme. According to various embodiments, the guide providing scheme may include a first scheme for providing a guide on the basis of the screen of the electronic device 400, a second scheme for providing a guide on the basis of the output unit of the probe 600, and a third scheme for providing a guide on the basis of both the first scheme and the second scheme.

In operations 2319 and 2327, the controller 680 may determine whether the guide providing scheme is a screen providing scheme (operation 2319) or a probe-based providing scheme (operation 2327) on the basis of determination of the guide providing scheme. According to various embodiments, operations 2319 and 2327 may be performed in parallel, sequentially, or inversely.

When the controller 680 determines that the configured guide providing scheme is the screen-based providing scheme in operation 2319 (Yes of operation 2319), the controller 680 may identify a location corresponding to the location (direction) determined from the guide information in the control image in operation 2321.

In operation 2323, the controller 680 may generate an indicator. For example, the controller 680 may generate a configured type indicator for guiding the control of the probe 600. According to an embodiment, the indicator may be implemented in various forms such as an arrow, lighting, and a clock.

In operation 2325, the controller 680 may output the indicator in the control image. For example, the controller 680 may output the indicator in a predetermined location (or area) at which the direction can be indicated at the determined location or the corresponding location in the control image and guide a location movement direction of the probe 600.

When the controller 680 determines that the configured guide providing scheme is the probe-based providing scheme in operation 2327 (Yes of operation 2327), the controller 680 may determine at least one output unit corresponding to the location (direction) determined from the guide information among output units (for example, light emission devices) of the probe 600.

In operation 2331, the controller 680 may generate a control command. For example, the controller 680 may generate a control signal for controlling the output of the indicator by the output unit determined by the probe 600.

In operation 2333, the controller 680 may transmit the control command to the probe 600. According to an embodiment, the probe 600 may guide a location movement direction of the probe 600 through lighting by the corresponding output unit in response to reception of the control command from the electronic device 400. When the guide providing scheme is neither the first scheme based on the screen nor the second scheme based on the probe in operations 2319 and 2327, the controller 680 may determine that the guide providing scheme is, for example, the third scheme and process the corresponding operation in operation 2335. According to an embodiment, the controller 680 may process operations 2329 and 2333 in parallel to operations 2321 to 2325, and simultaneously output the indicator within the screen based thereon and output the indicator using the output unit of the probe 600 by transmission of the control command to the probe.

Figure 24:
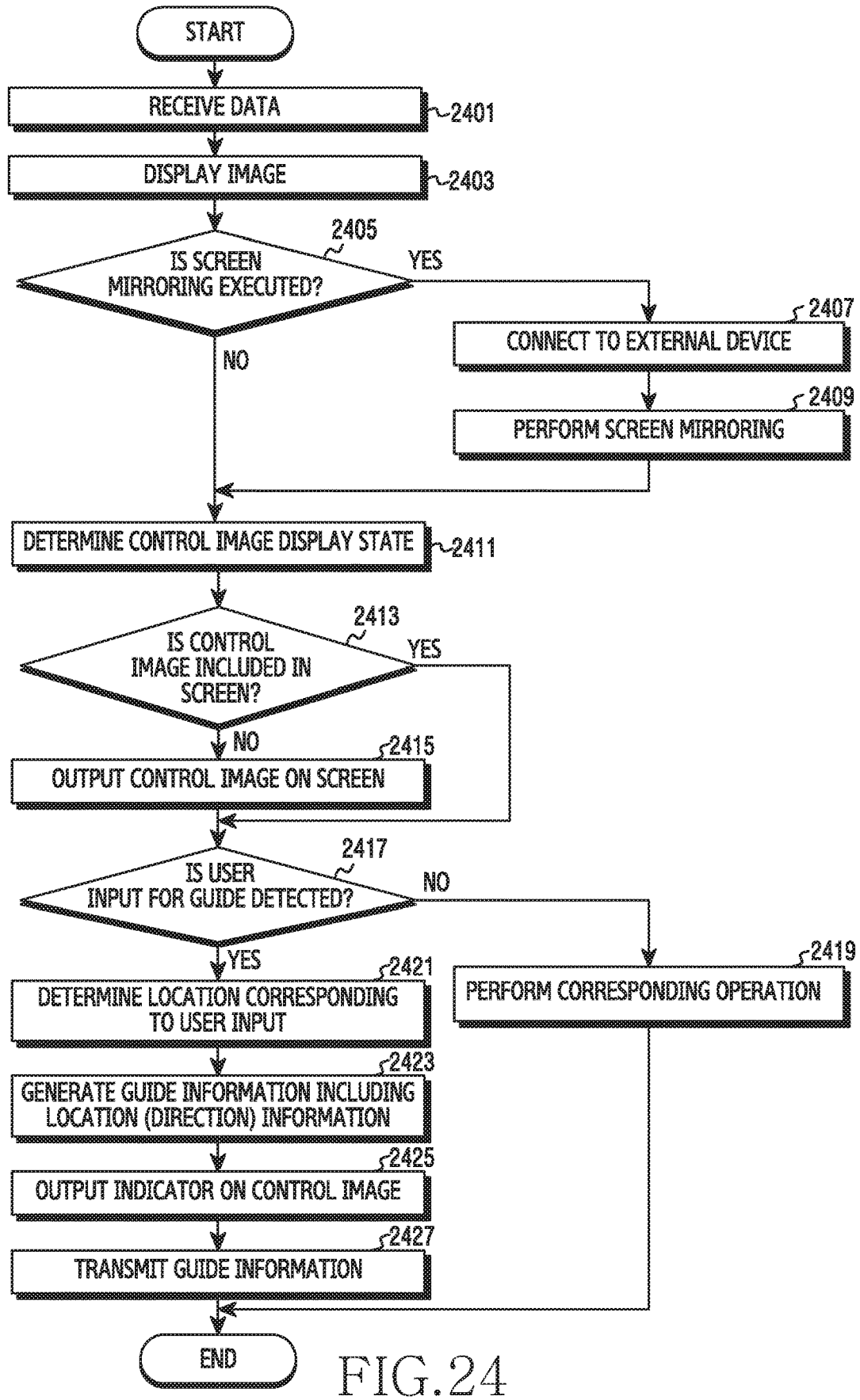
FIG. 24 is a flowchart illustrating the operation in which the electronic device guides the probe control according to various embodiments of the present disclosure.

FIG. 24 is a flowchart illustrating the operation in which the electronic device guides the probe control according to various embodiments of the present disclosure.

Referring to FIG. 24, in operation 240I, the controller 680 of the electronic device 500 may receive data from an external device. According to an embodiment, the second electronic device 500 may receive ultrasound scan data corresponding to the ultrasound image by the probe 600 or affected part image data corresponding to the control image by the camera of the first electronic device 400 from the first electronic device 400.

In operation 2403, the controller 680 may process the image display based at least partially on the received data. According to an embodiment, the controller 680 may display the ultrasound image, display the control image, or simultaneously display the ultrasound image and the control image based at least partially on the received data or configuration.

In operation 2405, the controller 680 may determine whether to execute screen mirroring. For example, the user may execute a screen mirroring function for sharing the displayed image with the external device (for example, an external screen such as a TV or a monitor).

When it is determined to execute the screen mirroring in operation 2405 (Yes of operation 2405), the controller 680 may connect to the external device in operation 2407.

According to an embodiment, the controller 680 may connect to the external device through a Wi-Fi Direct scheme or Wi-Fi Display scheme.

In operation 2409, the controller 680 may perform screen mirroring by transmitting the displayed image to the external device.

The controller 680 may determine a control image display state in operation 2411, and determine whether the control image is included in the current screen in operation 2413. For example, the controller 680 may determine whether the image currently displayed on the electronic device 500 is the ultrasound image (for example, ultrasound scan data) photographed by the probe 600, the control image of the probe 600 (for example, affected part image data) photographed by the camera (for example, the rear camera), or both the ultrasound image and the control image displayed together.

When the controller 680 identifies that the control image is included in the current screen in operation 2413 (Yes of operation 2413), the controller 680 may proceed to operation 2417 and process operations after operation 2417. For example, the control image may be being displayed on the current screen or the ultrasound image and the control image may be being displayed together.

When the controller 680 identifies that the control image is not included in operation 2413 (No of operation 2413), the controller 680 may output the control image on the screen in operation 2415. For example, only the ultrasound image may be being displayed on the current screen. According to an embodiment, the controller 680 may combine the ultrasound image and the control image and output the images in an overlay, PIP, or PBP form, or may output the images by switching the images from the ultrasound image to the control image.

In operation 2417, the controller 680 may determine whether user input for guiding the control of the probe 600 is detected.

When the user input is not detected in operation 2417 (No of operation 2417), the controller 680 may process the corresponding operation in operation 2419. According to an embodiment, the controller 680 may process the output of the image streaming-received from the first electronic device 400 and process a voice call or a video call with the first electronic device 400, or process various operations related to reading the ultrasound image independently or in parallel.

When the user input is detected in operation 2417 (Yes of operation 2417), the controller 680 may determine the location corresponding to the user input in operation 2421. According to an embodiment, the user may input a touch to the location for guiding a direction (or location movement) of the probe 600 in a real-time control image of the electronic device 500 as illustrated in FIG. 21. For example, the user may indicate a direction guide for guiding the probe 600 on the basis of touch input, and the controller 680 may determine the touch location. According to another embodiment, the user may control the electronic device 500 (or a separate control device (for example, a remote controller) with respect to the location for guiding the direction (or location movement) of the probe 600 while identifying (viewing) the control image through the external screen as illustrated in FIG. 22. For example, the user may indicate the direction guide for guiding the probe 600 on the basis of the control of a direction key of the electronic device or the control device, and the controller 680 may determine information such as a moved location (direction) or a change in movement in accordance with the controlled direction key.

In operation 2423, the controller 680 may generate guide information including the determined location (direction) information. According to various embodiments, the guide information may include one or more pieces of location (direction) information related to location movement of the probe 600 connected to the first electronic device 400 in a distant place and text or image information related to the control of the probe 600 or action on the patient.

In operation 2425, the controller 680 may process the output of the indicator in the control image. According to an embodiment, the controller 680 may output the indicator in the control image displayed on the electronic device 500 as illustrated in FIG. 21. According to another embodiment, the controller 680 may output the indicator in the control image displayed on the external device as illustrated in FIG. 22. According to another embodiment, the controller 680 may output the indicator in both the control image of the electronic device 500 and the control image of the external device.

In operation 2427, the controller 680 may transmit guide information. For example, the controller 680 may transmit guide information including location (direction) information to the first electronic device 400.

According to various embodiments, orders of the guide information generating operation, the guide information transmitting operation, and the indicator outputting operation corresponding to operations 2423 to 2427 are not limited to the above description, and the operations may be performed in parallel or simultaneously or the indicator outputting operation may be performed after the guide information transmitting operation is performed.

Hereinafter, according to various embodiments, the operation of executing a diagnosis mode based on context by the first electronic device 400 will be described.

Figure 25:
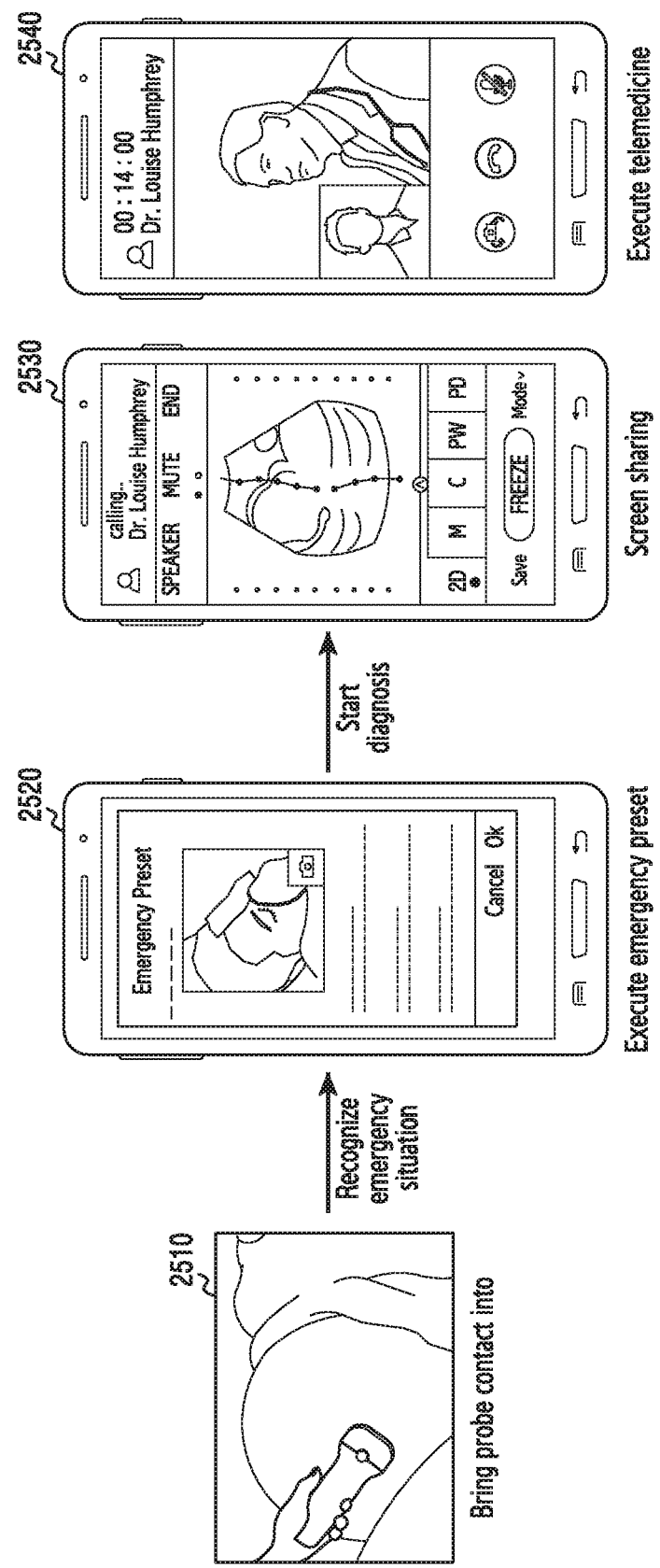
FIG. 25 is a diagram illustrating the operation in which the electronic device executes a diagnosis mode according to various embodiments of the present disclosure.

FIG. 25 is a diagram illustrating the operation in which the electronic device executes a diagnosis mode according to various embodiments of the present disclosure.

According to various embodiments, the user (for example, the paramedic) may operate the probe 600 and configure the probe 600 to start an emergency diagnosis on the basis of an action of putting the probe 600 on the patient's body. For example, the electronic device (for example, the first electronic device 400) may recognize the emergency diagnosis start in response to recognition of the state in which the probe 600 is operated and put on the patient's body, and automatically execute the emergency mode. That is, the electronic device may automatically execute the diagnosis mode on the basis of context awareness.

According to various embodiments, the electronic device may omit a preset configuration step and immediately execute an emergency preset in response to the execution of the emergency mode, and thus provide the performance of an emergency ultrasound diagnosis after configuring the emergency preset once.

Referring to FIG. 25, as illustrated in operation 2510, the user may bring the probe 600 into contact with the patient's body (for example, affected part) after operating the probe 600. The probe 600 may detect the contact on the patient's body and provide a detection signal according to the contact to the electronic device. Alternatively, the probe 600 may provide ultrasound scan data, which is scanned according to the contact on the patient's body, to the electronic device as a detection signal.

As illustrated in operation 2520, the electronic device may recognize the emergency diagnosis start in response to reception of the detection signal from the probe 600. According to an embodiment, the electronic device may recognize the emergency diagnosis start on the basis of context awareness by the probe 600 and automatically execute the emergency diagnosis mode in response to the awareness of the emergency diagnosis start. The electronic device may immediately execute the emergency preset when executing the emergency diagnosis mode according to the emergency diagnosis start. For example, the electronic device may display a user interface related to the emergency preset. According to various embodiments, the user interface related to the emergency preset may include a patient information area, a screen mirroring area, a communication area, and a menu area. When the camera is in an off state, the electronic device may operate the camera by performing control to turn on the camera (for example, supplying power to a camera driving circuit) in response to the execution of the emergency diagnosis mode.

According to various embodiments, the electronic device may transmit the ultrasound scan data by the probe 600 and the affected part image data by the camera to another electronic device. According to an embodiment, data transmission and emergency diagnosis mode execution may be performed in parallel or sequentially. For example, data acquired in accordance with the emergency diagnosis mode execution may be directly transmitted to another configured electronic device or the data may be transmitted on the basis of intended input for making a request for performing telemedicine to the user.

According to various embodiments, the electronic device may perform telemedicine by inserting a function according to user settings into the emergency preset. According to various embodiments, the screen mirroring function and/or the communication function selected by the user may be executed by user's selection. For example, when a request for performing telemedicine is made by the user (for example, a paramedic) who controls the electronic devices, data (for example, ultrasound scan data or affected part image data) may be transmitted to another electronic device. According to an embodiment, when the mirroring function is selected in the screen mirroring area, the electronic device may perform the mirroring operation by directly transmitting data to another configured electronic device (for example, an external device (for example, a TV or a monitor) in the hospital). According to an embodiment, when the communication function is selected in the communication area, the electronic device may perform a communication connection with another electronic device (for example, an electronic device of a doctor in the hospital) on the basis of a selected communication (for example, a voice call or a video call) scheme.

As illustrated in operation 2530 and operation 2540, when another electronic device receives data from the electronic device or communication is connected along with data reception, the other electronic device may display a user interface (operation 2540) (for example, a video call screen) related to telemedicine and may selectively display a user interface (operation 2530) related to mirroring (for example, screen sharing). According to an embodiment, another electronic device may display ultrasound scan data based at least partially on the received data. According to an embodiment, another electronic device may perform screen mirroring by linking (for example, connecting in real time) the received data with the external device (for example, a TV or a monitor).

Figure 26:
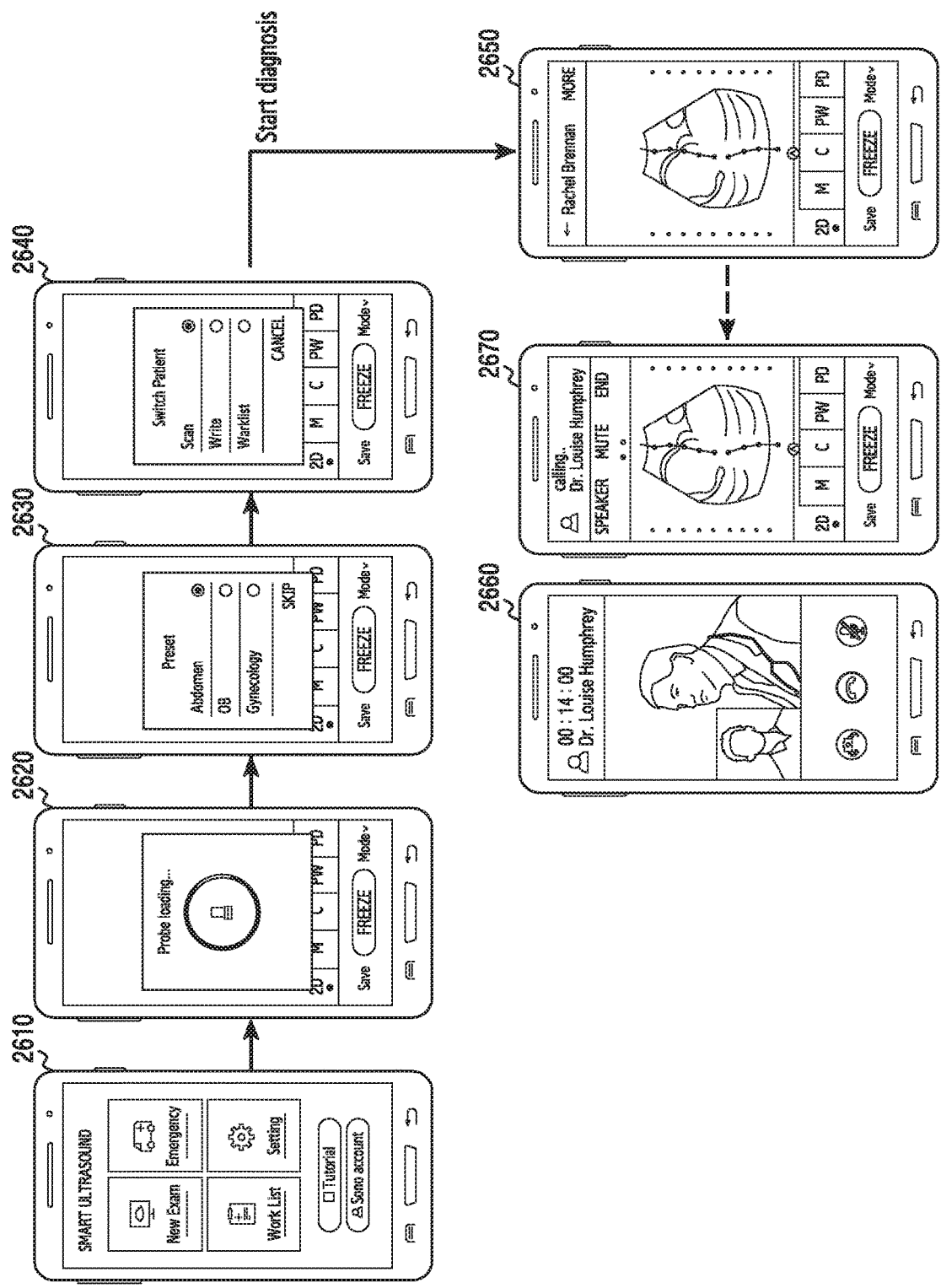
FIG. 26 is a diagram illustrating the operation of executing a diagnosis mode by the electronic device according to various embodiments of the present disclosure.

According to various embodiments, the emergency diagnosis mode execution is not limited to execution based on context awareness, but may be performed on the basis of various user inputs. The user inputs may include, for example, a status change in pose of the electronic device, a proximity status change, gesture input, context awareness, or voice command input. For example, types of event by which the electronic device detects switching to the emergency diagnosis mode may include at least one of voice recognition, context recognition, a motion or proximity change, execution of an application related to an emergency preset, a menu for image transmission, a key, a button, and gesture input. FIG. 26 is a diagram illustrating the operation of executing a diagnosis mode by the electronic device according to various embodiments of the present disclosure.

According to various embodiments, the basic diagnosis mode may be executed according to the normal process. For example, as illustrated in FIG. 26, the basic diagnosis mode may further include the preset configuration step compared to the emergency diagnosis mode by the emergency preset.

Referring to FIG. 26, as illustrated in a screen 2610, the user may display an ultrasound diagnosis menu by controlling (for example, by executing a relevant application (for example, SMART ULTRASOUND)) the electronic device. The user may connect the electronic device with the probe 600. According to an embodiment, in the case of a wireless connection scheme, the user may operate the probe 600 (for example, turn on power), and the probe 600 and the electronic device may be automatically connected to each other through an automatic pairing operation. According to an embodiment, in the case of a wired connection scheme, the user may connect the probe 600 to the electronic device by a wire through the corresponding interface of the electronic device, and the electronic device may recognize the connection of the probe 600 and automatically connect to the probe 600.

As illustrated in a screen 2620, the electronic device may provide a GUI related to various objects indicating probe loading statuses. Various objects may provide at least one of, for example, an item (for example, an animation icon) and notification text (for example, Make sure probe is located within 1 m away from Device) indicating a progress status (for example, Probe loading . . . ).

As illustrated in a screen 2630, the electronic device may provide a relevant GUI for configuring a diagnosis department. For example, the electronic device may provide a GUI for selecting a preset diagnosis department (for example, Abdomen, OB, and Gynecology) related to the ultrasound diagnosis in response to completion of the probe loading. According to an embodiment, the following step may be immediately performed by skipping the selection of the diagnosis department.

As illustrated in a screen 2640, the electronic device may provide a relevant GUI for inputting environment information. For example, the electronic device may provide a GUI related to inputting patient information or selecting an input type in response to the configuration or skipping of the diagnosis department. According to an embodiment, as illustrated in a screen 2640, the electronic device may provide a GUI for selecting Scan for inputting patient information by the scan, Write for inputting patient information by records, and Worklist for inputting patient information by list selection. According to an embodiment, the following step may be immediately performed without any selection process by performing cancellation.

The electronic device may start the ultrasound diagnosis on the basis of the preset configuration as described above. For example, as illustrated in a screen 2650, a screen 2660, and a screen 2670, like the scheme of performing the operation after configuring the emergency preset in FIG. 25, the electronic device and another electronic device may display a user interface (the screen 2670) related to telemedicine and may selectively display a user interface (the screen 2660) related to mirroring (for example, screen sharing).

According to various embodiments, the emergency diagnosis mode according to the emergency diagnosis start and the basic diagnosis mode according to the sequential process may be distinguished according to whether the preset configuration step is included or not. For example, in the emergency diagnosis mode, the preset configuration step may be omitted as illustrated in the screen 2610, the screen 2620, the screen 2630, and the screen 2640 of FIG. 26, and the emergency preset may be directly executed as illustrated in operation 2520 of FIG. 25.

Figure 27:
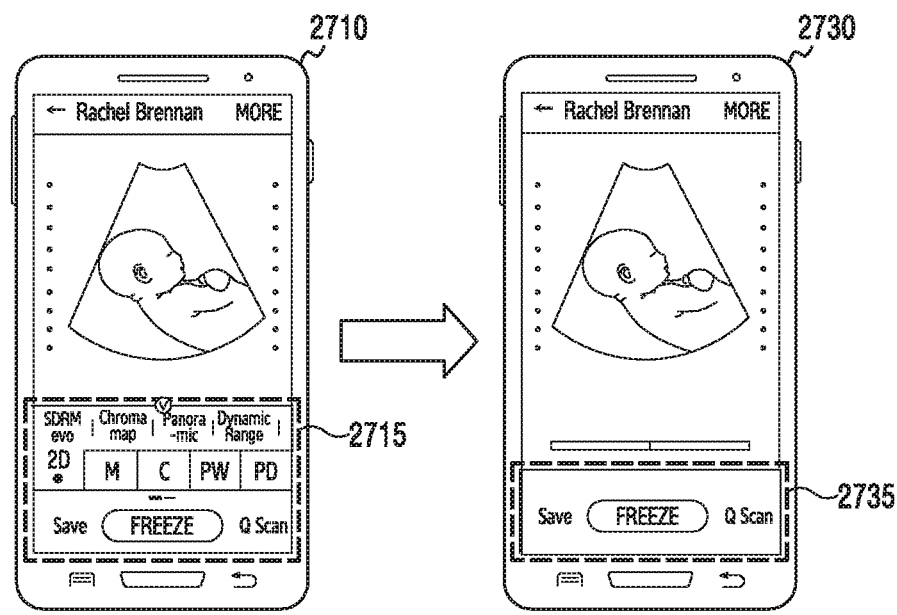
FIG. 27 is a diagram illustrating the operation in which the electronic device executes a diagnosis mode according to various embodiments of the present disclosure.

FIG. 27 is a diagram illustrating the operation in which the electronic device executes a diagnosis mode according to various embodiments of the present disclosure.

Referring to FIG. 27, the electronic device may provide different GUIs according to execution of the basic diagnosis mode and the emergency diagnosis mode. For example, when entering the emergency diagnosis mode, the electronic device may simplify menus to display only minimum core menus (main menus) for a rapid ultrasound diagnosis in an emergency situation and provide the main menu to the user.

A screen 2710 may indicate a screen example when the electronic device enters the basic diagnosis mode according to various embodiments. As illustrated in the screen 2710, in the basic diagnosis mode, detailed menus 2715 including the main menus (for example, Freeze, Save, and Q Scan) and sub menus (for example, a Mode button and a Measure button) may be provided to handle various diagnosis cases. For example, five modes and four measurement menus may be provided.

A screen 2730 may indicate a screen example when the electronic device enters the emergency diagnosis mode according to various embodiments. As illustrated in the screen 2730, in the emergency diagnosis mode, simple menus 2735 may be provided such that only the main menus (for example, Freeze, Save, and Q Scan) are exposed in order to perform a rapider diagnosis and prevent undesired screen switching or function execution due to control mistake in the emergency situation.

Figure 28:
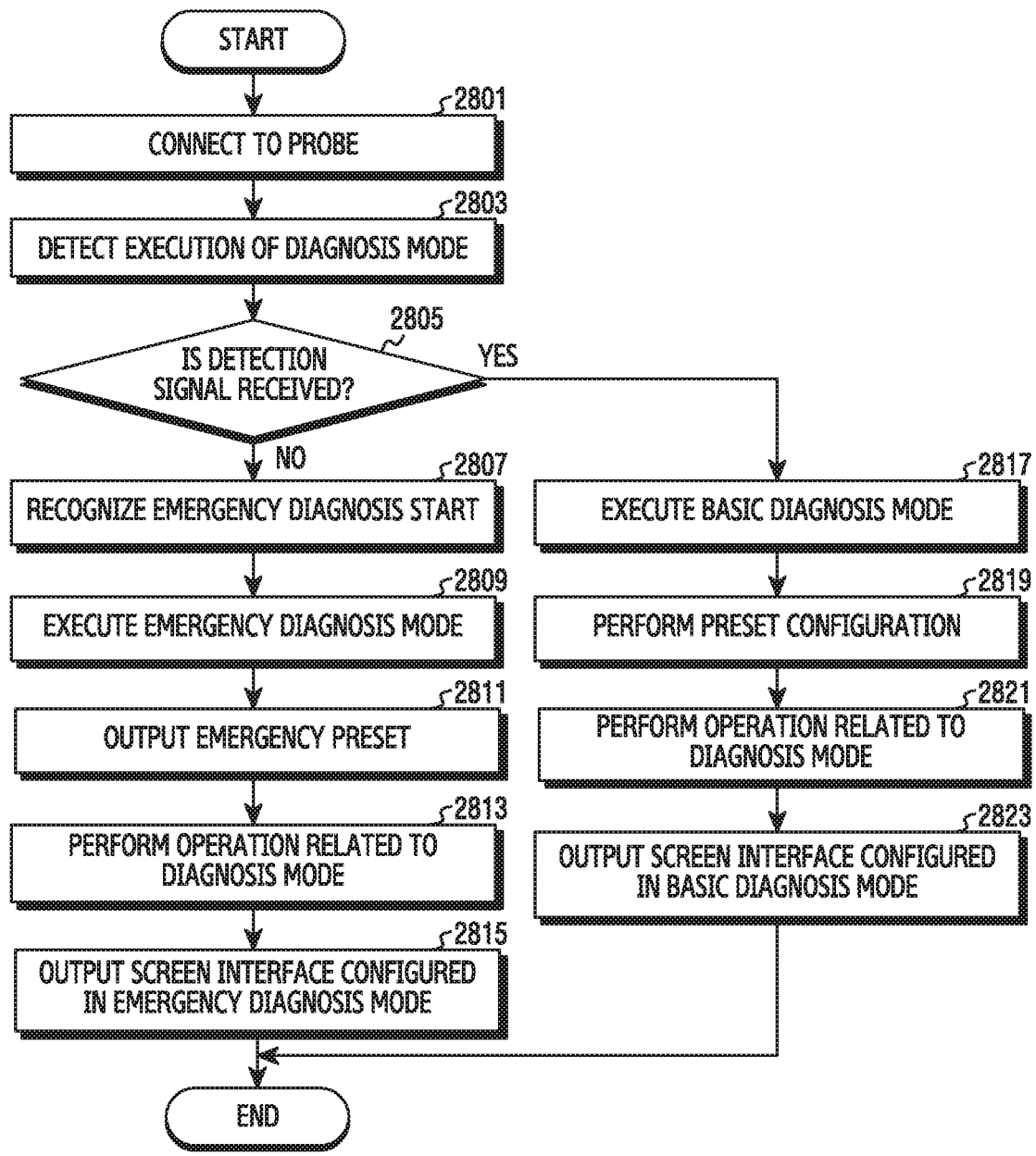
FIG. 28 is a flowchart illustrating the operation in which the electronic device executes the diagnosis mode according to various embodiments of the present disclosure.

FIG. 28 is a flowchart illustrating the operation in which the electronic device executes the diagnosis mode according to various embodiments of the present disclosure.

Referring to FIG. 28, in operation 2801, the electronic device 400 may be connected to the probe 600. According to various embodiments, the electronic device 400 and the probe 600 may be connected to each other on the basis of wired communication or wireless communication. According to an embodiment, in the case of wireless communication, the electronic device 400 and the probe 600 may be automatically connected through direct pairing based on the operation (for example, power on) of the probe 600 in a space in which they are close to each other. According to an embodiment, in the case of wired communication, the electronic device 400 and the probe 600 may be connected to a corresponding interface unit on the basis of a cable.

In operation 2803, the controller 680 of the electronic device 400 may detect execution of the diagnosis mode. According to various embodiments, the execution of the diagnosis mode may include execution of the emergency diagnosis mode and execution of the basic diagnosis mode as described with reference to FIGS. 25 and 26.

When the execution of the diagnosis mode is detected, the controller 680 may determine whether the execution of the diagnosis mode is execution of the diagnosis mode by reception of the detection signal from the probe 600 or execution of the diagnosis mode based on user input such as execution of an application or performance of the normal process in operation 2805.

When the diagnosis mode by reception of the detection signal is determined in operation 2805 (Yes of operation 2805), the controller 680 may recognize an emergency diagnosis start in operation 2807. For example, as illustrated in FIG. 25, when the user operates the probe 600 and then puts the probe 600 on the patient's body (for example, affected part), the probe 600 may detect the contact on the patient's body and provide the detection signal according to the contact to the electronic device 400. Alternatively, the probe 600 may provide ultrasound scan data, which is scanned according to the contact on the patient's body, to the electronic device as a detection signal. The controller 680 may recognize the emergency diagnosis start in response to reception of the detection signal from the probe 600. According to an embodiment, the controller 680 may recognize the emergency diagnosis start on the basis of context awareness by the probe 600.

In operation 2809, the controller 680 may execute the diagnosis mode on the basis of the emergency diagnosis mode. For example, the controller 680 may automatically execute the emergency diagnosis mode in response to the recognition of the emergency diagnosis start.

In operation 2811, the controller 680 may output the emergency preset. According to an embodiment, the controller 680 may directly execute the emergency preset when executing the emergency diagnosis mode according to the emergency diagnosis start. For example, the controller 680 may display a user interface related to the emergency preset as described with reference to FIGS. 10 and 25. According to various embodiments, the user interface related to the emergency preset may include a patient information area, a screen mirroring area, a communication area, and a menu area. According to an embodiment, when the camera is in an off state, the controller 680 may operate the camera by performing control to turn on the camera (for example, supplying power to a camera driving circuit) in response to the execution of the emergency diagnosis mode.

In operation 2813, the controller 680 may process the operation related to the performance of the diagnosis mode. For example, the controller 680 may process one or more operations such as data transmission, screen mirroring, and call connection to the external device (for example, the second electronic device 500).

In operation 2815, the controller 680 may process the output of a screen interface configured in the emergency diagnosis mode. According to an embodiment, as illustrated in FIG. 27, the controller 680 may provide simple menus by exposing only the screen interface configured in the emergency diagnosis mode, for example, only the main menus (for example, Freeze, Save, and Q Scan).

When the execution of the diagnosis mode based on the user input is determined in operation 2805 (No of operation 2805), the controller 680 may execute the diagnosis mode on the basis of the basic diagnosis mode in operation 2817.

In operation 2819, the controller 680 may perform the preset configuration step. According to an embodiment, as illustrated in FIG. 26, the controller 680 may perform the operation of configuring the preset related to the ultrasound diagnosis on the basis of an interaction with the user.

In operation 2821, the controller 680 may process the operation related to the performance of the diagnosis mode. For example, the controller 680 may process one or more operations such as data transmission, screen mirroring, and call connection to the external device (for example, the second electronic device 500).

In operation 2823, the controller 680 may process the output of a screen interface configured in the basis diagnosis mode. According to an embodiment, the controller 680 may provide detailed menus including the main menus (for example, Freeze, Save, and Q Scan) and sub menus (for example, a Mode button and a Measure button) in order to handle various diagnosis cases.

Hereinafter, according to various embodiments, the operation of providing a communication mode between users (for example, a doctor and a patient) in an ultrasound diagnosis will be described.

Figure 29:
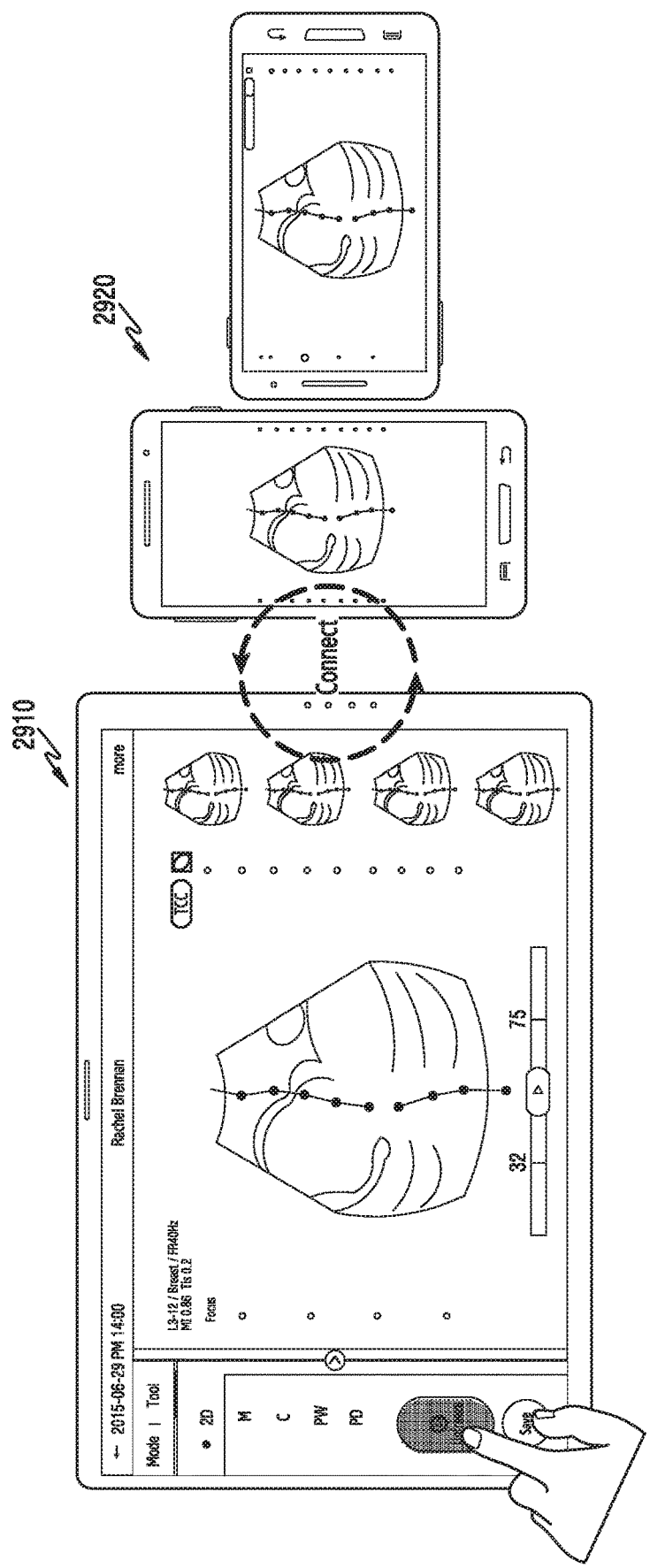
FIG. 29 is a diagram illustrating the operation of sharing data on the basis of screen mirroring between electronic devices according to various embodiments of the present disclosure.

FIG. 29 is a diagram illustrating the operation of sharing data on the basis of screen mirroring between electronic devices according to various embodiments of the present disclosure.

According to various embodiments, when a user (for example, a doctor) provides an ultrasound outpatient service, the user may perform communication with the patient (for example, transfer the detailed content of treatment to the patient) on the basis of screen mirroring of the electronic device. According to an embodiment, the electronic device may provide a screens sharing mode to another electronic device.

Referring to FIG. 29, through a connection between an electronic device 2910 (for example, a tablet PC) (hereinafter, referred to as a first electronic device 2910) of a first user (for example, a doctor) and an electronic device 2920 (for example, a smart phone) (hereinafter, referred to as a smart phone) of a second user (for example, a patient), a screen related to the ultrasound treatment may be shared. According to an embodiment, in the ultrasound treatment, the first user may connect (for example, pair) the first electronic device 2910 of the first user with the second electronic device 2920 of the second user through authentication of the second user (for example, authentication of the patient). When the first electronic device 2910 is connected to the second electronic device 2920, the first electronic device 2910 may share the ultrasound image by transmitting (for example, screen mirroring) the ultrasound image to the second electronic device 2920.

Figure 30:
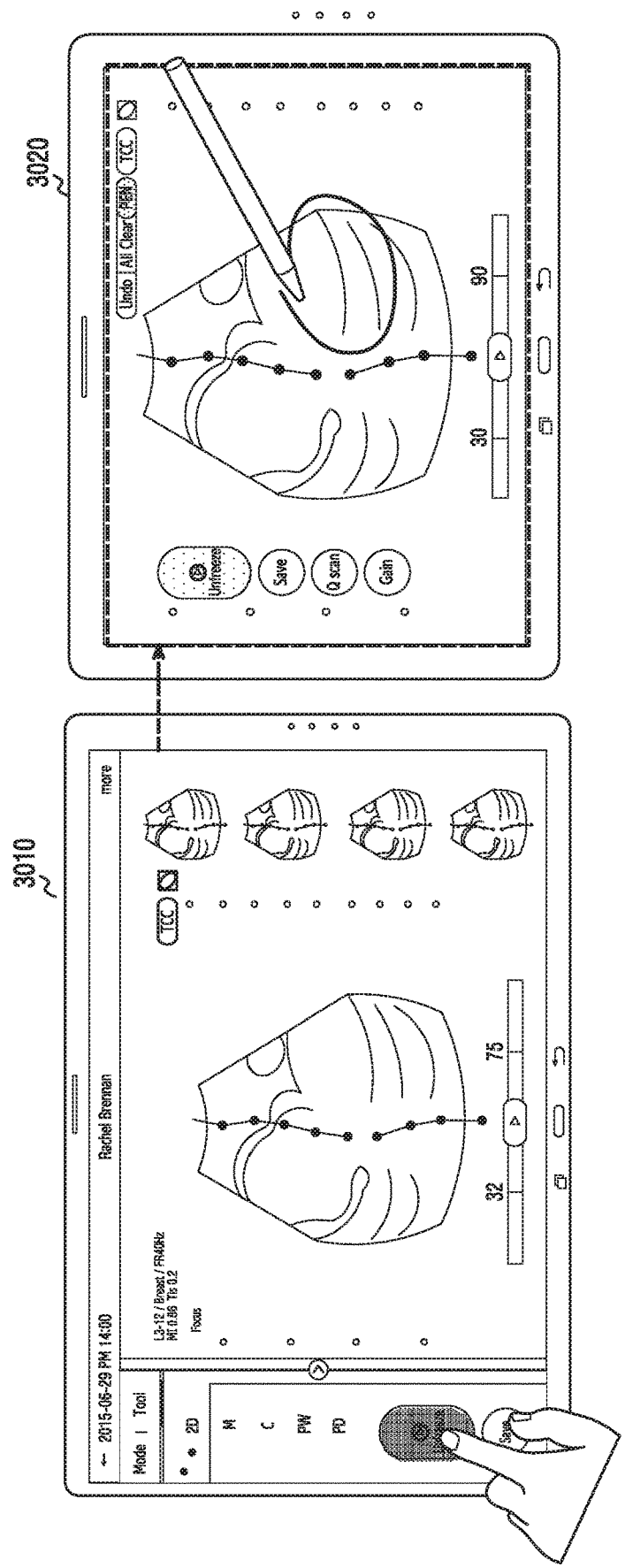
FIG. 30 is a diagram illustrating the operation in which the electronic device shares data by communication mode switching according to various embodiments of the present disclosure.

The second user may conveniently identify the screen (for example, the ultrasound image) of the first electronic device 2910 regardless of (without regard to) pose through the second electronic device 2920 which is a personal device of the second user. As described above, the second electronic device 2920 may recognize the orientation of the second electronic device 2920 and display the ultrasound image on the basis of the landscape mode or the portrait mode corresponding to switching of the orientation. According to various embodiments, screens displayed on the first electronic device 2910 and the second electronic device 2920 may be differently implemented. For example, the first electronic device 2910 may display all expert diagnosis menus and the second electronic device 2920 may hide the expert diagnosis menus and display the ultrasound image to be large. Additionally or alternatively, the first electronic device 2910 and/or the second electronic device 2920 may provide a drawing tool FIG. 30 is a diagram illustrating the operation in which the electronic device shares data by communication mode switching by according to various embodiments of the present disclosure.

According to various embodiments, the first user (for example, the doctor) may perform a treatment by sharing a screen with the second user (for example, the patient) through Point-Of-Care (POC) using the electronic device. According to various embodiments, when the treatment is performed while the first user and the second user share the screen through the POC, communication may be provided by switching the electronic device from the diagnosis mode to the communication mode.

As illustrated in a screen 3010, the first user may identify an ultrasound image by operating the electronic device in the basic diagnosis mode including all expert diagnosis menus.

As illustrated in a screen 3020, when the first user explains the ultrasound image while sharing (identifying together) the screen with the second user, the first user may switch the basic diagnosis mode of the electronic device to the communication mode.

According to various embodiments, the first user may select a switching button 3050 configured to switch to the communication mode in the electronic device. When user input by the switching button is detected, the electronic device may switch from the basic diagnosis mode to the communication mode and display a corresponding GUI. For example, the electronic device may enlarge and provide the ultrasound image and provide only information required for the patient. According to an embodiment, when the basic diagnosis mode is switched to the communication mode, the electronic device may hid the expert diagnosis menus, display the ultrasound image to be large, and additionally provide a drawing tool for memo or drawing. According to an embodiment, the first user may provide an intuitively explain related to the treatment to the second user through memo input or drawing on the displayed ultrasound image through the drawing tool.

Figure 31:
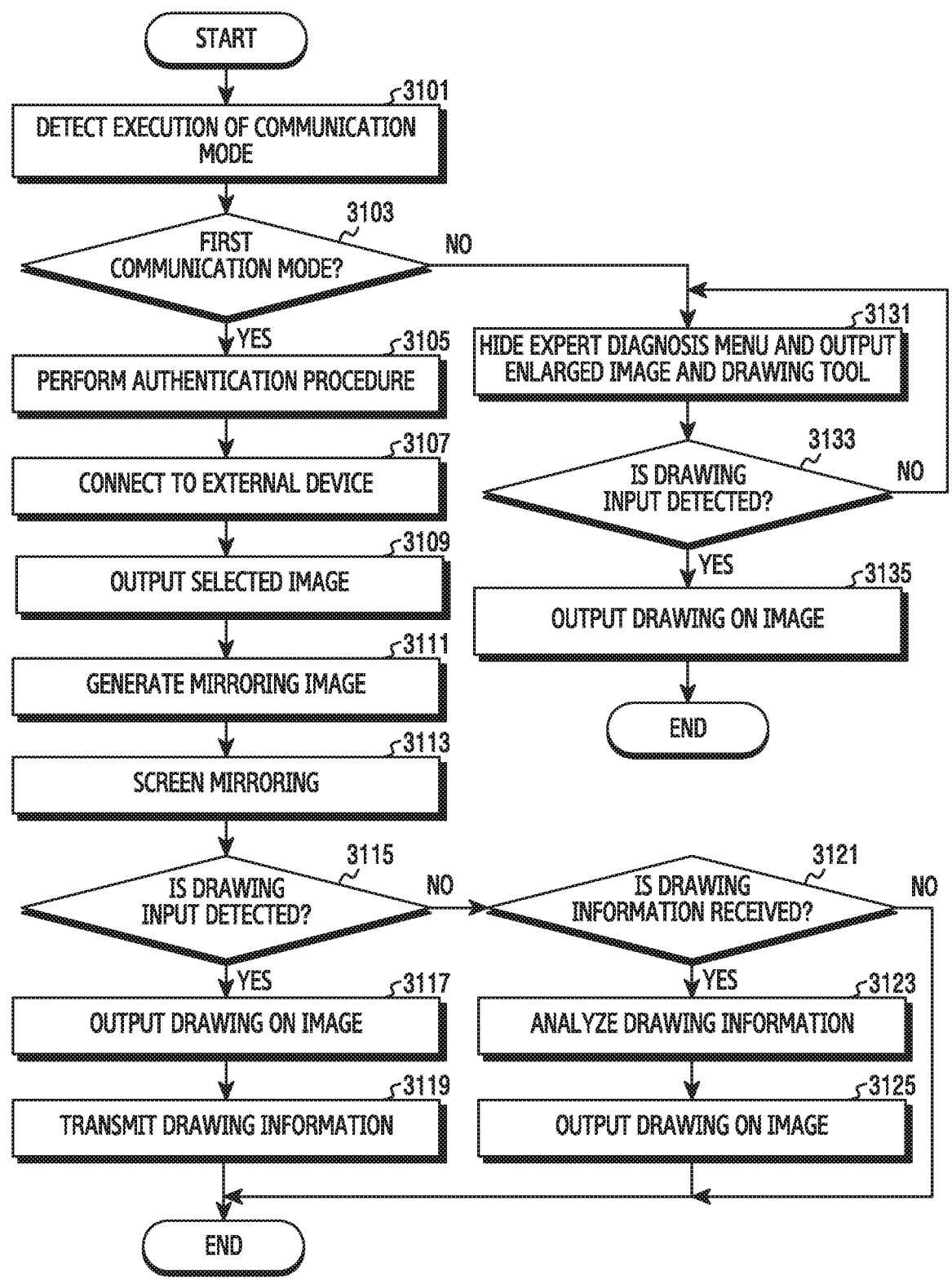
FIG. 31 is a flowchart illustrating the operation in which the electronic device provides the communication mode according to various embodiments of the present disclosure.

FIG. 31 is a flowchart illustrating the operation in which the electronic device provides the communication mode according to various embodiments of the present disclosure.

Referring to FIG. 31, in operation 3101, the controller 680 of the electronic device 500 may detect execution of the communication mode. For example, the first user (for example, the doctor) may control the electronic device 500 to execute the communication mode in order to share the diagnosis screen with the second user (for example, the patient) as described with reference to FIG. 29 or 30.

In response to detection of execution of the communication mode, the controller 680 may determine whether the execution of the communication mode is execution of a first communication mode or execution of a second communication mode in operation 3103. According to various embodiments, the first communication mode may include a mode of sharing the screen on the basis of the connection with another electronic device as illustrated in FIG. 29. According to various embodiments, the second communication mode may include a mode of sharing the screen by screen switching based on the electronic device as illustrated in FIG. 30.

When the controller 680 determines that the execution of the communication mode is execution of the second communication mode in operation 3103 (No of operation 3103), the controller 680 may execute the second communication mode on the basis of hiding the expert diagnosis menus and outputting the enlarged image and the drawing tool in operation 3131. For example, as illustrated in FIG. 30, when the controller 680 detects the execution of the second communication mode by the selection of the switching button in the screen including all expert diagnosis menus, the controller 680 may hide the expert diagnosis menus, enlarge and display the ultrasound image, and switch to and provide the screen including the drawing tool for memo or drawing.

In operation 3133, the controller 680 may determine whether there is drawing input. For example, the controller 680 may detect whether there is user input based at least partially on the drawing tool. According to an embodiment, the drawing input may include one or more of text (for example, handwriting), drawing, and marker input.

When the drawing input is not detected in operation 3133 (No of operation 3133), the controller 680 may process operations after operation 3131.

When the drawing input is detected in operation 3133 (Yes of operation 3133), the controller 680 may output drawing on the image in operation 3135. According to an embodiment, the controller 680 may display one or more drawing objects among text, a figure, and a marker in accordance with the user's drawing input on the image.

When the controller 680 determines that the execution of the communication mode is execution of the first communication mode in operation 3103 (Yes of operation 3103), the controller 680 may perform an authentication process in operation 3105. For example, the first user may select information on a particular second user or an ultrasound image related to the second user by controlling the electronic device 500. Alternatively, the user may perform control to share the ultrasound image currently displayed on the electronic device 500. In the first communication mode, the controller 680 may search for or determine an external device corresponding to the second user on the basis of input of the first user and perform an authentication process for the connection with the corresponding external device. According to various embodiments, the authentication process may include an information input procedure such as patient information input or external device information input by the first user and also an authentication procedure for the connection between the electronic device 600 and the external device based at least partially on the input information.

In operation 3107, the controller 680 may connect to the external device. According to an embodiment, the controller 680 may connect to the external device through a Wi-Fi Direct scheme or Wi-Fi Display scheme. According to another embodiment, the controller 680 may connect to the external device on the basis of short-range wireless communication such as Bluetooth.

In operation 3109, the controller 680 may output a selected image. For example, the controller 680 may display an ultrasound image, which is photographed in real time by the probe 600, or display an ultrasound image related to the second user stored in the electronic device 400 according to selection of the first user. According to various embodiments, the controller 680 may recognize the orientation of the electronic device 500 and display the image in the landscape mode or the portrait mode according to switching of the orientation.

In operation 3111, the controller 680 may generate a mirroring image to be shared with the external device. According to various embodiments, the mirroring image may be generated based at least partially on the ultrasound image. For example, the controller 680 may implement the screens such that the screen displayed on the electronic device 500 is different from the screen to be displayed on the external device. According to an embodiment, as illustrated in FIG. 29, the controller 680 may provide the screen including both the ultrasound image and the expert diagnosis menus in the electronic device 500 and provide the screen to be shared with the external device such that the expert diagnosis menus are hidden and only the ultrasound image is displayed to be large.

In operation 3113, the controller 680 may perform screen mirroring based on the generated mirroring image. For example, the controller 680 may transmit the generated mirroring image to the external device.

In operations 3115 and 3121, the controller 680 may determine whether there is drawing input (operation 3115) or there is reception of drawing information (operation 3121). According to various embodiments, the first user of the electronic device 500 or the second user of the external device may perform drawing input based at least partially on the drawing tool. According to an embodiment, the first user may perform drawing input using the first electronic device 500. According to another embodiments, the second user may perform the drawing input using the external device, and the external device may transmit relevant drawing information (for example, drawing type, form, location information, and path information) to the electronic device 500 in accordance with the drawing input of the second user.

When the drawing input is detected in operation 3115 (Yes of operation 3115), the controller 680 may output drawing on the image in operation 3117. According to an embodiment, the controller 680 may display one or more drawing objects among text, a figure, and a marker in accordance with the user's drawing input on the image.

In operation 3119, the controller 680 may transmit relevant drawing information corresponding to the drawing input to the external device. The external device may receive drawing information from the electronic device 500 and identically provide drawing objects, which are the same as the drawing objects displayed on the electronic device 500, at the location corresponding to the image.

When reception of the drawing information is detected in operation 3121 (Yes of operation 3121), the controller 680 may analyze the drawing information in operation 3123. For example, the controller 680 may determine drawing type, form, location information, or path information.

In operation 3125, the controller 680 may output drawing on the image. According to an embodiment, the controller 680 may identically provide drawing objects, which are the same as the drawing objects displayed on the external device, at the location corresponding to the image on the basis of the drawing information.

When the drawing input or reception of the drawing information is not detected in operation 3115 or 3121 (No of operation 3115 or No of operation 3121), the controller 680 may process the corresponding operation. According to an embodiment, the controller 680 may process the operation corresponding to output of the user interface or transmission of relevant control information to the external device according to input related to the diagnosis of the first user.

Hereinafter, according to various embodiments, various screen interfaces (for example, UIs or GUIs) provided by the electronic device will be described.

Figure 32:
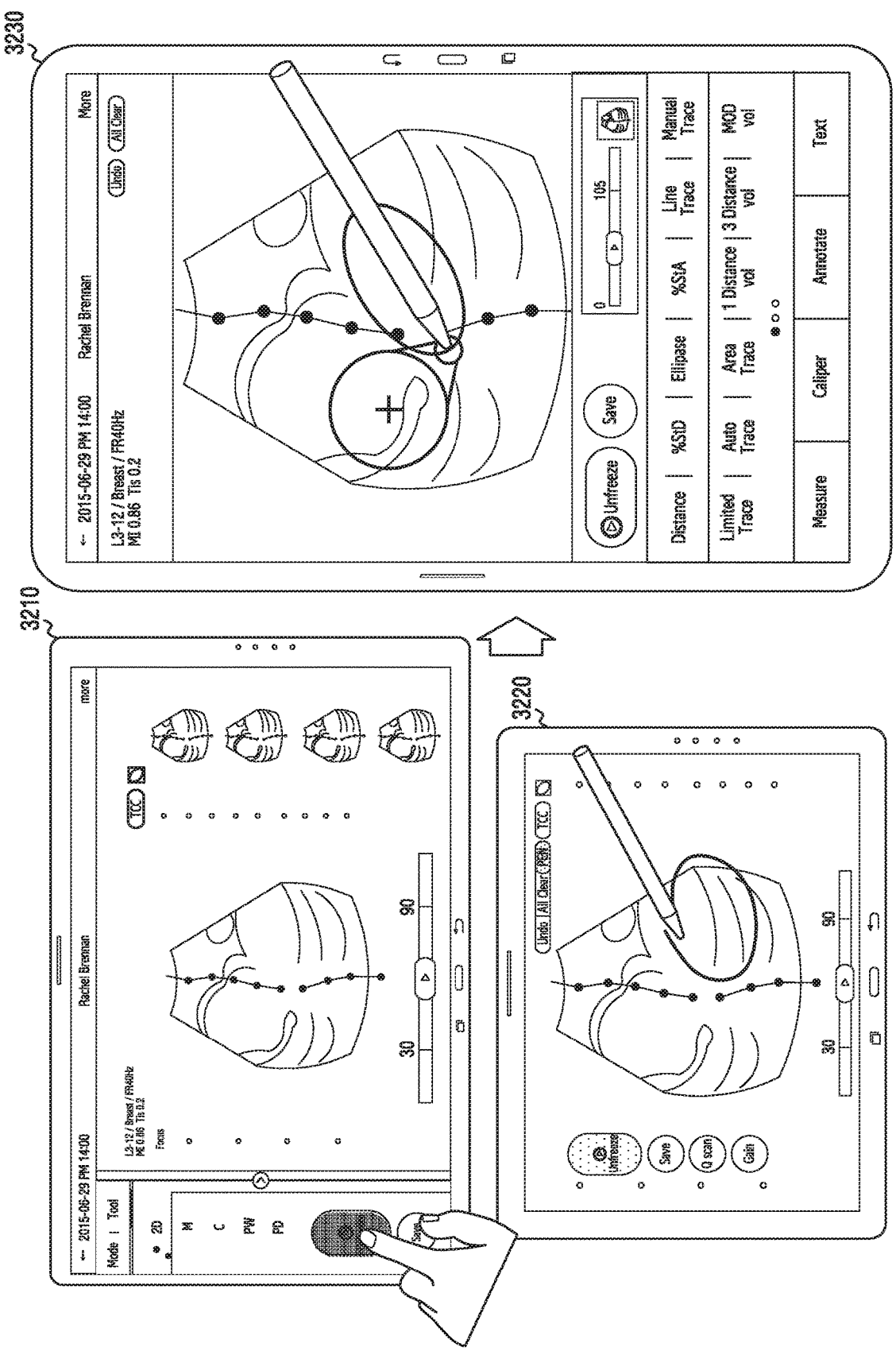
FIG. 32 illustrates an example of a screen interface provided based on screen orientation of the electronic device according to various embodiments of the present disclosure.

FIG. 32 illustrates an example of a screen interface provided based on screen orientation of the electronic device according to various embodiments of the present disclosure.

As illustrated in FIG. 32, FIG. 32 illustrates the case in which the electronic device is a tablet PC. According to various embodiments, a mode specific for the orientation of the electronic device may be provided.

Referring to FIG. 32, the electronic device may configure and provide landscape modes 3210 and 3220 in the basic diagnosis mode and configure and provide a precise reading mode in a portrait mode 3230. For example, the electronic device may display a user interface related to the basic diagnosis mode in the landscape mode 3210 or 3220 to provide the user interface to the user. When switching the screen from the landscape mode 3210 or 3220 to the portrait mode 3230, the electronic device may switch from the basic diagnosis mode to the precise reading mode and display a user interface related to the precise reading mode to provide the user interface to the user.

According to various embodiments, when switching the screen from the landscape mode to the portrait mode according to switching of the orientation, the electronic device may enlarge and provide the ultrasound image, activate tool menus, and expose and provide 2 depth menus related to measurement, which are not provided (for example, which are hidden) in the landscape mode. The tool menus may include, for example, Measure, Caliper, Annotate, and Text. The 2 depth menus may include, for example, Distance, % Std, Ellipse, and M distance. According to various embodiments, the 2 depth menus may be provided as a variable area. For example, the menus may be changed according to context, or may be provided in an open/close form.

According to various embodiments, the tool menus and the 2 depth menus will be described with reference to the drawings below.

According to various embodiments, the electronic device may detect orientation switching (or rotation) of the electronic device. For example, switching from the portrait mode to the landscape mode or switching from the landscape mode to the portrait mode may be determined. The electronic device may switch and provide a corresponding specific mode on the basis of the determined mode.

Figure 33:
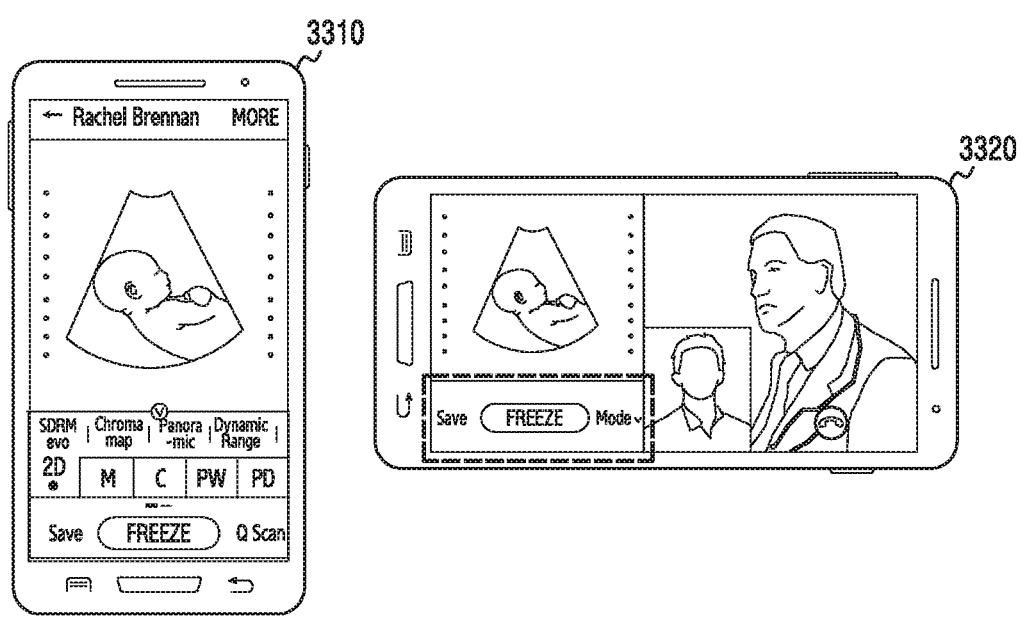
FIG. 33 illustrates an example of a screen interface provided based on screen orientation of the electronic device according to various embodiments of the present disclosure.

FIG. 33 illustrates an example of a user interface provided based on screen orientation of the electronic device according to various embodiments of the present disclosure.

As illustrated in FIG. 33, FIG. 33 may show the case in which the electronic device is a smart phone. According to various embodiments, a mode specific for the orientation of the electronic device may be provided.

Referring to FIG. 33, the electronic device may configure and provide the basic diagnosis mode in a portrait mode 3310 and configure and provide the ultrasound diagnosis and telemedicine mode in a portrait mode 3320. For example, the electronic device may display a user interface related to the basic diagnosis mode to provide the user interface in the portrait mode 3310. When switching from the portrait mode 3310 to the landscape mode 3320, the electronic device may switch the mode from the basic diagnosis mode to the ultrasound diagnosis and telemedicine mode and display a user interface related to the ultrasound diagnosis and telemedicine mode to provide the user interface to the user.

According to various embodiments, in the portrait mode, the electronic device may provide only the ultrasound image without showing a video call screen, which results in concentration on the ultrasound diagnosis. When switching from the portrait mode to the landscape mode, the electronic device may provide both the ultrasound diagnosis image and the video call screen for telemedicine.

According to various embodiments, the electronic device may detect orientation switching (or rotation) of the electronic device. For example, a change from portrait mode to landscape mode or a change from landscape mode to portrait mode may be determined. The electronic device may switch and provide a corresponding specific mode on the basis of the determined mode.

FIG. 34 illustrates a menu configuration example in the electronic device according to various embodiments of the present disclosure.

As illustrated in FIG. 34, according to various embodiments, a preset and a shortcut of mainly used menus may be configured by the user.

As illustrated in a screen 3410, the user may variously configure the types of a mainly used menu (for example, a main menu) and a display location (or direction) of the menu according to medical treatment of the user (for example, a doctor), a department, or a diagnosis characteristic through an edit menu of the shortcut. The electronic device may configure and dispose main menus according to user settings and provide the configured and disposed main menus.

According to an embodiment, the electronic device may display mainly used menus according to user settings and provide the menus to the user as illustrated in a screen 3420 and a screen 3430.

Figure 35:
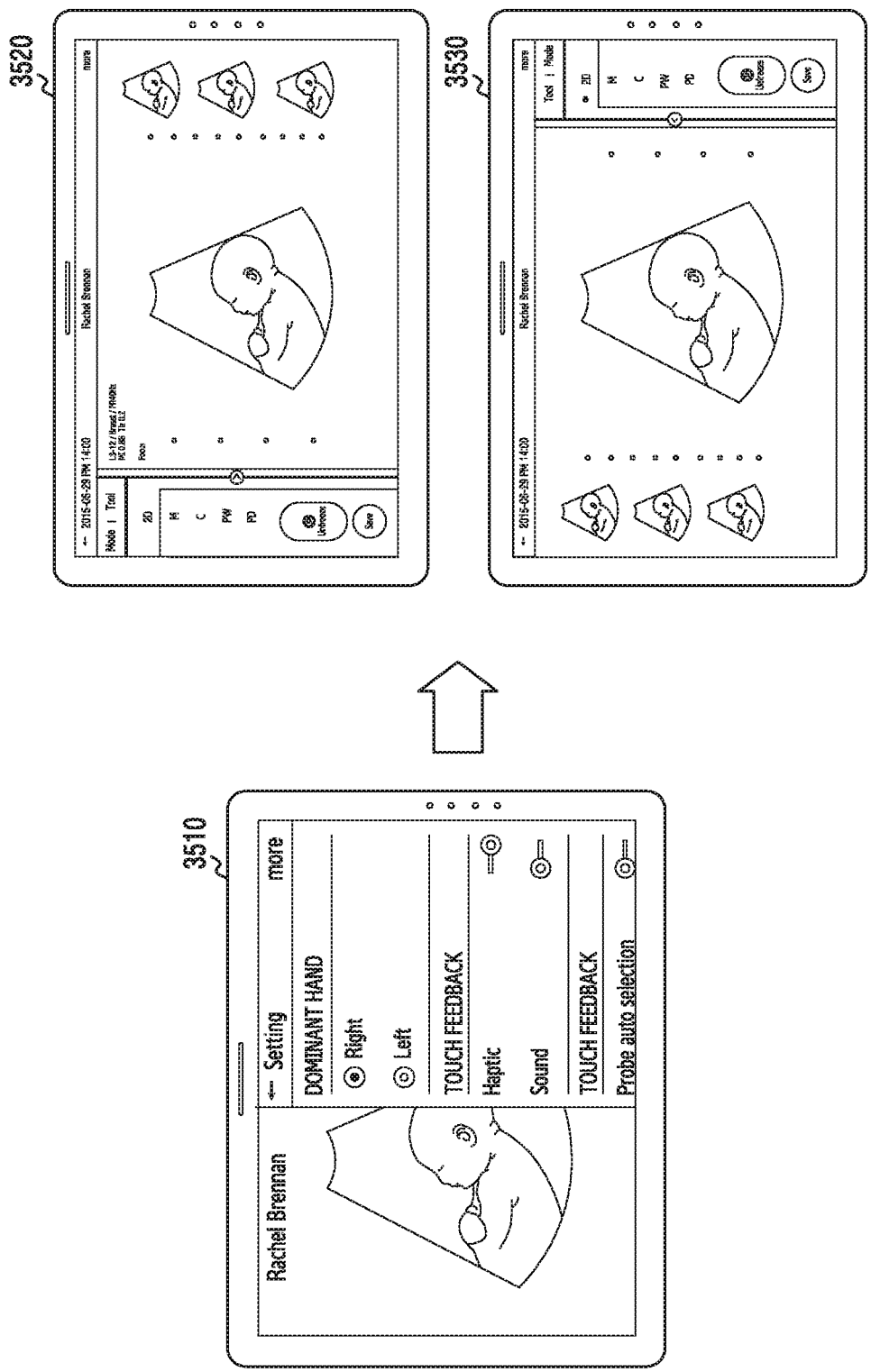
FIGS. 35 and 36 are diagrams illustrating examples in which the electronic device provides a screen interface according to various embodiments of the present disclosure.
Figure 36:
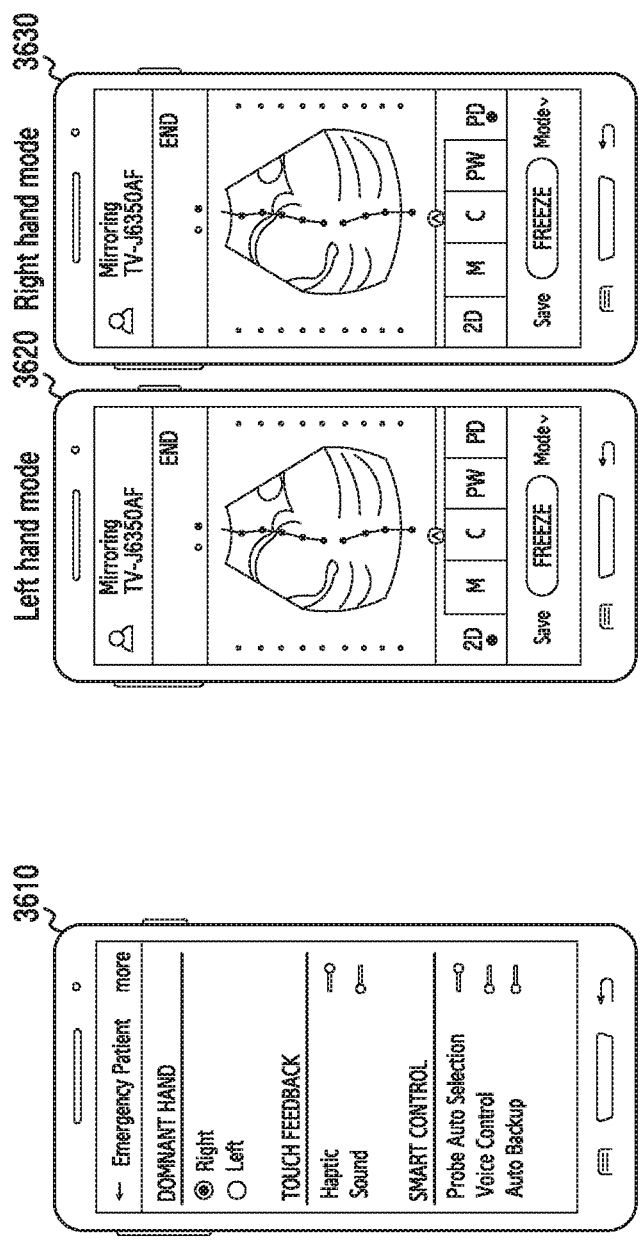

FIGS. 35 and 36 are diagrams illustrating examples in which the electronic device provides a screen interface according to various embodiments of the present disclosure.

As illustrated in FIGS. 35 and 36, FIG. 35 may illustrate the case in which the electronic device is a tablet PC and FIG. 36 may illustrate the case in which the electronic device is a smart phone. According to various embodiments, the electronic device may configure a mainly used hand of the user and determine a grasp state or a diagnosis pose, and may provide a screen interface for each of a left hand mode and a right hand mode on the basis of the determination result.

Referring to FIGS. 35 and 36, as illustrated in screens 3510 and 3610, the user may configure a left hand or a right hand as the hand mainly used by the user (for example, a dominant hand) through configuration menus. The electronic device may configure the left hand mode or the right hand mode on the basis of user settings.

According to various embodiments, the electronic device may display a screen interface in the left hand mode to provide the screen interface to the user as illustrated in screens 3520 and 3620 or display a screen interface in the right hand mode to provide the screen interface to the user as illustrated in screens 3530 and 3630 on the basis of user settings.

According to various embodiments, the electronic device does not limit to displaying the screen interface in any particular mode on the basis of user settings, but may adaptively change and provide the left hand mode or the right hand mode on the basis of context awareness For example, the electronic device may include various sensors (for example, one or more of a motion sensor, a proximity sensor, a pressure sensor, and a capacitance sensor), and may determine a diagnosis pose using the electronic device or a grasp state of the electronic device on the basis of sensor information measured through the sensor.

According to an embodiment, the electronic device may detect a change in one or more of motion, contact area, capacitance, and pressure and determine whether the grasp state of the user is a grasp state by the left hand or the grasp state by the right hand based at least partially on the detection.

When the electronic device determines the grasp by the left hand on the basis of the determination result, the electronic device may display a screen interface by the left hand mode. When the electronic device determines the grasp by the right hand, the electronic device may display a screen interface by the right hand mode.

Figure 37:
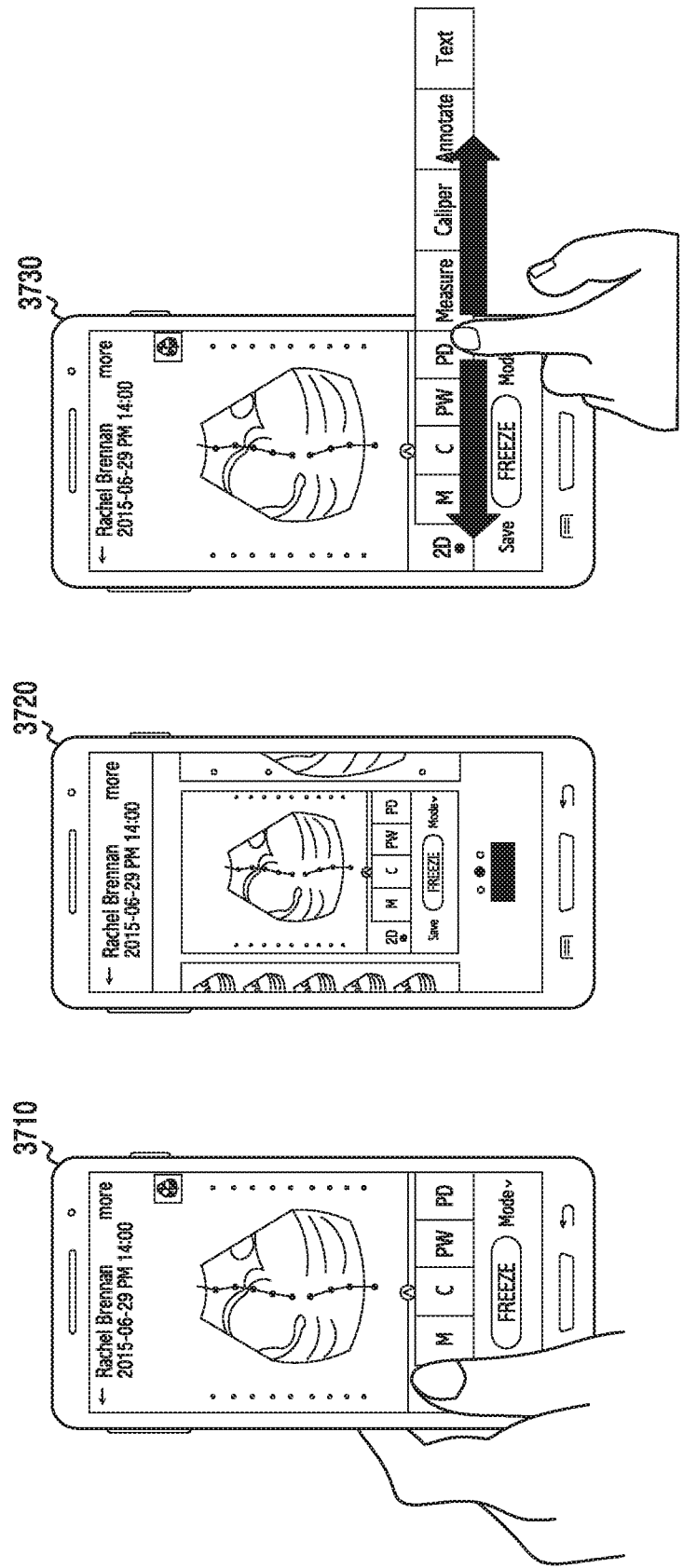
FIG. 37 is a diagram illustrating a user interaction-based operation in the electronic device according to various embodiments of the present disclosure.

FIG. 37 is a diagram illustrating a user interaction-based operation in the electronic device according to various embodiments of the present disclosure.

As illustrated in FIG. 37, FIG. 37 may show the case in which the electronic device is a smart phone. According to various embodiments, an electronic device having a small screen such as a smart phone may provide user convenience through an efficient GUI (for example, buttons) arrangement. For example, in the state in which the user grasps the electronic device, a screen interface may be provided to allow the user to switch a screen, a function, or a menu based on a one-finger interaction. According to various embodiments, the one-finger interaction may include, for example, particular user input (for example, long press, swipe, or flick) based on a user's finger.

As illustrated in a screen 3710, in the state in which the user grasps the electronic device, buttons corresponding to main functions or menus may be disposed and provided within a range within which the control by a user's thumb is possible. The user may select a button or switch a screen through the one-finger interaction.

According to various embodiments, the electronic device may perform screen switching, function switching, or menu switching based on the user's one-finger interaction and provide a GUI related to the switching operation.

According to an embodiment, as illustrated in a screen 3720, the electronic device may provide an ultrasound diagnosis screen, a video call screen, main menus, sub menus, or a screen switching effect (for example, slide in/out, fade in/output, or image transition) for switching between the diagnosis mode and the tool. According to an embodiment, as illustrated in a screen 3730, the user may conveniently perform mode switching within a menu area through the one-finger interaction (for example, swipe) in a menu area.

Figure 38:
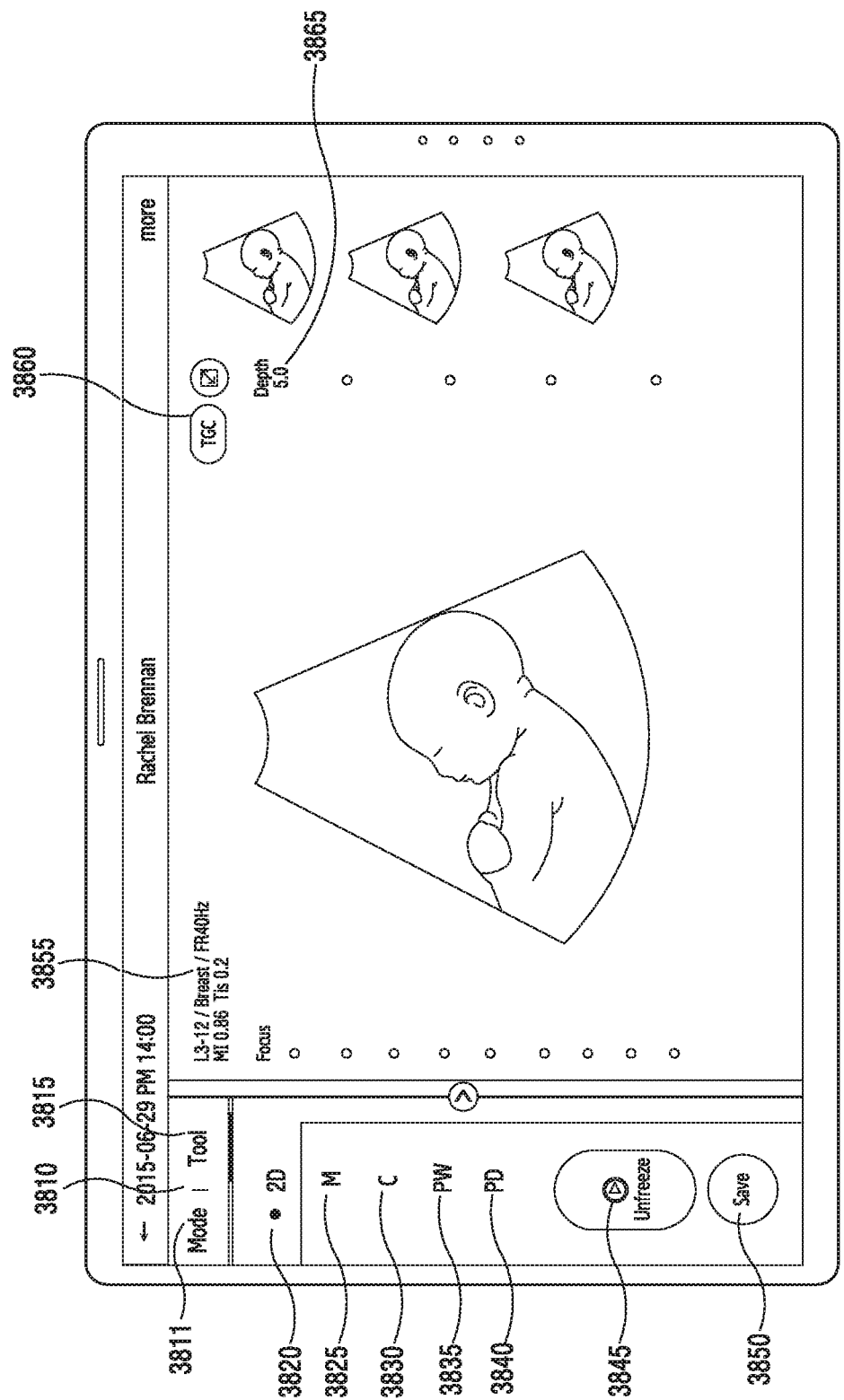
FIGS. 38, 39, and 40 are diagrams illustrating examples of a screen interface provided by the electronic device according to various embodiments of the present disclosure.
Figure 39:
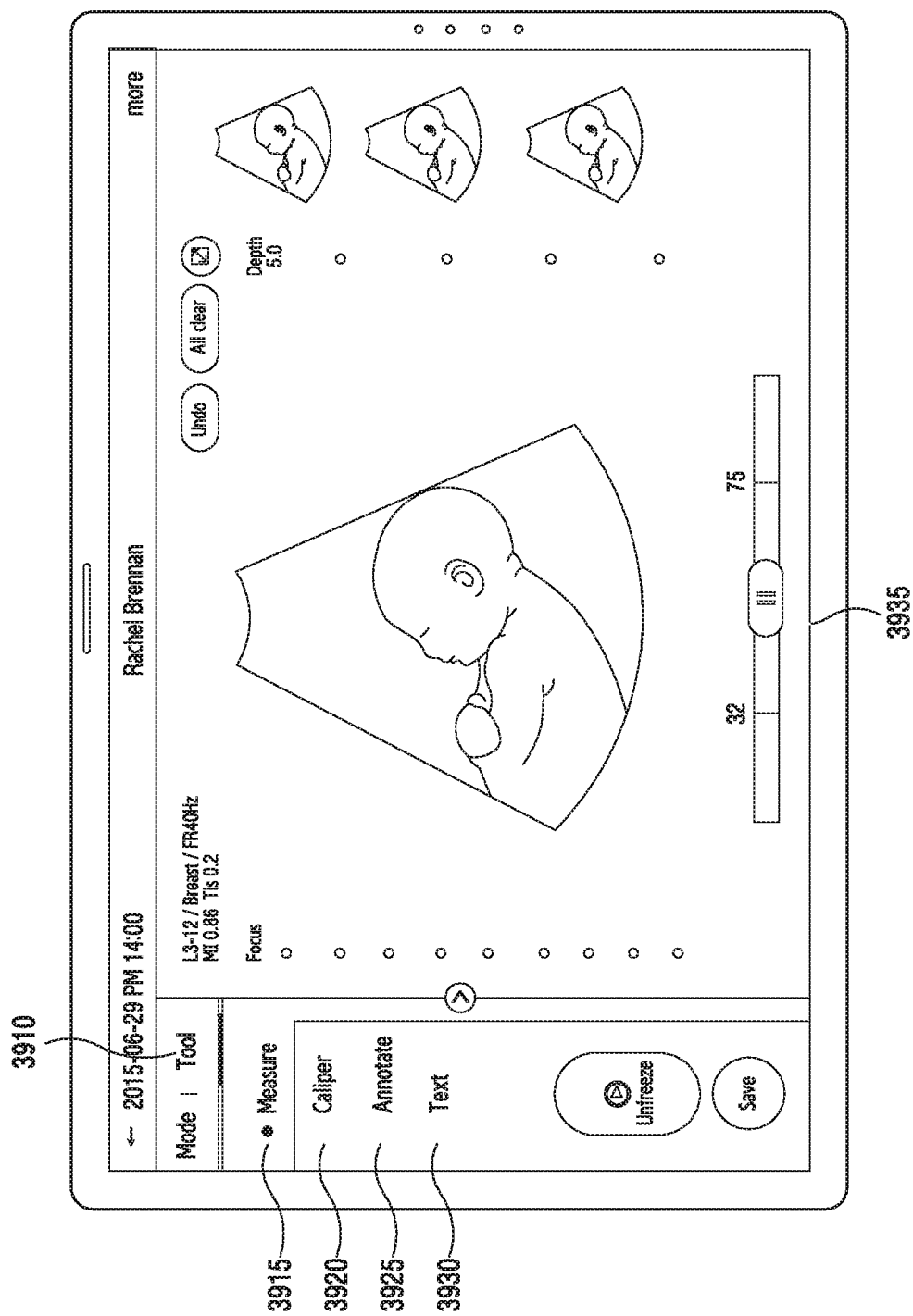
Figure 40:
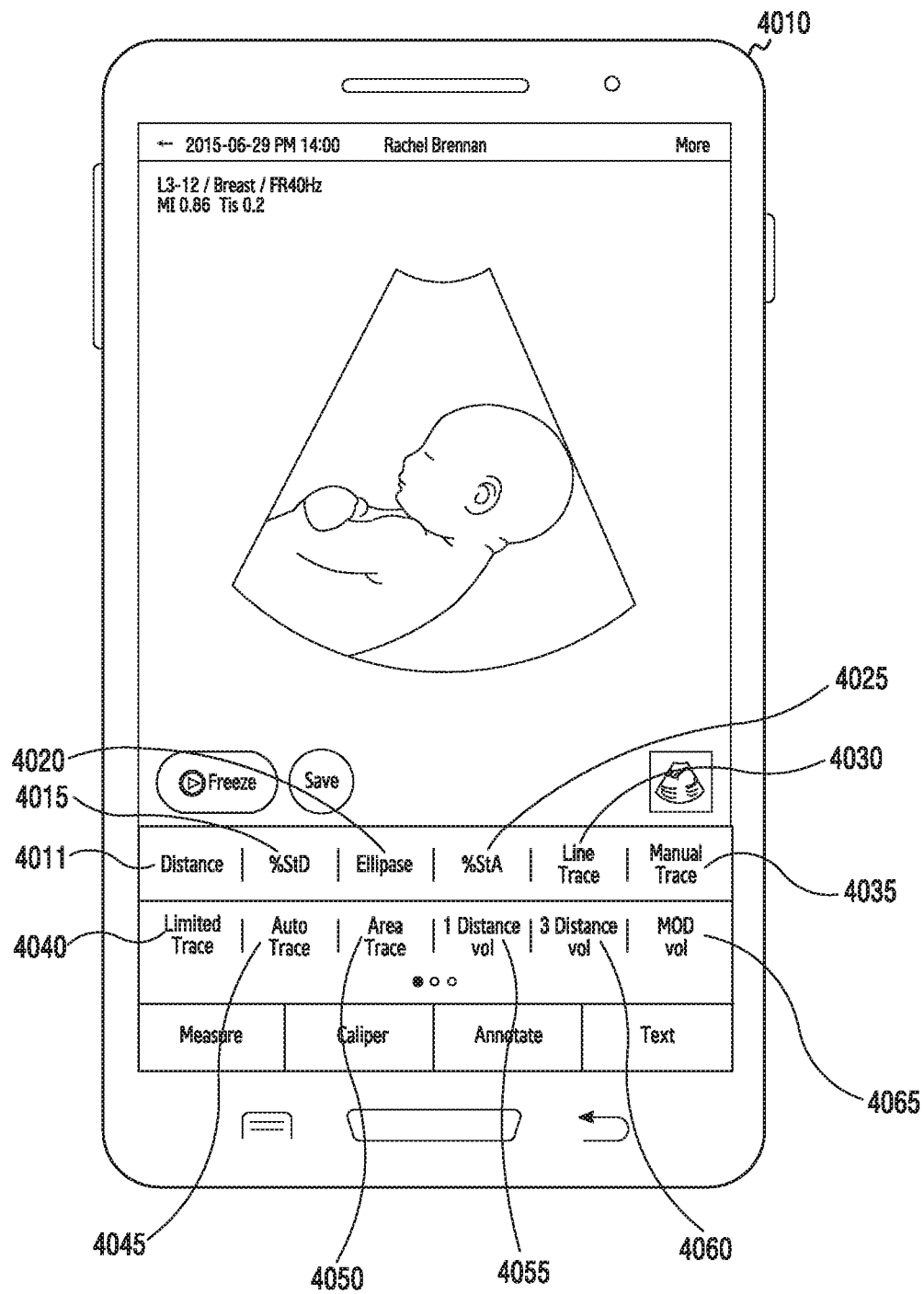

FIGS. 38, 39, and 40 are diagrams illustrating examples of a screen interface provided by the electronic device according to various embodiments of the present disclosure.

Referring to FIGS. 38, 39, and 40, FIGS. 38, 39, and 40 may indicate a screen interface provided in an ultrasound diagnosis mode of the electronic device (for example, a tablet PC), menus thereof, or functions, or examples illustrating the functions. According to various embodiments, FIGS. 38 and 39 may show examples in which the electronic device provides a screen interface according to a basic diagnosis mode in a horizontal direction, and FIG. 40 may show an example in which the electronic device provides a screen interface according to a precise reading mode in a vertical direction.

As illustrated in FIGS. 38 and 39, the screen interface in the basic diagnosis mode may largely include an ultrasound image area, a menu area, and a gallery area.

The ultrasound image area may provide at least one of an ultrasound image, which is photographed in real time by the probe 600, and a live or preview image, which is photographed by the camera. According to various embodiments, the ultrasound image area may include and provide an area 3865 for controlling a depth of the ultrasound image and for depth information related thereto, an area 3857 for controlling a focus (for example, similar to a camera focus) at a particular position of the ultrasound image and for focus information related thereto, an area 3855 for information of the probe 600 currently used, a configuration preset value, and image information, or a Total Gain Control (TGC) button 3860 for calibrating brightness or quality of the image.

The menu area may indicate an area for selecting and execution various menus or functions related to an ultrasound diagnosis or measurement in the ultrasound diagnosis mode based at least partially on the image displayed in the ultrasound image area. According to various embodiments, the menu area may include a main control area and a mode/tool area.

The main control area may include and provide a button 3845 for freezing or unfreezing the ultrasound image or a button 3850 for saving an image or a captured image.

The mode/tool area may include a mode button 3810 for loading and displaying menus related to configuration of the ultrasound diagnosis mode and a tool button 3815 for measuring a lesion or an additional function such as memo input, and may include and provide relevant menu button according to activation of the mode button 3810 or the tool button 3815. For example, when the mode button 3810 is activated, mode selection buttons (for example, 2D 3820, M 3825, C 3830, PW 3835, and PD 3840) related to the ultrasound diagnosis mode may be provided as illustrated in FIG. 38, and when the tool button 3815 is activated, function selection buttons (for example, Measure 3915, Caliper 3920, Annotate 3925, and Text 3930) related to additional functions may be provided as illustrated in FIG. 39.

According to various embodiments, 2D 3820 may indicate a mode for displaying a cross section of an organ as a basic ultrasound diagnosis mode, M 3825 may indicate a mode for designating an area to be observed within a 2D image as an M line and displaying a change according to time, C 3830 may indicate a mode for displaying in color a blood flow pattern in a Region Of Interest (ROI) within the 2D image, PW 3835 corresponds to a pulse wave and may indicate a mode for hourly displaying a blood flow speed at a particular location within a blood vessel, and PD 3840 corresponds to power Doppler and may indicate a mode for displaying in color a strength of a blood flow in the ROI of the 2D image. According to various embodiments, Measure 3915 may indicate a tool menu for lesion measurement and record, Caliper 3920 may indicate a tool menu for lesion measurement and temporary measurement, Annotate 3925 may indicate a tool menu for inputting text, an indicator, or a marker (for example, BodyMarker) to the image, and Text 3930 may indicate a tool menu for inputting text to the image.

According to various embodiments, when the tool button 3815 is activated, Cine bar 3935 for playing a particular section of the ultrasound image and pause to check the section may be activated and provided in the ultrasound image area as illustrated in FIG. 39.

The gallery area may provide a captured or stored image in the ultrasound diagnosis mode in a thumbnail form.

As illustrated in FIG. 40, the screen interface in the precise reading mode may largely include an ultrasound image area, a main control area, a Cine bar area (hide or view), a gallery area, a 2-depth menu area (for example, a sub menu area), and a 1-depth menu area (for example, a tool menu area).

In the precise reading mode, the 2-depth menu may include and provide various sub menus as illustrated in FIG. 40, and each sub menu may be defined in [Table 1] below.

TABLE 1

| Menu | Definition | Menu | Definition |
|---|---|---|---|
| Distance | Put two points and measure length therebetween | Limited Trace | Configure section through double click, and automatically track and draw Loop of Doppler in configured section |
| Line trace | Measure distance by detecting movement of trackball after click | Auto trace | Automatically track and display Loop of Doppler |
| 2 lines | Measure angle between | D | Calculate difference |

TABLE 1-continued

| Menu | Definition | Menu | Definition |
|---|---|---|---|
| angle | two lines by putting two points, respectively | Velocity | in velocity by putting two points on Doppler screen, wherein operation of clicking calculated two points is same as that for distance with only difference in that area is Doppler area |
| 3 points angle | Put two points and then open lines to measure angle | D time | Calculate time of Doppler by clicking two points, wherein operation of clicking calculated two points is same as that for distance with only difference in that area is Doppler area |
| % Std | Put four points for two lines and measure distance | D A/B | Calculate ratio of Doppler speed by clicking two points |
| M distance | Measure distance on Loop | 3 Distance Vol | Measure volume by performing Distance three times, wherein volume is calculated using three lines based on measurement of distance twice, respectively |
| Ellipse | Calculate area of ellipse; when two points are put, circle is created with diameter of corresponding line and area of ellipse is calculated through trackball | MOD Vol | Perform area trace and then click longest line within area |
| Area trace | When putting point and moving to put next point through trackball, closed area is calculated by drawing line between two points | 1 Distance Vol. | When two points are clicked like Lin distance, volume result value is provided |
| % StA | Calculate ratio by performing Ellipse twice | Ellipse Vol. | When Ellipse is measured, volume result value is provided, which is same as measurement method of Ellipse |
| Manual trace | Line drawing using Trace in Doppler, which is same as Line trace with only different in that area is Doppler area | Dist + Ellipse Vol. | When Ellipse is measured after measurement of line distance, volume result value is provided |

As described above, a method of operating the electronic device 400 according to various embodiments of the present disclosure may include an operation of an ultrasound diagnosis mode, an operation of executing the ultrasound diagnosis mode and establishing communication with a configured external device (for example, the second electronic device 500 and an external screen) in response to detection of the ultrasound diagnosis mode, an operation of acquiring data in the ultrasound diagnosis mode, an operation of displaying the data through a display (for example, the display 631 or the touch screen 630) and transmitting the data streaming to the external device through a communication circuit (for example, the wireless communication unit 610), and an operation of providing a control guide of the probe 600 in response to reception of control information (for example, guide information) from the external device.

According to various embodiments, the operation of acquiring the data may include an operation of acquiring first data (for example, an ultrasound image or ultrasound scan data) photographed through the probe connected to the electronic device, an operation of acquiring second data (for example, a probe control image or affected part image data) photographed through a camera of the electronic device, an operation of displaying at least one of the first data and the second data in a configured scheme, and an operation of transmitting the first data and the second data to the external device.

According to various embodiments, the method may further include an operation of automatically connecting a voice call or a video call with the external device.

According to various embodiments, the operation of transmitting the first data and the second data may include an operation of transmitting the data acquired in the ultrasound diagnosis mode to at least one of the external device and an external screen, which is different from the external device, and an operation of performing a configured call connection with the external device.

According to various embodiments, the operation of providing the control guide may include an operation of receiving the control information transmitted based at least partially on the data from the external device, and an operation of processing an output of an indicator corresponding to the control information based at least partially on the data or the probe.

According to various embodiments, the operation of detecting the ultrasound diagnosis mode may include an operation of detecting a detection signal by the probe, an operation of determining execution of an emergency diagnosis mode in response to the detection signal, and an operation of providing an emergency preset.

According to various embodiments, the operation of providing the emergency preset may include an operation of omitting a preset configuration step in the emergency diagnosis mode and providing simple menus.

As described above, a method of operating the electronic device 500 according to various embodiments of the present disclosure may include an operation of establishing communication with an external device (for example, the first electronic device 400), an operation of receiving data streaming from the external device, an operation of performing at least one of displaying the data and mirroring the data to an external screen (for example, a TV or a monitor), an operation of receiving control information (for example, guide information) related to control of the probe 600 connected to the external device based at least partially on the data, and an operation of transmitting the control information to the external device.

According to various embodiments, the data may include at least one of first data (for example, an ultrasound image or ultrasound scan data) photographed through the probe 600 connected to the external device and second data (for example, a probe control image or affected part image data) photographed through a camera (for example, the camera module 670) of the external device.

According to various embodiments, the method may further include an operation of making a call connection with the external device along with reception of the data.

According to various embodiments, the method may include an operation of receiving user input for guiding the probe 600 based at least partially on the data, an operation of generating the control information based on the user input, and an operation of transmitting the control information to the external device.

According to various embodiments, the method may further include an operation of executing a communication mode and an operation of performing image processing related to sharing of the data based on the communication mode. According to various embodiments, the processor may further include an operation of executing the communication mode and an operation of performing image processing (for example, image processing for transmitting data to the connected external device and switching a screen, that is, screen sharing) based on the communication mode.

The embodiments of the present disclosure disclosed herein and shown in the drawings are merely specific examples presented in order to easily describe technical details of the present disclosure and to help the understanding of the present disclosure, and are not intended to limit the scope of the present disclosure. Therefore, it should be construed that, in addition to the embodiments disclosed herein, all modifications and changes or modified and changed forms derived from the technical idea of the present disclosure fall within the scope of the present disclosure.

The invention claimed is:

1. An electronic device comprising:
a display;
a camera;
a first communication circuit for a connection to a probe being an ultrasonic probe;
a second communication circuit for communication with at least one external device; and
a processor operatively connected to the display, the camera, the first communication circuit, and the second communication circuit,
wherein the processor is configured to:
in response to execution of a function related to ultrasound diagnosis based on the connection to the probe, establish first communication with the probe by using the first communication circuit, and establish second communication with the at least one external device by using the second communication circuit,
obtain data comprising first data regarding an ultrasound image obtained by using the probe and second data regarding an image photographed by using the camera, wherein the image photographed by using the camera comprises a shape of at least a part of the probe photographed by using the camera,
display a screen comprising the ultrasound image and the image photographed by using the camera,
transmit the data to the at least one external device through the second communication,
obtain third data, from the at least one external device through the second communication, including information regarding movement of the location of probe, and
display, on the display, a direction indicator overlapping the image at a position corresponding to the third data to indicate a direction for moving the location of the probe,
wherein the position surrounds the shape of at least the part of the probe in the image, and
wherein the third data corresponds to an input which is received by the at least one external device as a response to displaying at least one of the ultrasound image or the image on the at least one external device.

2. The electronic device of claim 1, wherein the processor is configured to automatically connect a voice call or a video call with the external device.

3. The electronic device of claim 1, wherein the processor is further configured to:
transmit the data to at least one of the external device and an external screen, which is different from the external device, and
perform a configured call connection with the external device.

4. The electronic device of claim 1, wherein the processor is further configured to:
transmit a signal regarding the movement of the location of the probe to the probe through the first communication to control a light emitting device of the probe to emit light to indicate the direction corresponding to the third data.

5. The electronic device of claim 1, wherein the processor is further configured to:
detect a detection signal by the probe,
determine execution of an emergency diagnosis mode in response to the detection signal,
provide an emergency preset, and
in the emergency diagnosis mode, omit a preset configuration step and provide simple menus.

6. An electronic device comprising:
a display;
a communication circuit for communication with an external device; and
a processor operatively connected to the display and the communication circuit,
wherein the processor is configured to:
establish communication with the external device,
receive data comprising first data regarding an ultrasound image obtained by using an ultrasonic probe connected to the external device and second data regarding an image photographed by using a camera from the external device, wherein the image photographed by using the camera comprises a shape of at least a part of the ultrasonic probe photographed by using the camera,
perform at least one of displaying a screen comprising the ultrasound image and the image and mirroring the screen to an external screen,
receive control information for displaying a direction indicator regarding movement of the location of the ultrasonic probe, based at least partially on the displayed or mirrored image, and
transmit third data including the control information to control the external device to display, through the external device, a direction indicator overlapping an image photographed by using the camera at a position corresponding to the third data to indicate a direction for moving the location of the probe, wherein the position surrounds the shape of at least the part of the probe in the image.

7. The electronic device of claim 6, wherein the processor is configured to perform a call connection with the external device along with reception of the data.

8. The electronic device of claim 7, wherein the processor is configured to:
execute a communication mode, and
perform image processing related to sharing of the data based on the communication mode.

9. A method of operating an electronic device, the method comprising:
in response to execution of a function related to ultrasound diagnosis based on the connection to a probe being an ultrasonic probe, establishing first communication with the probe, and establishing second communication with a configured external device;

obtaining data comprising first data regarding an ultrasound image obtained by using the probe and second data regarding an image photographed by using a camera, wherein the image photographed by using the camera comprises a shape of at least a part of the probe photographed by using the camera;

displaying a screen comprising the ultrasound image and the image photographed by using the camera;

transmitting the data to the external device through the second communication;

obtaining third data, from the external device through the second communication, including information regarding movement of the location of probe; and displaying a direction indicator overlapping the image at a position corresponding to the third data to indicate a direction for moving the location of the probe, wherein the position surrounds the shape of at least the part of the probe in the image, wherein the third data corresponds to an input which is received by the at least one external device as a response to displaying at least one of the ultrasound image or the image on the at least one external device.

10. The method of claim 9, wherein transmitting the first data and the second data comprises:

transmitting the data to at least one of the external device and an external screen, which is different from the external device; and performing a configured call connection with the external device.

11. The method of claim 9, further comprising:

transmitting a signal regarding the movement of the location of the probe through the first communication to control a light emitting device of the probe to emit light to indicate the direction corresponding to the third data.

12. A method of operating an electronic device, the method comprising:

establishing communication with an external device;

receiving data comprising first data regarding an ultrasound image obtained by using an ultrasonic probe connected to the external device and second data regarding an image photographed by using a camera from the external device, wherein the image photographed by using the camera comprises a shape of the ultrasonic probe photographed by using the camera;

performing at least one of displaying a screen comprising the ultrasound image and the image and mirroring the screen to an external screen;

receiving control information for displaying a direction indicator regarding movement of the location of the ultrasonic probe based at least partially on the displayed or mirrored image; and transmitting third data including the control information to control the external device to display, through the external device, a direction indicator overlapping an image photographed by using the camera at a position corresponding to the third data to indicate a direction for moving the location of the probe, wherein the position surrounds the shape of at least the part of the probe in the image.

13. The method of claim 12, wherein receiving the data comprises performing a call connection with the external device along with reception of the data.

* * * * *